United States Patent
Young et al.

(10) Patent No.: US 6,620,912 B2
(45) Date of Patent: *Sep. 16, 2003

(54) DENDRITIC ENRICHED SECRETED LYMPHOCYTE ACTIVATION MOLECULE

(75) Inventors: Paul E. Young, Gaithersburg, MD (US); Steven M. Ruben, Olney, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/369,248

(22) Filed: Aug. 5, 1999

(65) Prior Publication Data

US 2003/0022276 A1 Jan. 30, 2003

Related U.S. Application Data

(63) Continuation-in-part of application No. 09/244,110, filed on Feb. 4, 1999.
(60) Provisional application No. 60/073,962, filed on Feb. 6, 1998, and provisional application No. 60/078,572, filed on Mar. 19, 1998.

(51) Int. Cl.[7] .................... C07K 14/47; C12N 15/12; C12N 5/10; C12P 21/02
(52) U.S. Cl. .................... 530/350; 536/23.5; 435/69.1; 435/71.1; 435/320.1; 435/471
(58) Field of Search .................... 530/350; 536/23.5; 435/69.1, 71.1, 320.1, 471

(56) References Cited

U.S. PATENT DOCUMENTS 5,576,423 A   11/1996   Aversa et al.

FOREIGN PATENT DOCUMENTS

| WO | WO 94/01548 | 1/1994 |
|----|-------------|--------|
| WO | WO 99/40184 | 8/1999 |
| WO | WO 00/18800 | 4/2000 |

OTHER PUBLICATIONS

Kingsbury, Gillian et al., "Cloning, Expression, and Function of Blame, a Novel Member of the CD2 Family", J. of Immunology, 166:5675–5680 (2001).

International Search Report, Application No. PCT/US00/21130, mailed Nov. 14, 2000.

Punnonen et al., "Soluble and Membrane–bound forms of signaling lymphocytic activation molecule (SLAM) induce proliferation and Ig synthesis by activated Human B lymphocytes," J. Exp. Med. 185(6):993–1004 (1997).

Ferrante et al., "Cytokine production and surface marker expression in acute and stable multiple sclerosis: altered IL–12 production and augmented signaling lymphocytic activation Molecule (SLAM)–expressing lymphocytes in acute multiple sclerosis," J. Immunol. 185(6):1514–1521 (1998).

Genbank Accession No. AF14235 (Jun. 1, 1999).

Genbank Accession No. N62522 (Mar. 1, 1996), Hillier et al.

Genbank Accession No. AA627522 (Oct. 31, 1997), Strausberg et al.

Genbank Accession No. R11635 (Apr. 11, 1995), Hillier et al.

Genbank Accession No. AA379112 (Apr. 21, 1997), Adams et al.

Genbank Accession No. R09841 (Apr. 6, 1995), Hillier et al.

Genbank Accession No. Z20320 (Feb. 7, 1995), MRC Human Genome Mapping Project.

Genbank Accession No. N79421 (Apr. 2, 1996), Hillier et al.

Genbank Accession No. D45800 (Feb. 20, 1995), Itoh et al.

Genbank Accession No. AA917335 (Jun. 24, 1998), Strausberg et al.

Genbank Accession No. AI094818 (Oct. 1, 1998), Strausberg et al.

Genbank Accession No. G22227 (May 31, 1996), Hudson.

Cocks et al. (1995) Nature 376:260–263.

Geneseq Accession No. Q76829 (1994), Gross et al.

Primary Examiner—Yvonne Eyler
Assistant Examiner—Fozia Hamud

(57) ABSTRACT

The present invention relates to a novel human protein called Dendritic Enriched Secreted Lymphocyte Activation Molecule, and isolated polynucleotides encoding this protein. Also provided are vectors, host cells, antibodies, and recombinant methods for producing this human protein. The invention further relates to diagnostic and therapeutic methods useful for diagnosing and treating disorders related to this novel human protein.

95 Claims, 6 Drawing Sheets

FIG. 1A

```
  1 GAAGGACCACAGCTCCTCCCGTGCATCCACTCGGCCTGGGAGGTTCTGGATTTTGGCTGT  60

61 CGAGGGAGTTTGCCTGCCTCTCCAGAGAAAGATGGTCATGAGGCCCCTGTGGAGTCTGCT 120
  1                                  M  V  M  R  P  L  W  S  L  L  10

121 TCTCTGGGAAGCCCTACTTCCCATTACAGTTACTGGTGCCCAAGTGCTGAGCAAAGTCGG 180
 10  L  W  E  A  L  L  P  I  T  V  T  G  A  Q  V  L  S  K  V  G  30

181 GGGCTCGGTGCTGCTGGTGGCAGCGCGTCCCCCTGGCTTCCAAGTCCGTGAGGCTATCTG 240
 30  G  S  V  L  L  V  A  A  R  P  P  G  F  Q  V  R  E  A  I  W  50

241 GCGATCTCTCTGGCCTTCAGAAGAGCTCCTGGCCACGTTTTTCCGAGGCTCCCTGGAGAC 300
 50  R  S  L  W  P  S  E  E  L  L  A  T  F  F  R  G  S  L  E  T  70

301 TCTGTACCATTCCCGCTTCCTGGGCCGAGCCCAGCTACACAGCAACCTCAGCCTGGAGCT 360
 70  L  Y  H  S  R  F  L  G  R  A  Q  L  H  S  N  L  S  L  E  L  90

361 CGGGCCGCTGGAGTCTGGAGACAGCGGCAACTTCTCCGTGTTGATGGTGGACACAAGGGG 420
 90  G  P  L  E  S  G  D  S  G  N  F  S  V  L  M  V  D  T  R  G 110

421 CCAGCCCTGGACCCAGACCCTCCAGCTCAAGGTGTACGATGCAGTGCCCAGGCCCGTGGT 480
110  Q  P  W  T  Q  T  L  Q  L  K  V  Y  D  A  V  P  R  P  V  V 130

481 ACAAGTGTTCATTGCTGTAGAAAGGGATGCTCAGCCCTCCAAGACCTGCCAGGTTTTCTT 540
130  Q  V  F  I  A  V  E  R  D  A  Q  P  S  K  T  C  Q  V  F  L 150

541 GTCCTGTTGGGCCCCCAACATCAGCGAAATAACCTATAGCTGGCGACGGGAGACAACCAT 600
150  S  C  W  A  P  N  I  S  E  I  T  Y  S  W  R  R  E  T  T  M 170

601 GGACTTTGGTATGGAACCACACAGCCTCTTCACAGACGGACAGGTGCTGAGCATTTCCCT 660
170  D  F  G  M  E  P  H  S  L  F  T  D  G  Q  V  L  S  I  S  L 190

661 GGGACCAGGAGACAGAGATGTGGCCTATTCCTGCATTGTCTCCAACCCTGTCAGCTGGGA 720
190  G  P  G  D  R  D  V  A  Y  S  C  I  V  S  N  P  V  S  W  D 210

721 CTTGGCCACAGTCACGCCCTGGGATAGCTGTCATCATGAGGCAGCACCAGGGAAGGCCTC 780
210  L  A  T  V  T  P  W  D  S  C  H  H  E  A  A  P  G  K  A  S 230

781 CTACAAAGATGTGCTGCTGGTGGTGGTGCCTGTCTCGCTGCTCCTGATGCTGGTTACTCT 840
230  Y  K  D  V  L  L  V  V  V  P  V  S  L  L  L  M  L  V  T  L 250
```

FIG. 1B

```
 841 CTTCTCTGCCTGGCACTGGTGCCCCTGCTCAGGGAAAAAGAAAAAGGATGTCCATGCTGA  900
 250  F  S  A  W  H  W  C  P  C  S  G  K  K  K  D  V  H  A  D     270

901 CAGAGTGGGTCCAGAGACAGAGAACCCCCTTGTGCAGGATCTGCCATAAAGGACAATATG  960
 270  R  V  G  P  E  T  E  N  P  L  V  Q  D  L  P  *              285

961 AACTGATGCCTGGACTATCAGTAACCCCACTGCACAGGCACACGATGCTCTGGGACATAA 1020

1021 CTGGTGCCTGGAAATCACCATGGTCCTCATATCTCCCATGGGAATCCTGTCCTGCCTCGA 1080

1081 AGGAGCAGCCTGGGCAGCCATCACACCACGAGGACAGGAAGCACCAGCACGTTTCACACC 1140

1141 TCCCCCTTCCCTCTCCCATCTTCTCATATCCTGGCTCTTCTCTGGGCAAGATGAGCCAAG 1200

1201 CAGAACATTCCATCCAGGACACTGGAAGTTCTCCAGGATCCAGATCCATGGGGACATTAA 1260

1261 TAGTCCAAGGCATTCCCTCCCCCACCACTATTCATAAAGTATTAACCAACTGGCACCAAG 1320

1321 GAATTGCCTCCAGCCTGAGTCCTAGGCTCTAAAAGATATTACATATTTGAACTAATAGAG 1380

1381 GAACTCTGAGTCACCCATGCCAGCATCAGCTTCAGCCCCAGACCCTGCAGTTTGAGATCT 1440

1441 GATGCTTCCTGAGGGCCAAGGCATTGCTGTAAGAAAAGGTCTAGAAATAGGTGAAAGTGA 1500

1501 GAGGTGGGGGACAGGGGTTTCTCTTTCTGGCCTAAGGACTTTCAGGTAATCAGAGTTCAT 1560

1561 GGGCCCTCAAAGGTAAATTGCAGTTGTAGACACCGAGGATGGTTGACAACCCATGGTTGA 1620

1621 GATGGGCACCGTTTTGCAGGAAACACCATATTAATAGACATCCTCACCATCTCCATCCGC 1680

1681 TCTCACGCCTCCTGCAGGATCTGGGAGTGAGGGTGGAGAGTCTTTCCTCACGCTCCAGCA 1740

1741 CAGTGGCCAGGAAAAGAAATACTGAATTTGCCCCAGCCAACAGGACGTTCTTGCACAACT 1800

1801 TCAAGAAAAGCAGCTCAGCTCAGGATGAGTCTTCCTGCCTGAAACTGAGAGAGTGAAGAA 1860

1861 CCATAAAACGCTATGCAGAAGGAACATTATGGAGAGAAAGGGTACTGAGGCACTCTAGAA 1920
```

FIG. 1C

```
1921 TCTGCCACATTCATTTTCAAATGCAAATGCAGAAGACTTACCTTAGTTCAAGGGGAGGGG 1980

1981 ACAAAGACCCCACAGCCCAACAGCAGGACTGTAGAGGTCACTCTGACTCCATCAAACTTT 2040

2041 TTATTGTGGCCATCTTAGGAAAATACATTCTGCCCCTGAATGATTCTGTCTAGAAAAGCT 2100

2101 CTGGAGTATTGATCACTACTGGAAAAACACTTAAGGAGCTAAACTTACCTTCGGGGATTA 2160

2161 TTAGCTGATAAGGTTCACAGTTTCTCTCACCCAGGTGTAACTGGATTTTTTCTGGGGCCT 2220

2221 CAATCCAGTCTTGATAACAGCGAGGAAAGAGGTATTGAAGAAACAGGGGTGGGTTTGAAG 2280

2281 TACTATTTTCCCCAGGGTGGCTTCAATCTCCCCACCTAGGATGTCAGCCCTGTCCAAGGA 2340

2341 CCTTCCCTCTTCTCCCCCAGTTCCCTGGGCAATCACTTCACCTTGGACAAAGGATCAGCA 2400

2401 CAGCTGGCCTCCAGATCCACATCACCACTCTTCCACTCGATTGTTCCCAGATCCTCCCTG 2460

2461 CCTGGCCTGCTCAGAGGTTCCCTGTTGGTAACCTGGCTTTATCAAATTCTCATCCCTTTC 2520

2521 CCACACCCACTTCTCTCCTATCACCTTCCCCCAAGATTACCTGAACAGGGTCCATGGCCA 2580

2581 CTCAACCTGTCAGCTTGCACCATCCCCACCTGCCACCTACAGTCAGGCCACATGCCTGGT 2640

2641 CACTGAATCATGCAAAACTGGCCTCAGTCCCTAAAAATGATGTGGAAAGGAAAGCCCAGG 2700

2701 ATCTGACAATGAGCCCTGGTGGATTTGTGGGGAAAAAATACACAGCACTCCCCACCTTTC 2760

2761 TTTCGTTCATCTCCAGGGCCCCACCTCAGATCAAAGCAGCTCTGGATGAGATGGGACCTG 2820

2821 CAGCTCTCCCTCCACAAGGTGACTCTTAGCAACCTCATTTCGACAGTGGTTTGTAGCGTG 2880

2881 GTGCACCAGGGCCTTGTTGAACAGATCCACACTGCTCTAATAAAGTTCCCATCCTTAATG 2940

2941 ACTCACTTGTCAACTAGTGGACTAATTAACCCTCCACCAAAAAAACACAAAGTGCTTCTG 3000

3001 TGAGACCAATTTTGTGCTAATGAGCATTGAGACTGATGCTTTGTAAGTCACACCACAACA 3060
```

FIG. 1D

```
3061 AATATTGATTGAGGGCGCTGCATGTGCTGGGTACATTTCTTGGCACTTGGGAATCAGTAG 3120

3121 TCAAGCGAAACCCTTGCCTTTGAGAGTTTATGGTCTGGATAATATAAATAAACAAGTAAG 3180

3181 CATAAAAAAAAAAAAAAAAAAAAAAAAAAAAAAAAAAAA 3220
```

FIG. 2

```
                    10          20          30          40
  1  M V M R P L W S L - - - - L L W E A L L P I T V T G A Q - - - - - - V L S K V G   HDPJP39.AA
  1  M D P K G L L S L T F V L F L S L A F G A S Y G T G G R M M N C P K I L R Q L G   gi/984969

50          60          70          80
 31  G S V L L V A A R P P G F Q - V R E A I W R S L W P S E E L - - - L A T F F R G   HDPJP39.AA
 41  S K V L L - - - - P L T Y E R I N K S M N K S I H I V V T M A K S L E N S V E N   gi/984969

90         100         110         120
 67  S L E T L Y H S - - - - - R F L G - R A Q L H - S N L S L E L G P L E S G D S G   HDPJP39.AA
 77  K I V S L D P S E A G P P R Y L G D R Y K F Y L E N L T L G I R E S R K E D E G   gi/984969

130         140         150         160
100  N F S V L M V D T R G Q P W T Q T L Q L K V Y D A V P R P V V Q V F I A V E R D   HDPJP39.AA
117  W Y - L M T L E K N V S V Q R F C L Q L R L Y E Q V S T P E I K V L - - - - N K   gi/984969

170         180         190         200
140  A Q P S K T C Q V F L S C W A P N I S E I T Y S W R R E T T M D F G M E P H S L   HDPJP39.AA
152  T Q E N G T C T L I L G C T V E K G D H V A Y S W S E K A - - - - G T H P L N P   gi/984969

210         220         230         240
180  F T D G Q V L S I S L G P G D R D V A Y S C I V S N P V S W D L A T V T P W D S   HDPJP39.AA
188  A N S S H L L S L T L G P Q H A D N I Y I C T V S N P I S N N S Q T F S P W P G   gi/984969

250         260         270         280
220  C H H E A P G K - - A S Y K D V L L V V P V S L L L M L V T L F S - - - A W       HDPJP39.AA
228  C R T D P S E T K P W A V Y A G L L G G V I M I L I M V V I L Q L R R R G K T N   gi/984969

290         300         310         320
255  H W C P C S G K K K K D V - - H A D R V G P - - - - - - - - - - - - - - - - -   HDPJP39.AA
268  H Y Q T T V E K K S L T I Y A Q V Q K P G P L Q K K L D S F P A Q D P C T T I Y   gi/984969

330         340
275  - E T E N P L V Q D L P .                                                         HDPJP39.AA
308  V A A T E P V P E S V Q E T N S I T V Y A S V T L P E S                           gi/984969
```

DENDRITIC ENRICHED SECRETED LYMPHOCYTE ACTIVATION MOLECULE

This application is a continuation-in-part of U.S. application Ser. No. 09/244,110 filed Feb. 4, 1999, which claims benefit of 35 U.S.C. § 119(e) based on copending U.S. Provisional Application Serial No. 60/073,962, filed Feb. 6, 1998, and Provisional Application Serial No. 60/078,572, filed Mar. 19, 1998, which are herein incorporated by reference in their entirety.

FIELD OF THE INVENTION

The present invention relates to a novel human gene encoding a polypeptide which is a member of the Secreted Lymphocyte Activation Molecule (SLAM) family. More specifically, the present invention relates to a polynucleotide encoding a novel human polypeptide named Dendritic Enriched Secreted Lymphocyte Activation Molecule, or "D-SLAM." This invention also relates to D-SLAM polypeptides, as well as vectors, host cells, antibodies directed to D-SLAM polypeptides, and the recombinant methods for producing the same. Also provided are diagnostic methods for detecting disorders related to the immune system, and therapeutic methods for treating such disorders. The invention further relates to screening methods for identifying agonists and antagonists of D-SLAM activity.

BACKGROUND OF THE INVENTION

A member of the immunoglobulin gene superfamily, SLAM is rapidly induced after activation of naive T- and B-cells. (Cocks, B. G., "A Novel Receptor Involved in T-Cell Activation," Nature 376:260–263 (1995); Aversa, G., "Engagement of the Signaling Lymphocytic Activation Molecule (SLAM) on Activated T Cells Results in Il-2-Independent, Cyclosporin A-Sensitive T Cell Proliferation and IFN-γ Production," J. Immun. 4036–4044 (1997).) A multifunctional 70 kDa glycoprotein, SLAM causes proliferation and differentiation of immune cells. (Punnonen, J., "Soluble and Membrane-bound Forms of Signaling Lymphocytic Activation Molecule (SLAM) Induce Proliferation and Ig Synthesis by Activated Human B Lymphocytes," J. Exp. Med. 185:993–1004 (1997).) To elicit an immune response, both a secreted form of SLAM, as well as a membrane bounded SLAM, are thought to interact.

It is also known that dendritic cells (DC) are the principal antigen presenting cells involved in primary immune responses; their major function is to obtain antigen in tissues, migrate to lymphoid organs, and activate T cells. (Mohamadzadeh, M. et al., J. Immunol. 156:3102–3106 (1996).) In fact, DC are usually the first immune cells to arrive at sites of inflammation on mucous membranes. (See, e.g., Weissman, D. et al., J. Immunol. 155:4111–4117 (1995).) There is a constant need to identify new polypeptide factors which may mediate interactions between DC and T cells, leading to the activation and/or proliferation of immune cells. To date, however, SLAM molecules have not been identified on DC cells.

Thus, there is a need for polypeptides that affect the proliferation, activation, survival, and/or differentiation of immune cells, such as T- and B-cells, since disturbances of such regulation may be involved in disorders relating to immune system. Therefore, there is a need for identification and characterization of such human polypeptides which can play a role in detecting, preventing, ameliorating or correcting such disorders.

SUMMARY OF THE INVENTION

The present invention relates to a novel polynucleotide and the encoded polypeptide of D-SLAM. Moreover, the present invention relates to vectors, host cells, antibodies, and recombinant methods for producing the polypeptides and polynucleotides. Also provided are diagnostic methods for detecting disorders relates to the polypeptides, and therapeutic methods for treating such disorders. The invention further relates to screening methods for identifying binding partners of D-SLAM.

BRIEF DESCRIPTION OF THE DRAWINGS

FIGS. 1A–1D show the nucleotide sequence (SEQ ID NO:1) and the deduced amino acid sequence (SEQ ID NO:2) of D-SLAM. The predicted leader sequence located at about amino acids 1–22 is underlined.

FIG. 2 shows the regions of identity between the amino acid sequence of the D-SLAM protein and the translation product of the human SLAM (Accession No. gi/984969) (SEQ ID NO:3), determined by BLAST analysis. Identical amino acids between the two polypeptides are shaded, while conservative amino acid are boxed. By examining the regions of amino acids shaded and/or boxed, the skilled artisan can readily identify conserved domains between the two polypeptides. These conserved domains are preferred embodiments of the present invention.

Figure 3:
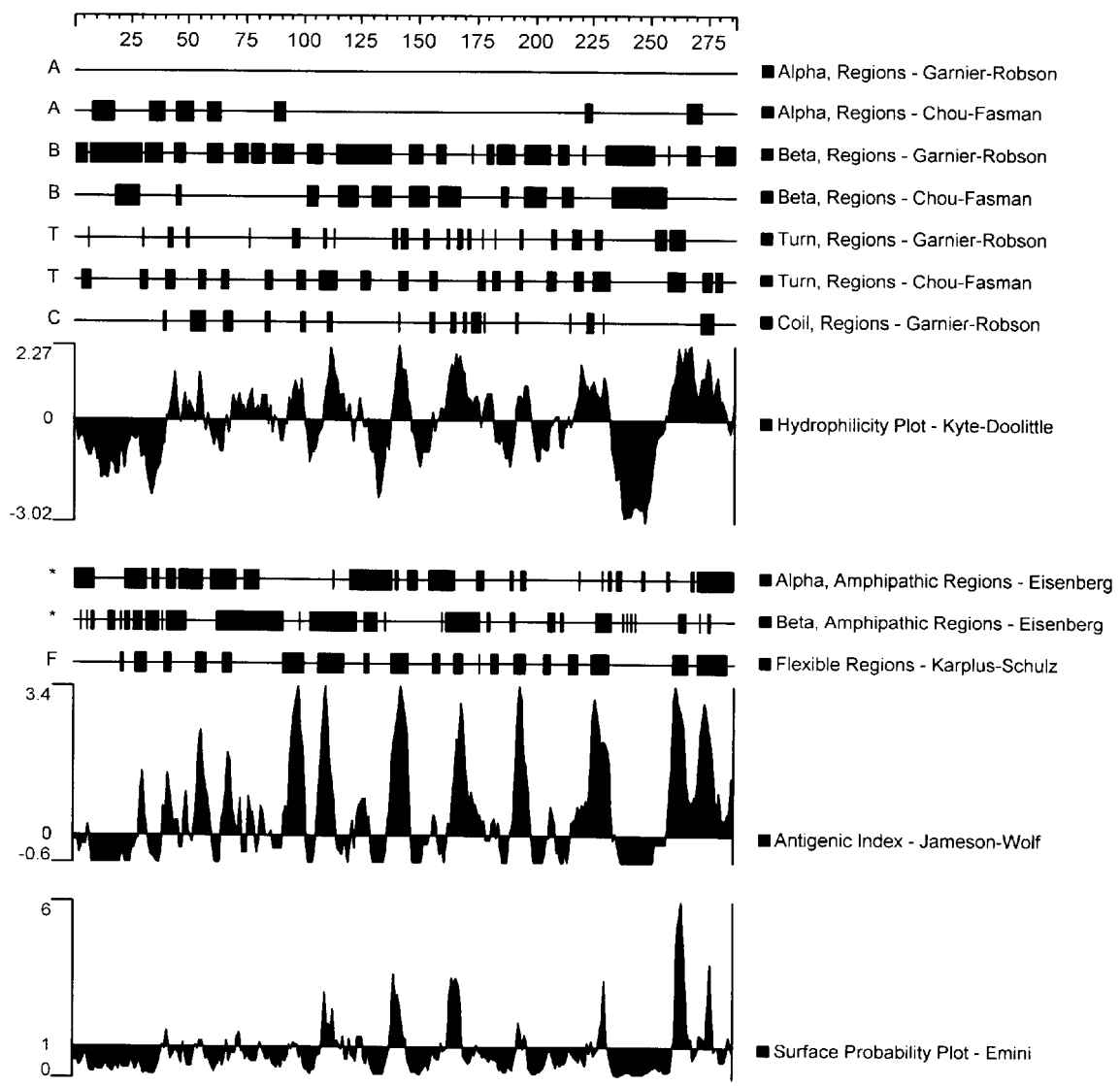
FIG. 3 shows an analysis of the D-SLAM amino acid sequence. Alpha, beta, turn and coil regions; hydrophilicity and hydrophobicity; amphipathic regions; flexible regions; antigenic index and surface probability are shown, and all were generated using the default settings. In the "Antigenic Index or Jameson-Wolf" graph, the positive peaks indicate locations of the highly antigenic regions of the D-SLAM protein, i.e., regions from which epitope-bearing peptides of the invention can be obtained. The domains defined by these graphs are contemplated by the present invention. Tabular representation of the data summarized graphically in FIG. 3 can be found in Table 1.

The columns are labeled with the headings "Res", "Position", and Roman Numerals I–XIV. The column headings refer to the following features of the amino acid sequence presented in FIG. 3, and Table I: "Res": amino acid residue of SEQ ID NO:2 and FIGS. 1A and 1B; "Position": position of the corresponding residue within SEQ ID NO:2 and FIGS. 1A and 1B; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" D-SLAM protein refers to a protein capable of being directed to the ER, secretory vesicles, or the extracellular space as a result of a signal sequence, as well as a D-SLAM protein released into the extracellular space without necessarily containing a signal sequence. If the D-SLAM secreted protein is released into the extracellular space, the D-SLAM secreted protein can undergo extracellular processing to produce a "mature" D-SLAM protein. Release into the extracellular space can occur by many mechanisms, including exocytosis and proteolytic cleavage.

As used herein, a D-SLAM "polynucleotide" refers to a molecule having a nucleic acid sequence contained in SEQ ID NO:1 or the cDNA contained within the clone deposited with the ATCC. For example, the D-SLAM polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a D-SLAM "polypeptide" refers to a molecule having the translated amino acid sequence generated from the polynucleotide as broadly defined.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of D-SLAM coding sequence, but do not comprise all or a portion of any D-SLAM intron. In another embodiment, the nucleic acid comprising D-SLAM coding sequence does not contain coding sequences of a genomic flanking gene (i.e., 5' or 3' to the D-SLAM gene in the genome).

In the present invention, the full length D-SLAM sequence identified as SEQ ID NO:1 was generated by overlapping sequences of the deposited clone (contig analysis). A representative clone containing all or most of the sequence for SEQ ID NO:1 was deposited with the American Type Culture Collection ("ATCC") on Feb. 6, 1998, and was given the ATCC Deposit Number 209623. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A D-SLAM "polynucleotide" also includes those polynucleotides capable of hybridizing, under stringent hybridization conditions, to sequences contained in SEQ ID NO:1, the complement thereof, or the cDNA within the deposited clone. "Stringent hybridization conditions" refers to an overnight incubation at 42 degree C. in a solution comprising 50% formamide, 5× SSC (750 mM NaCl, 75 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1× SSC at about 65 degree C.

Also contemplated are nucleic acid molecules that hybridize to the D-SLAM polynucleotides at moderatetly high stringency hybridization conditions. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37 degree C. in a solution comprising 6× SSPE (20× SSPE=3M NaCl; 0.2M NaH$_2$PO$_4$; 0.02M EDTA, pH 7.4), 0.5% SDS, 30% formamide, 100 ug/ml salmon sperm blocking DNA; followed by washes at 50 degree C. with 1XSSPE, 0.1% SDS. In addition, to achieve even lower stringency, washes performed following stringent hybridization can be done at higher salt concentrations (e.g. 5× SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The D-SLAM polynucleotide can be composed of any polyribonucleotide or polydeoxribonucleotide, which may be unmodified RNA or DNA or modified RNA or DNA. For example, D-SLAM polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the D-SLAM polynucleotides can be composed of triple-stranded regions comprising RNA or DNA or both RNA and DNA. D-SLAM polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

D-SLAM polypeptides can be composed of amino acids joined to each other by peptide bonds or modified peptide bonds, i.e., peptide isosteres, and may contain amino acids other than the 20 gene-encoded amino acids. The D-SLAM polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the D-SLAM polypeptide, including the peptide backbone, the amino acid side-chains and the amino or carboxyl termini. It will be appreciated that the same type of modification may be present in the same or varying degrees at several sites in a given D-SLAM polypeptide. Also, a given D-SLAM polypeptide may contain many types of modifications. D-SLAM polypeptides may be branched, for example, as a result of ubiquitination, and they may be cyclic, with or without branching. Cyclic, branched, and branched cyclic D-SLAM polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:1" refers to a D-SLAM polynucleotide sequence while "SEQ ID NO:2" refers to a D-SLAM polypeptide sequence.

A D-SLAM polypeptide "having biological activity" refers to polypeptides exhibiting activity similar, but not necessarily identical to, an activity of a D-SLAM polypeptide, including mature forms, as measured in a particular biological assay, with or without dose dependency. In the case where dose dependency does exist, it need not be identical to that of the D-SLAM polypeptide, but rather substantially similar to the dose-dependence in a given activity as compared to the D-SLAM polypeptide (i.e., the candidate polypeptide will exhibit greater activity or not more than about 25-fold less and, preferably, not more than about tenfold less activity, and most preferably, not more than about three-fold less activity relative to the D-SLAM polypeptide.)

D-SLAM Polynucleotides and Polypeptides

Clone HDPJO39 was isolated from a dendritic cell cDNA library. This clone contains the entire coding region identified as SEQ ID NO:2. The deposited clone contains a cDNA having a total of 3220 nucleotides, which encodes a predicted open reading frame of 285 amino acid residues. (See FIGS. 1A–1D.) The open reading frame begins at a N-terminal methionine located at nucleotide position 92, and ends at a stop codon at nucleotide position 947. The predicted molecular weight of the D-SLAM protein should be about 34.2 kDa.

Subsequent Northern analysis also showed D-SLAM expression in dendritic cells, T cell lymphoma, lymph node, spleen, thymus, small intestine, and uterus tissues, a pattern consistent with hematopoietic specific expression. Expression is highest in tissues involved in immune recognition, consistent with the enriched expression in dendritic cells and APC's. A single primary transcript of approximately 3.5–4.0 kb is observed, with a minor transcript of 7–9 kb that likely represents an unprocessed RNA precursor. The expression of the major 3.5–4 kb transcript is highest in lymph node, spleen, thymus, and, to a lesser degree, in small intestine. The highest expression of the 7–9 kb transcript is observed in the uterus.

Using BLAST analysis, SEQ ID NO:2 was found to be homologous to members of the Secreted Lymphocyte Activation Molecule (SLAM) family. Particularly, SEQ ID NO:2 contains domains homologous to the translation product of the human mRNA for SLAM (Accession No. gi/984969) (FIG. 2) (SEQ ID NO:3), including the following conserved domains: (a) a predicted transmembrane domain located at about amino acids 233–255; (b) a predicted extracellular domain located at about amino acids 23–232; and (c) a predicted intracellular domain located at about amino acids 256–285. These polypeptide fragments of D-SLAM are specifically contemplated in the present invention. Because SLAM (Accession No. gi/984969) is thought to be important in the activation and proliferation of T- and B-cells, the homology between SLAM (Accession No. gi/984969) and D-SLAM suggests that D-SLAM may also be involved in the activation and proliferation of T- and B-cells.

Moreover, the encoded polypeptide has a predicted leader sequence located at about amino acids 1–22. (See FIGS. 1A–1D.) Also shown in FIGS. 1A–1D, the predicted secreted form of D-SLAM encompasses about amino acids 23–232. These polypeptide fragments of D-SLAM are specifically contemplated in the present invention.

The D-SLAM nucleotide sequence identified as SEQ ID NO:1 was assembled from partially homologous ("overlapping") sequences obtained from the deposited clone, and in some cases, from additional related DNA clones. The overlapping sequences were assembled into a single contiguous sequence of high redundancy (usually three to five overlapping sequences at each nucleotide position), resulting in a final sequence identified as SEQ ID NO:1.

Therefore, SEQ ID NO:1 and the translated SEQ ID NO:2 are sufficiently accurate and otherwise suitable for a variety of uses well known in the art and described further below. For instance, SEQ ID NO:1 is useful for designing nucleic acid hybridization probes that will detect nucleic acid sequences contained in SEQ ID NO:1 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:2 may be used to generate antibodies which bind specifically to D-SLAM.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1 and the predicted translated amino acid sequence identified as SEQ ID NO:2, but also a sample of plasmid DNA containing a human cDNA of D-SLAM deposited with the ATCC. The nucleotide sequence of the deposited D-SLAM clone can readily be determined by sequencing the deposited clone in accordance with known methods. The predicted D-SLAM amino acid sequence can then be verified from such deposits. Moreover, the amino acid sequence of the protein encoded by the deposited clone can also be directly determined by peptide sequencing or by expressing the protein in a suitable host cell containing the deposited human D-SLAM cDNA, collecting the protein, and determining its sequence.

The present invention also relates to the D-SLAM gene corresponding to SEQ ID NO:1, SEQ ID NO:2, or the deposited clone. The D-SLAM gene can be isolated in accordance with known methods using the sequence information disclosed herein. Such methods include preparing probes or primers from the disclosed sequence and identifying or amplifying the D-SLAM gene from appropriate sources of genomic material.

Also provided in the present invention are species homologs of D-SLAM. Species homologs may be isolated and identified by making suitable probes or primers from the sequences provided herein and screening a suitable nucleic acid source for the desired homologue.

The D-SLAM polypeptides can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The D-SLAM polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

D-SLAM polypeptides are preferably provided in an isolated form, and preferably are substantially purified. A recombinantly produced version of a D-SLAM polypeptide, including the secreted polypeptide, can be substantially purified by the one-step method described in Smith and Johnson, Gene 67:31–40 (1988). D-SLAM polypeptides also can be purified from natural or recombinant sources using antibodies of the invention raised against the D-SLAM protein in methods which are well known in the art.

Polynucleotide and Polypeptide Variants

"Variant" refers to a polynucleotide or polypeptide differing from the D-SLAM polynucleotide or polypeptide, but retaining essential properties thereof. Generally, variants are overall closely similar, and, in many regions, identical to the D-SLAM polynucleotide or polypeptide.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the D-SLAM polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of SEQ ID NO:1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in SEQ ID NO:2 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The D-SLAM variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. D-SLAM polynucleotide variants can be produced for a variety of reasons, e.g., to optimize codon expression for a particular host (change codons in the human mRNA to those preferred by a bacterial host such as $E.\ coli$).

Naturally occurring D-SLAM variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the D-SLAM polypeptides. For instance, one or more amino acids can be deleted from the N-terminus or C-terminus of the secreted protein without substantial loss of biological function. The authors of Ron et al., J. Biol. Chem. 268:2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem. 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes D-SLAM polypeptide variants which show substantial biological activity. Such variants include deletions, insertions, inversions, repeats, and substitutions selected according to general rules known in the art so as have little effect on activity.

The present application is directed to nucleic acid molecules at least 90%, 95%, 96%, 97%, 98% or 99% identical to the nucleic acid sequences disclosed herein, (e.g., encoding a polypeptide having the amino acid sequence of an N and/or C terminal deletion disclosed below as m–n of SEQ ID NO:2), irrespective of whether they encode a polypeptide having D-SLAM functional activity. This is because even where a particular nucleic acid molecule does not encode a polypeptide having D-SLAM functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having D-SLAM functional activity include, inter alia, (1) isolating a D-SLAM gene or allelic or splice variants thereof in a cDNA library; (2) in situ hybridization (e.g., "FISH") to metaphase chromosomal spreads to provide precise chromosomal location of the D-SLAM gene, as described in Verma et al., Human Chromosomes: A Manual of Basic Techniques, Pergamon Press, New York (1988); and (3) Northern Blot analysis for detecting D-SLAM mRNA expression in specific tissues.

Preferred, however, are nucleic acid molecules having sequences at least 90%, 95%, 96%, 97%, 98% or 99% identical to the nucleic acid sequences disclosed herein, which do, in fact, encode a polypeptide having D-SLAM functional activity. By "a polypeptide having D-SLAM functional activity" is intended polypeptides exhibiting activity similar, but not necessarily identical, to a functional activity of the D-SLAM polypeptides of the present invention (e.g., complete (full-length) D-SLAM, mature D-SLAM and soluble D-SLAM (e.g., having sequences contained in the extracellular domain of D-SLAM) as measured, for example, in a particular immunoassay or biological assay. For example, a D-SLAM functional activity can routinely be measured by determining the ability of a D-SLAM polypeptide to bind a D-SLAM ligand. D-SLAM functional activity may also be measured by determining the ability of a polypeptide, such as cognate ligand which is free or expressed on a cell surface, to induce cells expressing the polypeptide.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA, the nucleic acid sequence shown in FIG. 1 (SEQ ID NO:1), or fragments thereof, will encode polypeptides "having D-SLAM functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having D-SLAM functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change. The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

For example, site directed changes at the amino acid level of D-SLAM can be made by replacing a particular amino acid with a conservative amino acid. Preferred conservative mutations include: M1 replaced with A, G, I, L, S, T, or V; V2 replaced with A, G, I, L, S, T, or M; M3 replaced with A, G, I, L, S, T, or V; R4 replaced with H, or K; L6 replaced with A, G, I, S, T, M, or V; W7 replaced with F, or Y; S8 replaced with A, G, I, L, T, M, or V; L9 replaced with A, G, I, S, T, M, or V; L10 replaced with A, G, I, S, T, M, or V; L11 replaced with A, G, I, S, T, M, or V; W12 replaced with F, or Y; E13 replaced with D; A14 replaced with G, I, L, S, T, M, or V; L15 replaced with A, G, I, S, T, M, or V; L16 replaced with A, G, I, S, T, M, or V; I18 replaced with A, G, L, S, T, M, or V; T19 replaced with A, G, I, L, S, M, or V; V20 replaced with A, G, I, L, S, T, or M; T21 replaced with A, G, I, L, S, M, or V; G22 replaced with A, I, L, S, T, M, or V; A23 replaced with G, I, L, S, T, M, or V; Q24 replaced with N; V25 replaced with A, G, I, L, S, T, or M; L26 replaced with A, G, I, S, T, M, or V; S27 replaced with A, G, I, L, T, M, or V; K28 replaced with H, or R; V29 replaced with A, G, I, L, S, T, or M; G30 replaced with A, I, L, S, T, M, or V; G31 replaced with A, I, L, S, T, M, or V; S32 replaced with A, G, I, L, T, M, or V; V33 replaced with A, G, I, L, S, T, or M; L34 replaced with A, G, I, S, T, M, or V; L35 replaced with A, G, I, S, T, M, or V; V36 replaced with A, G, I, L, S, T, or M; A37 replaced with G, I, L, S, T, M, or V; A38 replaced with G, I, L, S, T, M, or V; R39 replaced with H, or K; G42 replaced with A, I, L, S, T, M, or V; F43 replaced with W, or Y; Q44 replaced with N; V45 replaced with A, G, I, L, S, T, or M; R46 replaced with H, or K; E47 replaced with D; A48 replaced with G, I, L, S, T, M, or V; I49 replaced with A, G, L, S, T, M, or V; W50 replaced with F, or Y; R51 replaced with H, or K; S52 replaced with A, G, I, L, T, M, or V; L53 replaced with A, G, I, S, T, M, or V; W54 replaced with F, or Y; S56 replaced with A, G, I, L, T, M, or V; E57 replaced with D; E58 replaced with D; L59 replaced with A, G, I, S, T, M, or V; L60 replaced with A, G, I, S, T, M, or V; A61 replaced with G, I, L, S, T, M, or V; T62 replaced with A, G, I, L, S, M, or V; F63 replaced with W, or Y; F64 replaced with W, or Y; R65 replaced with H, or K; G66 replaced with A, I, L, S, T, M, or V; S67 replaced with A, G, I, L, T, M, or V; L68 replaced with A, G, I, S, T, M, or V; E69 replaced with D; T70 replaced with A, G, I, L, S, M, or V; L71 replaced with A, G, I, S, T, M, or V; Y72 replaced with F, or W; H73 replaced with K, or R; S74 replaced with A, G, I, L, T, M, or V; R75 replaced with H, or K; F76 replaced with W, or Y; L77 replaced with A, G, I, S, T, M, or V; G78 replaced with A, I, L, S, T, M, or V; R79 replaced with H, or K; A80 replaced with G, I, L, S, T, M, or V; Q81 replaced with N; L82 replaced with A, G, I, S, T, M, or V; H83 replaced with K, or R; S84 replaced with A, G, I, L, T, M, or V; N85 replaced with Q; L86 replaced with A, G, I, S, T, M, or V; S87 replaced with A, G, I, L, T, M, or V; L88 replaced with A, G, I, S, T, M, or V; E89 replaced with D; L90 replaced with A, G, I, S, T, M, or V; G91 replaced with A, I, L, S, T, M, or V; L93 replaced with A, G, I, S, T, M, or V; E94 replaced with D; S95 replaced with A, G, I, L, T, M, or V; G96 replaced with A, I, L, S, T, M, or V; D97 replaced with E; S98 replaced with A, G, I, L, T, M, or V; G99 replaced with A, I, L, S, T, M, or V; N100 replaced with Q; F101 replaced with W, or Y; S102 replaced with A, G, I, L, T, M, or V; V103 replaced with A, G, I, L, S, T, or M; L104 replaced with A, G, I, S, T, M, or V; M105 replaced with A, G, I, L, S, T, or V; V106 replaced with A, G, I, L, S, T, or M; D107 replaced with E; T108 replaced with A, G, I, L, S, M, or V; R109 replaced with H, or K; G110 replaced with A, I, L, S, T, M, or V; Q111 replaced with N; W113 replaced with F, or Y; T114 replaced with A, G, I, L, S, M, or V; Q115 replaced with N; T116 replaced with A, G, I, L, S, M, or V; L117 replaced with A, G, I, S, T, M, or V; Q118 replaced with N; L119 replaced with A, G, I, S, T, M, or V; K120 replaced with H, or R; V121 replaced with A, G, I, L, S, T, or M; Y122 replaced with F, or W; D123 replaced with E; A124 replaced with G, I, L, S, T, M, or V; V125 replaced with A, G, I, L, S, T, or M; R127 replaced with H, or K; V129 replaced with A, G, I, L, S, T, or M; V130 replaced with A, G, I, L, S, T, or M; Q131 replaced with N; V132 replaced with A, G, I, L, S, T, or M; F133 replaced with W, or Y; I134 replaced with A, G, L, S, T, M, or V; A135 replaced with G, I, L, S, T, M, or V; V136 replaced with A, G, I, L, S, T, or M; E137 replaced with D; R138 replaced with H, or K; D139 replaced with E; A140 replaced with G, I, L, S, T, M, or V; Q141 replaced with N; S143 replaced with A, G, I, L, T, M, or V; K144 replaced with H, or R; T145 replaced with A, G, I, L, S, M, or V; Q147 replaced with N; V148 replaced with A, G, I, L, S, T, or M; F149 replaced with W, or Y; L150 replaced with A, G, I, S, T, M, or V; S151 replaced with A, G, I, L, T, M, or V; W153 replaced with F, or Y; A154 replaced with G, I, L, S, T, M, or V; N156 replaced with Q; I157 replaced with A, G, L, S, T, M, or V; S158 replaced with A, G, I, L, T, M, or V; E159 replaced with D; I160 replaced with A, G, L, S, T, M, or V; T161 replaced with A, G, I, L, S, M, or V; Y162 replaced with F, or W; S163 replaced with A, G, I, L, T, M, or V; W164 replaced with F, or Y; R165 replaced with H, or K; R166 replaced with H, or K; E167 replaced with D; T168 replaced with A, G, I, L, S, M, or V; T169 replaced with A, G, I, L, S, M, or V; M170 replaced with A, G, I, L, S, T, or V; D171 replaced with E; F172 replaced with W, or Y; G173 replaced with A, I, L, S, T, M, or V; M174 replaced with A, G, I, L, S, T, or V; E175 replaced with D; H177 replaced with K, or R; S178 replaced with A, G, I, L, T, M, or V; L179 replaced with A, G, I, S, T, M, or V; F180 replaced with W, or Y; T181 replaced with A, G, I, L, S, M, or V; D182 replaced with E; G183 replaced with A, I, L, S, T, M, or V; Q184 replaced with N; V185 replaced with A, G, I, L, S, T, or M; L186 replaced with A, G, I, S, T, M, or V; S187 replaced with A, G, I, L, T, M, or V; I188 replaced with A, G, L, S, T, M, or V; S189 replaced with A, G, I, L, T, M, or V; L190 replaced with A, G, I, S, T, M, or V; G191 replaced with A, I, L, S, T, M, or V; G193 replaced with A, I, L, S, T, M, or V; D194 replaced with E; R195 replaced with H, or K; D196 replaced with E; V197 replaced with A, G, I, L, S, T, or M; A198 replaced with G, I, L, S, T, M, or V; Y199 replaced with F, or W; S200 replaced with A, G, I, L, T, M, or V; I202 replaced with A, G, L, S, T, M, or V; V203 replaced with A, G, I, L, S, T, or M; S204 replaced with A, G, I, L, T, M, or V; N205 replaced with Q; V207 replaced with A, G, I, L, S, T, or M; S208 replaced with A, G, I, L, T, M, or V; W209 replaced with F, or Y; D210 replaced with E; L211 replaced with A, G, I, S, T, M, or V; A212 replaced with G, I, L, S, T, M, or V; T213 replaced with A, G, I, L, S, M, or V; V214 replaced with A, G, I, L, S, T, or M; T215 replaced with A, G, I, L, S, M, or V; W217 replaced with F, or Y; D218 replaced with E; S219 replaced with A, G, I, L, T, M, or V; H221 replaced with K, or R; H222 replaced with K, or R; E223 replaced with D; A224 replaced with G, I, L, S, T, M, or V; A225 replaced with G, I, L, S, T, M, or V; G227 replaced with A, I, L, S, T, M, or V; K228 replaced with H, or R; A229 replaced with G, I, L, S, T, M, or V; S230 replaced with A, G, I, L, T, M, or V; Y231 replaced with F, or W; K232 replaced with H, or R; D233 replaced with E; V234 replaced with A, G, I, L, S, T, or M; L235 replaced with A, G, I, S, T, M, or V; L236 replaced with A, G, I, S, T, M, or V; V237 replaced with A, G, I, L, S, T, or M; V238 replaced with A, G, I, L, S, T, or M; V239 replaced with A, G, I, L, S, T, or M; V241 replaced with A, G, I, L, S, T, or M; S242 replaced with A, G, I, L, T, M, or V; L243 replaced with A, G, I, S, T, M, or V; L244 replaced with A, G, I, S, T, M, or V; L245 replaced with A, G, I, S, T, M, or V; M246 replaced with A, G, I, L, S, T, or V; L247 replaced with A, G, I, S, T, M, or V; V248 replaced with A, G, I, L, S, T, or M; T249 replaced with A, G, I, L, S, M, or V; L250 replaced with A, G, I, S, T, M, or V; F251 replaced with W, or Y; S252 replaced with A, G, I, L, T, M, or V; A253 replaced with G, I, L, S, T, M, or V; W254 replaced with F, or Y; H255 replaced with K, or R; W256 replaced with F, or Y; S260 replaced with A, G, I, L, T, M, or V; G261 replaced with A, I, L, S, T, M, or V; K262 replaced with H, or R; K263 replaced with H, or R; K264 replaced with H, or R; K265 replaced with H, or R; D266 replaced with E; V267 replaced with A, G, I, L, S, T, or M; H268 replaced with K, or R; A269 replaced with G, I, L, S, T, M, or V; D270 replaced with E; R271 replaced with H, or K; V272 replaced with A, G, I, L, S, T, or M; G273 replaced with A, I, L, S, T, M, or V; E275 replaced with D; T276 replaced with A, G, I, L, S, M, or V; E277 replaced with D; N278 replaced with Q; L280 replaced with A, G, I, S, T, M, or V; V281 replaced with A, G, I, L, S, T, or M; Q282 replaced with N; D283 replaced with E; L284 replaced with A, G, I, S, T, M, or V.

The resulting constructs can be routinely screened for activities or functions described throughout the specification and known in the art. Preferably, the resulting constructs have an increased D-SLAM activity or function, while the remaining D-SLAM activities or functions are maintained. More preferably, the resulting constructs have more than one increased D-SLAM activity or function, while the remaining D-SLAM activities or functions are maintained.

Besides conservative amino acid substitution, variants of D-SLAM include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, D-SLAM polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36:838–845 (1987); Cleland et al., Crit. Rev. Therapeutic Drug Carrier Systems 10:307–377 (1993).)

For example, preferred non-conservative substitutions of D-SLAM include: M1 replaced with D, E, H, K, R, N, Q, F, W, Y, P, or C; V2 replaced with D, E, H, K, R, N, Q, F, W, Y, P, or C; M3 replaced with D, E, H, K, R, N, Q, F, W, Y, P, or C; R4 replaced with D, E, A, G, I, L, S, T, M, V, N, Q, F, W, Y, P, or C; P5 replaced with D, E, H, K, R, A, G, I, L, S, T, M, V, N, Q, F, W, Y, or C; L6 replaced with D, E, H, K, R, N, Q, F, W, Y, P, or C; W7 replaced with D, E, H, K, R, N, Q, A, G, I, L, S, T, M, V, P, or C; S8 replaced with D, E, H, K, R, N, Q, F, W, Y, P, or C; L9 replaced with D, E, H, K, R, N, Q, F, W, Y, P, or C; L10 replaced with D, E, H, K, R, N, Q, F, W, Y, P, or C; L11 replaced with D, E, H, K, R, N, Q, F, W, Y, P, or C; W12 replaced with D, E, H, K, R, N, Q, A, G, I, L, S, T, M, V, P, or C; E13 replaced with H, K, R, A, G, I, L, S, T, M, V, N, Q, F, W, Y, P, or C; A14 replaced with D, E, H, K, R, N, Q, F, W, Y, P, or C; L15 replaced with D, E, H, K, R, N, Q, F, W, Y, P, or C; L16 replaced with D, E, H, K, R, N, Q, F, W, Y, P, or C; P17 replaced with D, E, H, K, R, A, G, I, L, S, T, M, V, N, Q, F, W, Y, or C; I18 replaced with D, E, H, K, R, N, Q, F, W, Y, P, or C; T19 replaced with D, E, H, K, R, N, Q, F, W, Y, P, or C; V20 replaced with D, E, H, K, R, N, Q, F, W, Y, P, or C; T21 replaced with D, E, H, K, R, N, Q, F, W, Y, P, or C; G22 replaced with D, E, H, K, R, N, Q, F, W, Y, P, or C; A23 replaced with D, E, H, K, R, N, Q, F, W, Y, P, or C; Q24 replaced with D, E, H, K, R, A, G, I, L, S, T, M, V, F, W, Y, P, or C; V25 replaced with D, E, H, K, R, N, Q, F, W, Y, P, or C; L26 replaced with D, E, H, K, R, N, Q, F, W, Y, P, or C; S27 replaced with D, E, H, K, R, N, Q, F, W, Y, P, or C; K28 replaced with D, E, A, G, I, L, S, T, M, V, N, Q, F, W, Y, P, or C; V29 replaced with D, E, H, K, R, N, Q, F, W, Y, P, or C; G30 replaced with D, E, H, K, R, N, Q, F, W, Y, P, or C; G31 replaced with D, E, H, K, R, N, Q, F, W, Y, P, or C; S32 replaced with D, E, H, K, R, N, Q, F, W, Y, P, or C; V33 replaced with D, E, H, K, R, N, Q, F, W, Y, P, or C; L34 replaced with D, E, H, K, R, N, Q, F, W, Y, P, or C; L35 replaced with D, E, H, K, R, N, Q, F, W, Y, P, or C; V36 replaced with D, E, H, K, R, N, Q, F, W, Y, P, or C; A37 replaced with D, E, H, K, R, N, Q, F, W, Y, P, or C; A38 replaced with D, E, H, K, R, N, Q, F, W, Y, P, or C; R39 replaced with D, E, A, G, I, L, S, T, M, V, N, Q, F, W, Y, P, or C; P40 replaced with D, E, H, K, R, A, G, I, L, S, T, M, V, N, Q, F, W, Y, or C; P41 replaced with D, E, H, K, R, A, G, I, L, S, T, M, V, N, Q, F, W, Y, or C; G42 replaced with D, E, H, K, R, N, Q, F, W, Y, P, or C; F43 replaced with D, E, H, K, R, N, Q, A, G, I, L, S, T, M, V, P, or C; Q44 replaced with D, E, H, K, R, A, G, I, L, S, T, M, V, F, W, Y, P, or C; V45 replaced with D, E, H, K, R, N, Q, F, W, Y, P, or C; R46 replaced with D, E, A, G, I, L, S, T, M, V, N, Q, F, W, Y, P, or C; E47 replaced with H, K, R, A, G, I, L, S, T, M, V, N, Q, F, W, Y, P, or C; A48 replaced with D, E, H, K, R, N, Q, F, W, Y, P, or C; I49 replaced with D, E, H, K, R, N, Q, F, W, Y, P, or C; W50 replaced with D, E, H, K, R, N, Q, A, G, I, L, S, T, M, V, P, or C; R51 replaced with D, E, A, G, I, L, S, T, M, V, N, Q, F. W, Y, P, or C; S52 replaced with D, E, H, K, R, N, Q, F, W, Y, P, or C; L53 replaced with D, E, H, K, R, N, Q, F, W, Y, P, or C; W54 replaced with D, E, H, K, R, N, Q, A, G, I, L, S, T, M, V, P, or C; P55 replaced with D, E, H, K, R, A, G, I, L, S, T, M, V, N, Q, F, W, Y, or C; S56 replaced with D, E, H, K, R, N, Q, F, W, Y, P, or C; E57 replaced with H, K, R, A, G, I, L, S, T, M, V, N, Q, F, W, Y, P, or C; E58 replaced with H, K, R, A, G, I, L, S, T, M, V, N, Q, F, W, Y, P, or C; L59 replaced with D, E, H, K, R, N, Q, F, W, Y, P, or C; L60 replaced with D, E, H, K, R, N, Q, F, W, Y, P, or C; A61 replaced with D, E, H, K, R, N, Q, F, W, Y, P, or C; T62 replaced with D, E, H, K, R, N, Q, F, W, Y, P, or C; F63 replaced with D, E, H, K, R, N, Q, A, G, I, L, S, T, M, V, P, or C; F64 replaced with D, E, H, K, R, N, Q, A, G, I, L, S, T, M, V, P, or C; R65 replaced with D, E, A, G, I, L, S, T, M, V, N, Q, F, W, Y, P, or C; G66 replaced with D, E, H, K, R, N, Q, F, W, Y, P, or C; S67 replaced with D, E, H, K, R, N, Q, F, W, Y, P, or C; L68 replaced with D, E, H, K, R, N, Q, F, W, Y, P, or C; E69 replaced with H, K, R, A, G, I, L, S, T, M, V, N, Q, F, W, Y, P, or C; T70 replaced with D, E, H, K, R, N, Q, F, W, Y, P, or C; L71 replaced with D, E, H, K, R, N, Q, F, W, Y, P, or C; Y72 replaced with D, E, H, K, R, N, Q, A, G, I, L, S, T, M, V, P, or C; H73 replaced with D, E, A, G, I, L, S, T, M, V, N, Q, F, W, Y, P, or C; S74 replaced with D, E, H, K, R, N, Q, F, W, Y, P, or C; R75 replaced with D, E, A, G, I, L, S, T, M, V, N, Q, F, W, Y, P, or C; F76 replaced with D, E, H, K, R, N, Q, A, G, I, L, S, T, M, V, P, or C; L77 replaced with D, E, H, K, R, N, Q, F, W, Y, P, or C; G78 replaced with D, E, H, K, R, N, Q, F, W, Y, P, or C; R79 replaced with D, E, A, G, I, L, S, T, M, V, N, Q, F, W, Y, P, or C; A80 replaced with D, E, H, K, R, N, Q, F, W, Y, P, or C; Q81 replaced with D, E, H, K, R, A, G, I, L, S, T, M, V, F, W, Y, P, or C; L82 replaced with D, E, H, K, R, N, Q, F, W, Y, P, or C; H83 replaced with D, E, A, G, I, L, S, T, M, V, N, Q, F, W, Y, P, or C; S84 replaced with D, E, H, K, R, N, Q, F, W, Y, P, or C; N85 replaced with D, E, H, K, R, A, G, I, L, S, T, M, V, F, W, Y, P, or C; L86 replaced with D, E, H, K, R, N, Q, F, W, Y, P, or C; S87 replaced with D, E, H, K, R, N, Q, F, W, Y, P, or C; L88 replaced with D, E, H, K, R, N, Q, F, W, Y, P, or C; E89 replaced with H, K, R, A, G, I, L, S, T, M, V, N, Q, F, W, Y, P, or C; L90 replaced with D, E, H, K, R, N, Q, F, W, Y, P, or C; G91 replaced with D, E, H, K, R, N, Q, F, W, Y, P, or C; P92 replaced with D, E, H, K, R, A, G, I, L, S, T, M, V, N, Q, F, W, Y, or C; L93 replaced with D, E, H, K, R, N, Q, F, W, Y, P, or C; E94 replaced with H, K, R, A, G, I, L, S, T, M, V, N, Q, F, W, Y, P, or C; S95 replaced with D, E, H, K, R, N, Q, F, W, Y, P, or C; G96 replaced with D, E, H, K, R, N, Q, F, W, Y, P, or C; D97 replaced with H, K, R, A, G, I, L, S, T, M, V, N, Q, F, W, Y, P, or C; S98 replaced with D, E, H, K, R, N, Q, F, W, Y, P, or C; G99 replaced with D, E, H, K, R, N, Q, F, W, Y, P, or C; N100 replaced with D, E, H, K, R, A, G, I, L, S, T, M, V, F, W, Y, P, or C; F101 replaced with D, E, H, K, R, N, Q, A, G, I, L, S, T, M, V, P, or C; S102 replaced with D, E, H, K, R, N, Q, F, W, Y, P, or C; V103 replaced with D, E, H, K, R, N, Q, F, W, Y, P, or C; L104 replaced with D, E, H, K, R, N, Q, F, W, Y, P, or C; M105 replaced with D, E, H, K, R, N, Q, F, W, Y, P, or C; V106 replaced with D, E, H, K, R, N, Q, F, W, Y, P, or C; D107 replaced with H, K, R, A, G, I, L, S, T, M, V, N, Q, F, W, Y, P, or C; T108 replaced with D, E, H, K, R, N, Q, F, W, Y, P, or C; R109 replaced with D, E, A, G, I, L, S, T, M, V, N, Q, F, W, Y, P, or C; G110 replaced with D, E, H, K, R, N, Q, F, W, Y, P, or C; Q111 replaced with D, E, H, K, R, A, G, I, L, S, T, M, V, F, W, Y, P, or C; P112 replaced with D, E, H, K, R, A, G, I, L, S, T, M, V, N, Q, F, W, Y, or C; W113 replaced with D, E, H, K, R, N, Q, A, G, I, L, S, T, M, V, P, or C; T114 replaced with D, E, H, K, R, N, Q, F, W, Y, P, or C; Q115 replaced with D, E, H, K, R, A, G, I, L, S, T, M, V, F, W, Y, P, or C; T116 replaced with D, E, H, K, R, N, Q, F, W, Y, P, or C; L117 replaced with D, E, H, K, R, N, Q, F, W, Y, P, or C; Q118 replaced with D, E, H, K, R, A, G, I, L, S, T, M, V, F, W, Y, P, or C; L119 replaced with D, E, H, K, R, N, Q, F, W, Y, P, or C; K120 replaced with D, E, A, G, I, L, S, T, M, V, N, Q, F, W, Y, P, or C; V121 replaced with D, E, H, K, R, N, Q, F, W, Y, P, or C; Y122 replaced with D, E, H, K, R, N, Q, A, G, I, L, S, T, M, V, P, or C; D123 replaced with H, K, R, A, G, I, L, S, T, M, V, N, Q, F, W, Y, P, or C; A124 replaced with D, E, H, K, R, N, Q, F, W, Y, P, or C; V125 replaced with D, E, H, K, R, N, Q, F, W, Y, P, or C; P126 replaced with D, E, H, K, R, A, G, I, L, S, T, M, V, N, Q, F, W, Y, or C; R127 replaced with D, E, A, G, I, L, S, T, M, V, N, Q, F, W, Y, P, or C; P128 replaced with D, E, H, K, R, A, G, I, L, S, T, M, V, N, Q, F, W, Y, or C; V129 replaced with D, E, H, K, R, N, Q, F, W, Y, P, or C; V130 replaced with D, E, H, K, R, N, Q, F, W, Y, P, or C; Q131 replaced with D, E, H, K, R, A, G, I, L, S, T, M, V, F, W, Y, P, or C; V132 replaced with D, E, H, K, R, N, Q, F, W, Y, P, or C; F133 replaced with D, E, H, K, R, N, Q, A, G, I, L, S, T, M, V, P, or C; I134 replaced with D, E, H, K, R, N, Q, F, W, Y, P, or C; A135 replaced with D, E, H, K, R, N, Q, F, W, Y, P, or C; V136 replaced with D, E, H, K, R, N, Q, F, W, Y, P, or C; E137 replaced with H, K, R, A, G, I, L, S, T, M, V, N, Q, F, W, Y, P, or C; R138 replaced with D, E, A, G, I, L, S, T, M, V, N, Q, F, W, Y, P, or C; D139 replaced with H, K, R, A, G, I, L, S, T, M, V, N, Q, F, W, Y, P, or C; A140 replaced with D, E, H, K, R, N, Q, F, W, Y, P, or C; Q141 replaced with D, E, H, K, R, A, G, I, L, S, T, M, V, F, W, Y, P, or C; P142 replaced with D, E, H, K, R, A, G, I, L, S, T, M, V, N, Q, F, W, Y, or C; S143 replaced with D, E, H, K, R, N, Q, F, W, Y, P, or C; K144 replaced with D, E, A, G, I, L, S, T, M, V, N, Q, F, W, Y, P, or C; T145 replaced with D, E, H, K, R, N, Q, F, W, Y, P, or C; C146 replaced with D, E, H, K, R, A, G, I, L, S, T, M, V, N, Q, F, W, Y, or P; Q147 replaced with D, E, H, K, R, A, G, I, L, S, T, M, V, F, W, Y, P, or C; V148 replaced with D, E, H, K, R, N, Q, F, W, Y, P, or C; F149 replaced with D, E, H, K, R, N, Q, A, G, I, L, S, T, M, V, P, or C; L150 replaced with D, E, H, K, R, N, Q, F, W, Y, P, or C; S151 replaced with D, E, H, K, R, N, Q, F, W, Y, P, or C; C152 replaced with D, E, H, K, R, A, G, I, L, S, T, M, V, N, Q, F, W, Y, or P; W153 replaced with D, E, H, K, R, N, Q, A, G, I, L, S, T, M, V, P, or C; A154 replaced with D, E, H, K, R, N, Q, F, W, Y, P, or C; P155 replaced with D, E, H, K, R, A, G, I, L, S, T, M, V, N, Q, F, W, Y, or C; N156 replaced with D, E, H, K, R, A, G, I, L, S, T, M, V, F, W, Y, P, or C; I157 replaced with D, E, H, K, R, N, Q, F, W, Y, P, or C; S158 replaced with D, E, H, K, R, N, Q, F, W, Y, P, or C; E159 replaced with H, K, R, A, G, I, L, S, T, M, V, N, Q, F, W, Y, P, or C; I160 replaced with D, E, H, K, R, N, Q, F, W, Y, P, or C; T161 replaced with D, E, H, K, R, N, Q, F, W, Y, P, or C; Y162 replaced with D, E, H, K, R, N, Q, A, G, I, L. S, T, M, V, P, or C; S163 replaced with D, E, H, K, R, N, Q, F, W, Y, P, or C; W164 replaced with D, E, H, K, R, N, Q, A, G, I, L, S, T, M, V, P, or C; R165 replaced with D, E, A, G, I, L, S, T, M, V, N, Q, F, W, Y, P, or C; R166 replaced with D, E, A, G, I, L, S, T, M, V, N, Q, F, W, Y, P, or C; E167 replaced with H, K, R, A, G, I, L, S, T, M, V, N, Q, F, W, Y, P, or C; T168 replaced with D, E, H, K, R, N, Q, F, W, Y, P, or C; T169 replaced with D, E, H, K, R, N, Q, F, W, Y, P, or C; M170 replaced with D, E, H, K, R, N, Q, F, W, Y, P, or C; D171 replaced with H, K, R, A, G, I, L, S, T, M, V, N, Q, F, W, Y, P, or C; F172 replaced with D, E, H, K, R, N, Q, A, G, I, L, S, T, M, V, P, or C; G173 replaced with D, E, H, K, R, N, Q, F, W, Y, P, or C; M174 replaced with D, E, H, K, R, N, Q, F, W, Y, P, or C; E175 replaced with H, K, R, A, G, I, L, S, T, M, V, N, Q, F, W, Y, P, or C; P176 replaced with D, E, H, K, R, A, G, I, L, S, T, M, V, N, Q, F, W, Y, or C; H177 replaced with D, E, A, G, I, L, S, T, M, V, N, Q, F, W, Y, P, or C; S178 replaced with D, E, H, K, R, N, Q, F, W, Y, P, or C; L179 replaced with D, E, H, K, R, N, Q, F, W, Y, P, or C; F180 replaced with D, E, H, K, R, N, Q, A, G, I, L, S, T, M, V, P, or C; T181 replaced with D, E, H, K, R, N, Q, F, W, Y, P, or C; D182 replaced with H, K, R, A, G, I, L, S, T, M, V, N, Q, F, W, Y, P, or C; G183 replaced with D, E, H, K, R, N, Q, F, W, Y, P, or C; Q184 replaced with D, E, H, K, R, A, G, I, L, S, T, M, V, F, W, Y, P, or C; V185 replaced with D, E, H, K, R, N, Q, F, W, Y, P, or C; L186 replaced with D, E, H, K, R, N, Q, F, W, Y, P, or C; S187 replaced with D, E, H, K, R, N, Q, F, W, Y, P, or C; I188 replaced with D, E, H, K, R, N, Q, F, W, Y, P, or C; S189 replaced with D, E, H, K, R, N, Q, F, W, Y, P, or C; L190 replaced with D, E, H, K, R, N, Q, F, W, Y, P, or C; G191 replaced with D, E, H, K, R, N, Q, F, W, Y, P, or C; P192 replaced with D, E, H, K, R, A, G, I, L, S, T, M, V, N, Q, F, W, Y, or C; G193 replaced with D, E, H, K, R, N, Q, F, W, Y, P, or C; D194 replaced with H, K, R, A, G, I, L, S, T, M, V, N, Q, F, W, Y, P, or C; R195 replaced with D, E, A, G, I, L, S, T, M, V, N, Q, F, W, Y, P, or C; D196 replaced with H, K, R, A, G, I, L, S, T, M, V, N, Q, F, W, Y, P, or C; V197 replaced with D, E, H, K, R, N, Q, F, W, Y, P, or C; A198 replaced with D, E, H, K, R, N, Q, F, W, Y, P, or C; Y199 replaced with D, E, H, K, R, N, Q, A, G, I, L, S, T, M, V, P, or C; S200 replaced with D, E, H, K, R, N, Q, F, W, Y, P, or C; C201 replaced with D, E, H, K, R, A, G, I, L, S, T, M, V, N, Q, F, W, Y, or P; I202 replaced with D, E, H, K, R, N, Q, F, W, Y, P, or C; V203 replaced with D, E, H, K, R, N, Q, F, W, Y, P, or C; S204 replaced with D, E, H, K, R, N, Q. F, W, Y, P, or C; N205 replaced with D, E, H, K, R, A, G, I, L, S, T, M, V, F, W, Y, P, or C; P206 replaced with D, E, H, K, R, A, G, I, L, S, T, M, V, N, Q, F, W, Y, or C; V207 replaced with D, E, H, K, R, N, Q, F, W, Y, P, or C; S208 replaced with D, E, H, K, R, N, Q, F, W, Y, P, or C; W209 replaced with D, E, H, K, R, N, Q, A, G, I, L, S, T, M, V, P, or C; D210 replaced with H, K, R, A, G, I, L, S, T, M, V, N, Q, F, W, Y, P, or C; L211 replaced with D, E, H, K, R, N, Q, F, W, Y, P, or C; A212 replaced with D, E, H, K, R, N, Q, F, W, Y, P, or C; T213 replaced with D, E, H, K, R, N, Q, F, W, Y, P, or C; V214 replaced with D, E, H, K, R, N, Q, F, W, Y, P, or C; T215 replaced with D, E, H, K, R, N, Q, F, W, Y, P, or C; P216 replaced with D, E, H, K, R, A, G, I, L, S, T, M, V, N, Q, F, W, Y, or C; W217 replaced with D, E, H, K, R, N, Q, A, G, I, L, S, T, M, V, P, or C; D218 replaced with H, K, R, A, G, I, L, S, T, M, V, N, Q, F, W, Y, P, or C; S219 replaced with D, E, H, K, R, N, Q, F, W, Y, P, or C; C220 replaced with D, E, H, K, R, A, G, I, L, S, T, M, V, N, Q, F, W, Y, or P; H221 replaced with D, E, A, G, I, L, S, T, M, V, N, Q, F, W, Y, P, or C; H222 replaced with D, E, A, G, I, L, S, T, M, V, N, Q, F, W, Y, P, or C; E223 replaced with H, K, R, A, G, I, L, S, T, M, V, N, Q, F, W, Y, P, or C; A224 replaced with D, E, H, K, R, N, Q, F, W, Y, P, or C; A225 replaced with D, E, H, K, R, N, Q, F, W, Y, P, or C; P226 replaced with D, E, H, K, R, A, G, I, L, S, T, M, V, N, Q, F, W, Y, or C; G227 replaced with D, E, H, K, R, N, Q, F, W, Y, P, or C; K228 replaced with D, E, A, G, I, L, S, T, M, V, N, Q, F, W, Y, P, or C; A229 replaced with D, E, H, K, R, N, Q, F, W, Y, P, or C; S230 replaced with D, E, H, K, R, N, Q, F, W, Y, P, or C; Y231 replaced with D, E, H, K, R, N, Q, A, G, I, L, S, T, M, V, P, or C; K232 replaced with D, E, A, G, I, L, S, T, M, V, N, Q, F, W, Y, P, or C; D233 replaced with H, K, R, A, G, I, L, S, T, M, V, N, Q, F, W, Y, P, or C; V234 replaced with D, E, H, K, R, N, Q, F, W, Y, P, or C; L235 replaced with D, E, H, K, R, N, Q, F, W, Y, P, or C; L236 replaced with D, E, H, K, R, N, Q, F, W, Y, P, or C; V237 replaced with D, E, H, K, R, N, Q, F, W, Y, P, or C; V238 replaced with D, E, H, K, R, N, Q, F, W, Y, P, or C; V239 replaced with D, E, H, K, R, N, Q, F, W, Y, P, or C; P240 replaced with D, E, H, K, R, A, G, I, L, S, T, M, V, N, Q, F, W, Y, or C; V241 replaced with D, E, H, K, R, N, Q, F, W, Y, P, or C; S242 replaced with D, E, H, K, R, N, Q, F, W, Y, P, or C; L243 replaced with D, E, H, K, R, N, Q, F, W, Y, P, or C; L244 replaced with D, E, H, K, R, N, Q, F, W, Y, P, or C; L245 replaced with D, E, H, K, R, N, Q, F, W, Y, P, or C; M246 replaced with D, E, H, K, R, N, Q, F, W, Y, P, or C; L247 replaced with D, E, H, K, R, N, Q, F, W, Y, P, or C; V248 replaced with D, E, H, K, R, N, Q, F, W, Y, P, or C; T249 replaced with D, E, H, K, R, N, Q, F, W, Y, P, or C; L250 replaced with D, E, H, K, R, N, Q, F, W, Y, P, or C; F251 replaced with D, E, H, K, R, N, Q, A, G, I, L, S, T, M, V, P, or C; S252 replaced with D, E, H, K, R, N, Q, F, W, Y, P, or C; A253 replaced with D, E, H, K, R, N, Q, F, W, Y, P, or C; W254 replaced with D, E, H, K, R, N, Q, A, G, I, L, S, T, M, V, P, or C; H255 replaced with D, E, A, G, I, L, S, T, M, V, N, Q, F, W, Y, P, or C; W256 replaced with D, E, H, K, R, N, Q, A, G, I, L, S, T, M, V, P, or C; C257 replaced with D, E, H, K, R, A, G, I, L, S, T, M, V, N, Q, F, W, Y, or P; P258 replaced with D, E, H, K, R, A, G, I, L, S, T, M, V, N, Q, F, W, Y, or C; C259 replaced with D, E, H, K, R, A, G, I, L, S, T, M, V, N, Q, F, W, Y, or P; S260 replaced with D, E, H, K, R, N, Q, F, W, Y, P, or C; G261 replaced with D, E, H, K, R, N, Q, F, W, Y, P, or C; K262 replaced with D, E, A, G, I, L, S, T, M, V, N, Q, F, W, Y, P, or C; K263 replaced with D, E, A, G, I, L, S, T, M, V, N, Q, F, W, Y, P, or C; K264 replaced with D, E, A, G, I, L, S, T, M, V, N, Q, F, W, Y, P, or C; K265 replaced with D, E, A, G, I, L, S, T, M, V, N, Q, F, W, Y, P, or C; D266 replaced with H, K, R, A, G, I, L, S, T, M, V, N, Q, F, W, Y, P, or C; V267 replaced with D, E, H, K, R, N, Q, F, W, Y, P, or C; H268 replaced with D, E, A, G, I, L, S, T, M, V, N, Q, F, W, Y, P, or C; A269 replaced with D, E, H, K, R, N, Q, F, W, Y, P, or C; D270 replaced with H, K, R, A, G, I, L, S, T, M, V, N, Q, F, W, Y, P, or C; R271 replaced with D, E, A, G, I, L, S, T, M, V, N, Q, F, W, Y, P, or C; V272 replaced with D, E, H, K, R, N, Q, F, W, Y, P, or C; G273 replaced with D, E, H, K, R, N, Q, F, W, Y, P, or C; P274 replaced with D, E, H, K, R, A, G, I, L, S, T, M, V, N, Q, F, W, Y, or C; E275 replaced with H, K, R, A, G, I, L, S, T, M, V, N, Q, F, W, Y, P, or C; T276 replaced with D, E, H, K, R, N, Q, F, W, Y, P, or C; E277 replaced with H, K, R, A, G, I, L, S, T, M, V, N, Q, F, W, Y, P, or C; N278 replaced with D, E, H, K, R, A, G, I, L, S, T, M, V, F, W, Y, P, or C; P279 replaced with D, E, H, K, R, A, G, I, L, S, T, M, V, N, Q, F, W, Y, or C; L280 replaced with D, E, H, K, R, N, Q, F, W, Y, P, or C; V281 replaced with D, E, H, K, R, N, Q, F, W, Y, P, or C; Q282 replaced with D, E, H, K, R, A, G, I, L, S, T, M, V, F, W, Y, P, or C; D283 replaced with H, K, R, A, G, I, L, S, T, M, V, N, Q, F, W, Y, P, or C; L284 replaced with D, E, H, K, R, N, Q, F, W, Y, P, or C; P285 replaced with D, E, H, K, R, A, G, I, L, S, T, M, V, N, Q, F, W, Y, or C.

The resulting constructs can be routinely screened for activities or functions described throughout the specification and known in the art. Preferably, the resulting constructs have loss of a D-SLAM activity or function, while the remaining D-SLAM activities or functions are maintained. More preferably, the resulting constructs have more than one loss of D-SLAM activity or function, while the remaining D-SLAM activities or functions are maintained.

Additionally, more than one amino acid (e.g., 2, 3, 4, 5, 6, 7, 8, 9 and 10) can be replaced with the substituted amino acids as described above (either conservative or nonconservative).

A further embodiment of the invention relates to a polypeptide which comprises the amino acid sequence of a D-SLAM polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of a D-SLAM polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIGS. 1A–1D or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is further directed to fragments of the isolated nucleic acid molecules described herein. By a fragment of an isolated nucleic acid molecule having, for example, the nucleotide sequence of the deposited cDNA (clone HDPJO39), a nucleotide sequence encoding the polypeptide sequence encoded by the deposited cDNA, a nucleotide sequence encoding the polypeptide sequence depicted in FIG. 1 (SEQ ID NO:2), the nucleotide sequence shown in FIG. 1 (SEQ ID NO:1), or the complementary strand thereto, is intended fragments at least 15 nt, and more preferably at least about 20 nt, still more preferably at least 30 nt, and even more preferably, at l least about 40, 50, 100, 150, 200, 250, 300, 325, 350, 375, 400, 450, 500, 550, or 600 nt in length. These fragments have numerous uses that include, but are not limited to, diagnostic probes and primers as discussed herein. Of course, larger fragments, such as those of 501–1500 nt in length are also useful according to the present invention as are fragments corresponding to most, if not all, of the nucleotide sequences of the deposited cDNA (clone HDPJO39) or as shown in FIG. 1 (SEQ ID NO:1). By a fragment at least 20 nt in length, for example, is intended fragments which include 20 or more contiguous bases from, for example, the nucleotide sequence of the deposited cDNA, or the nucleotide sequence as shown in FIG. 1 (SEQ ID NO:1).

Moreover, representative examples of D-SLAM polynucleotide fragments include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, and/or 2001 to the end of SEQ ID NO:1 or the complementary strand thereto, or the cDNA contained in the deposited clone. In this context "about" includes the particularly recited ranges, larger or smaller by several (5, 4, 3, 2, or 1) nucleotides, at either terminus or at both termini.

Preferably, the polynucleotide fragments of the invention encode a polypeptide which demonstrates a D-SLAM functional activity. By a polypeptide demonstrating a D-SLAM "functional activity" is meant, a polypeptide capable of displaying one or more known functional activities associated with a full-length (complete) D-SLAM protein. Such functional activities include, but are not limited to, biological activity, antigenicity [ability to bind (or compete with a D-SLAM polypeptide for binding) to an anti-D-SLAM antibody], immunogenicity (ability to generate antibody which binds to a D-SLAM polypeptide), ability to form multimers with D-SLAM polypeptides of the invention, and ability to bind to a receptor or ligand for a D-SLAM polypeptide.

The functional activity of D-SLAM polypeptides, and fragments, variants derivatives, and analogs thereof, can be assayed by various methods.

For example, in one embodiment where one is assaying for the ability to bind or compete with full-length D-SLAM polypeptide for binding to anti-D-SLAM antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a D-SLAM ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94–123. In another embodiment, physiological correlates of D-SLAM binding to its substrates (signal transduction) can be assayed.

In addition, assays described herein (see Examples) and otherwise known in the art may routinely be applied to measure the ability of D-SLAM polypeptides and fragments, variants derivatives and analogs thereof to elicit D-SLAM related biological activity (either in vitro or in vivo). Other methods will be known to the skilled artisan and are within the scope of the invention.

The present invention is further directed to fragments of the D-SLAM polypeptide described herein. By a fragment of an isolated the D-SLAM polypeptide, for example, encoded by the deposited cDNA (clone HDPJO39), the polypeptide sequence encoded by the deposited cDNA, the polypeptide sequence depicted in FIG. 1 (SEQ ID NO:2), is intended to encompass polypeptide fragments contained in SEQ ID NO:2 or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, 161–180, 181–200, 201–220, 221–240, 241–260, 261–280, or 281 to the end of the coding region. Moreover, polypeptide fragments can be at least 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Even if deletion of one or more amino acids from the N-terminus of a protein results in modification of loss of one or more biological functions of the protein, other functional activities (e.g., biological activities, ability to multimerize, ability to bind D-SLAM ligand) may still be retained. For example, the ability of shortened D-SLAM muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an D-SLAM mutein with a large number of deleted N-terminal amino acid residues may retain some biological or immunogenic activities. In fact, peptides composed of as few as six D-SLAM amino acid residues may often evoke an immune response.

Accordingly, polypeptide fragments include the secreted D-SLAM protein as well as the mature form. Further preferred polypeptide fragments include the secreted D-SLAM protein or the mature form having a continuous series of deleted residues from the amino or the carboxy terminus, or both. For example, any number of amino acids, ranging from 1–60, can be deleted from the amino terminus of either the secreted D-SLAM polypeptide or the mature form. Similarly, any number of amino acids, ranging from 1–30, can be deleted from the carboxy terminus of the secreted D-SLAM protein or mature form. Furthermore, any combination of the above amino and carboxy terminus deletions are preferred. Similarly, polynucleotide fragments encoding these D-SLAM polypeptide fragments are also preferred.

Particularly, N-terminal deletions of the D-SLAM polypeptide can be described by the general formula m-285, where m is an integer from 2 to 284, where m corresponds to the position of the amino acid residue identified in SEQ ID NO:2. More in particular, the invention provides polynucleotides encoding polypeptides comprising, or alternatively consisting of, the amino acid sequence of residues of: V-2 to P-285; M-3 to P-285; R-4 to P-285; P-5 to P-285; L-6 to P-285; W-7 to P-285; S-8 to P-285; L-9 to P-285; L-10 to P-285; L-11 to P-285; W-12 to P-285; E-13 to P-285; A-14 to P-285; L-15 to P-285; L-16 to P-285; P-17 to P-285; I-18 to P-285; T-19 to P-285; V-520 to P-285; T-21 to P-285; G-22 to P-285. A-23 to P-285; Q-24 to P-285; V-25 to P-285; L-26 to P-285; S-27 to P-285; K-28 to P-285; V-29 to P-285;

G-30 to P-285; G-31 to P-285; S-32 to P-285; V-33 to P-285; L-34 to P-285; V-36 to P-285; A-37 to P-285; A-38 to P-285; R-39 to P-285; P-40 to P-285; P-41 to P-285; G-42 to P-285; F-43 to P-285; Q-44 to P-285; V-45 to P-285; R-46 to P-285; E-47 to P-285; A-48 to P-285; I-49 to P-285; W-50 to P-285; R-51 to P-285; S-52 to P-285; L-53 to P-285; W-54 to P-285; P-55 to P-285; S-56 to P-285; E-57 to P-285; E-58 to P-285; L-59 to P-285; L-60 to P-285; A-61 to P-285; T-62 to P-285; F-63 to P-285; F-64 to P-285; R-65 to P-285; G-66 to P-285; S-67 to P-285; L-68 to P-285; E-69 to P-285; T-70 to P-285; L-71 to P-285; Y-72 to P-285; H-73 to P-285; S-74 to P-285; R-75 to P-285; F-76 to P-285; L-77 to P-285; G-78 to P-285; R-79 to P-285; A-80 to P-285; Q-81 P-285; L-82 to P-285; H-83 to P-285; S-84 to P-285; N-85 to P-285; L-86 to P-285; S-87 to P-285; L-88 to P-285; E-89 to P-285; L-90 to P-285; G-91 to P-285; P-92 to P-285; L-93 to P-285; E-94 to P-285; S-95 to P-285; G-96 to P-285; D-97 to P-285; S-98 to P-285; G-99 to P-285; N-100 to P-285; F-101 to P-285; S-102 to P-285; V-103 to P-285; L-104 to P-285; M-105 to P-285; V-106 to P-285; D-107 to P-285; T-108 to P-285; R-109 to P-285; G-110 to P-285; Q-111 to P-285; P-112 to P-285; W-113 to P-285; T-114 to P-285; Q-115 to P-285; T-116 to P-285; L-117 to P-285; Q-118 to P-285; L-119 to P-285; K-120 to P-285; V-121 to P-285; Y-122 to P-285; D-123 to P-285; A-124 to P-285; V-125 to P-285; P-126 to P-285; R-127 to P-285; P-128 to P-285; V-129 to P-285; V-130 to P-285; Q-131 to P-285; V-132 to P-285; F-133 to P-285; I-134 to P-285; A-135 to P-285; V-136 to P-285; E-137 to P-285; R-138 to P-285; D-139 to P-285; A-140 to P-285; Q-141 to P-285; P-142 to P-285; S-143 to P-285; K-144 to P-285; T-145 to P-285; C-146 to P-285; Q-147 to P-285; V-148 to P-285; F-149 to P-285; L-150 to P-285; S-151 to P-285; C-152 to P-285; W-153 to P-285; A-154 to P-285; P-155 to P-285; N-156 to P-285; I-157 to P-285; S-158 to P-285; E-159 to P-285; I-160 to P-285; T-161 to P-285; Y-162 to P-285; S-163 to P-285; W-164 to P-285; R-165 to P-285; R-166 to P-285; E-167 to P-285; T-168 to P-285; T-169 to P-285; M-170 to P-285; D-171 to P-285; F-172 to P-285; G-173 to P-285; M-174 to P-285; E-175 to P-285; P-176 to P-285; H-177 to P-285; S-178 to P-285; L-179 to P-285; F-180 to P-285; T-181 to P-285; D-182 to P-285; G-183 to P-285; Q-184 to P-285; V-185 to P-285; L-186 to P-285; S-187 to P-285; I-188 to P-285; S-189 to P-285; L-190 to P-285; G-191 to P-285; P-192 to P-285; G-193 to P-285; D-194 to P-285; R-195 to P-285; D-196 to P-285; V-197 to P-285; A-198 to P-285; Y-199 to P-285; S-200 to P-285; C-201 to P-285; I-202 to P-285; V-203 to P-285; S-204 to P-285; N-205 to P-285; P-206 to P-285; V-207 to P-285; S-208 to P-285; W-209 to P-285; D-210 to P-285; L-211 to P-285; A-212 to P-285; T-213 to P-285; V-214 to P-285; T-215 to P-285; P-216 to P-285; W-217 to P-285; D-218 to P-285; S-219 to P-285; C-220 to P-285; H-221 to P-285; H-222 to P-285; E-223 to P-285; A-224 to P-285; A-225 to P-285; P-226 to P-285; G-227 to P-285; K-228 to P-285; A-229 to P-285; S-230 to P-285; Y-231 to P-285; K-232 to P-285; D-233 to P-285; V-234 to P-285; L-235 to P-285; L-236 to P-285; V-237 to P-285; V-238 to P-285; V-239 to P-285; P-240 to P-285; V-241 to P-285; S-242 to P-285; L-243 to P-285; L-244 to P-285; L-245 to P-285; M-246 to P-285; L-247 to P-285; V-248 to P-285; T-249 to P-285; L-250 to P-285; F-251 to P-285; S-252 to P-285; A-253 to P-285; W-254 to P-285; H-255 to P-285; W-256 to P-285; C-257 to P-285; P-258 to P-285; C-259 to P-285; S-260 to P-285; G-261 to P-285; K-262 to P-285; K-263 to P-285; K-264 to P-285; K-265 to P-285; D-266 to P-285; V-267 to P-285; H-268 to P-285; A-269 to P-285; D-270 to P-285; R-271 to P-285; V-272 to P-285; G-273 to P-285; P-274 to P-285; E-275 to P-285; T-276 to P-285; E-277 to P-285; N-278 to P-285; P-279 to P-285; L-280 to P-285; of SEQ ID NO:2. Polynucleotides encoding these polypeptides are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind D-SLAM ligand) may still be retained. For example the ability of the shortened D-SLAM mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an D-SLAM mutein with a large number of deleted C-terminal amino acid residues may retain some biological or imnnunogenic activities. In fact, peptides composed of as few as six D-SLAM amino acid residues may often evoke an immune response.

Accordingly, the present invention further provides polypeptides having one or more residues deleted from the carboxy terminus of the amino acid sequence of the D-SLAM polypeptide shown in FIG. 1 (SEQ ID NO:2), as described by the general formula 1-n, where n is an integer from 2 to 284, where n corresponds to the position of amino acid residue identified in SEQ ID NO:2. More in particular, the invention provides polynucleotides encoding polypeptides comprising, or alternatively consisting of, the amino acid sequence of residues of: M-1 to L-284; M-1 to D-283; M-1 to Q-282; M-1 to V-281; M-1 to L-280; M-1 to P-279; M-1 to N-278; M-1 to E-277; M-1 to T-276; M-1 to E-275; M-1 to P-274; M-1 to G-273; M-1 to V-272; M-1 to R-271; M-1 to D-270; M-1 to A-269; M-1 to H-268; M-1 to V-267; M-1 to D-266; M-1 to K-265; M-1 to K-264; M-1 to K-263; M-1 to K-262; M-1 to G-261; M-1 to S-260; M-1 to C-259; M-1 to P-258; M-1 to C-257; M-1 to W-256; M-1 to H-255; M-1 to W-254; M-1 to A-253; M-1 to S-252; M-1 to F-251; M-1 to L-250; M-1 to T-249; M-1 to V-248; M-1 to L-247; M-1 to M-246; M-1 to L-245; M-1 to L-244; M-1 to L-243; M-1 to S-242; M-1 to V-241; M-1 to P-240; M-1 to V-239; M-1 to V-238; M-1 to V-237; M-1 to L-236; M-1 to L-235; M-1 to V-234; M-1 to D-233; M-1 to K-232; M-1 to Y-231; M-1 to S-230; M-1 to A-229; M-1 to K-228; M-1 to G-227; M-1 to P-226; M-1 to A-225; M-1 to A-224; M-1 to E-223; M-1 to H-222; M-1 to H-221; M-1 to C-220; M-1 to S-219; M-1 to D-218; M-1 to W-217; M-1 to P-216; M-1 to T-215; M-1 to V-214; M-1 to T-213; M-1 to A-212; M-1 to L-211; M-1 to D-210; M-1 to W-209; M-1 to S-208; M-1 to V-207; M-1 to P-206; M-1 to N-205; M-1 to S-204; M-1 to V-203; M-1 to I-202; M-1 to C-201; M-1 to S-200; M-1 to Y-199; M-1 to A-198; M-1 to V-197; M-1 to D-196; M-1 to R-195; M-1 to D-194; M-1 to G-193; M-1 to P-192; M-1 to G-191; M-1 to L-190; M-1 to S-189; M-1 to I-188; M-1 to S-187; M-1 to L-186; M-1 to V-185; M-1 to Q-184; M-1 to G-183; M-1 to D-182; M-1 to T-181; M-1 to F-180; M-1 to L-179; M-1 to S-178; M-1 to H-177; M-1 to P-176; M-1 to E-175; M-1 to M-174; M-1 to G-173; M-1 to F-172; M-1 to D-171; M-1 to M-170; M-1 to T-169; M-1 to T-168; M-1 to E-167; M-1 to R-166; M-1 to R-165; M-1 to W-164; M-1 to S-163; M-1 to Y-162; M-1 to T-161; M-1 to I-160; M-1 to E-159; M-1 to S-158; M-1 to I-157; M-1 to N-156; M-1 to P-155; M-1 to A-154; M-1 to W-153; M-1 to C-152; M-1 to S-151;

M-1 to L-150; M-1 to F-149; M-1 to V-148; M-1 to Q-147; M-1 to C-146; M-1 to T-145; M-1 to K-144; M-1 to S-143; M-1 to P-142; M-1 to Q-141; M-1 to A-140; M-1 to D-139; M-1 to R-138; M-1 to E-137; M-1 to V-136; M-1 to A-135; M-1 to I-134; M-1 to F-133; M-1 to V-132; M-1 to Q-131; M-1 to V-130; M-1 to V-129; M-1 to P-128; M-1 to R-127; M-1 to P-126; M-1 to V-125; M-1 to A-124; M-1 to D-123; M-1 to Y-122; M-1 to V-121; M-1 to K-120; M-1 to L-119; M-1 to Q-118; M-1 to L-117; M-1 to T-116; M-1 to Q-115; M-1 to T-114; M-1 to W-113; M-1 to P-112; M-1 to Q-111; M-1 to G-110; M-1 to R-109; M-1 to T-108; M-1 to D-107; M-1 to V-106; M-1 to M-105; M-1 to L-104; M-1 to V-103; M-1 to S-102; M-1 to F-101; M-1 to N-100; M-1 to G-99; M-1 to S-98; M-1 to D-97; M-1 to G-96; M-1 to S-95; M-1 to E-94; M-1 to L-93; M-1 to P-92; M-1 to G-91; M-1 to L-90; M-1 to E-89; M-1 to L-88; M-1 to S-87; M-1 to L-86; M-1 to N-85; M-1 to S-84; M-1 to H-83; M-1 to L-82; M-1 to Q-81; M-1 to A-80; M-1 to R-79; M-1 to G-78; M-1 to L-77; M-1 to F-76; M-1 to R-75; M-1 to S-74; M-1 to H-73; M-1 to Y-72; M-1 to L-71; M-1 to T-70; M-1 to E-69; M-1 to L-68; M-1 to S-67; M-1 to G-66; M-1 to R-65; M-1 to F-64; M-1 to F-63; M-1 to T-62; M-1 to A-61; M-1 to L-60; M-1 to L-59; M-1 to E-58; M-1 to E-57; M-1 to S-56; M-1 to P-55; M-1 to W-54; M-1 to L-53; M-1 to to S-52; M-1 to R-51; M-1 to W-50; M-1 to I-49; M-1 to A-48; M-1 to E-47; M-1 to R-46; M-1 to V-45; M-1 to Q-44; M-1 to F-43; M-1 to G-42; M-1 to P-41; M-1 to P-40; M-1 to R-39; M-1 to A-38; M-1 to A-37; M-1 to V-36; M-1 to L-35; M-1 to L-34; M-1 to V-33; M-1 to S-32; M-1 to G-31; M-1 to G-30; M-1 to V-29; M-1 to K-28; M-1 to S-27; M-1 to L-26; M-1 to V-25; M-1 to Q-24; M-1 to A-23; M-1 to G-22; M-1 to T-21; M-1 to V-20; M-1 to T-19; M-1 to I-18; M-1 to P-17; M-1 to L-16; M-1 to L-15; M-1 to A-14; M-1 to E-13; M-1 to W-12; M-1 to L-11; M-1 to L-10; M-1 to L-9; M-1 to S-8; M-1 to W-7; of SEQ ID NO:2. Polynucleotides encoding these polypeptides are also encompassed by the invention.

In addition, any of the above listed N- or C-terminal deletions can be combined to produce a N- and C-terminal deleted D-SLAM polypeptide. The invention also provides polypeptides having one or more amino acids deleted from both the amino and the carboxyl termini, which may be described generally as having residues m–n of SEQ ID NO:2, where n and m are integers as described above. Polynucleotides encoding these polypeptides are also encompassed by the invention.

Moreover, preferred N- and C-terminal deletion mutants comprise, or in the alternative consist of, the predicted secreted form of D-SLAM. Preferred secreted forms of the D-SLAM include polypeptides comprising the amino acid sequence of residues: M-1 to K-232; V-2 to K-232; M-3 to K-232; R-4 to K-232; P-5 to K-232; L-6 to K-232; W-7 to K-232; S-8 to K-232; L-9 to K-232; L-10 to K-232; L-11to K-232; W-12 to K-232; E-13 to K-232; A-14 to K-232; L-15 to K-232; L-16 to K-232; P-17 to K-232; I-18 to K-232; T-19 to K-232; V-20 to K-232; T-21 to K-232; G-22 to K-232; A-23 to K-232; Q-24 to K-232; V-25 to K-232; L-26 to K-232; S-27 to K-232; K-28 to K-232; V-29 to K-232; G-30 to K-232; G-31 to K-232; S-32 to K-232; V-33 to K-232; L-34 to K-232; L-35 to K-232; V-36 to K-232; A-37 to K-232; A-38 to K-232; R-39 to K-232; P-40 to K-232; P-41 to K-232; G-42 to K-232; F-43 to K-232; Q-44 to K-232; V-45 to K-232; R-46 to K-232; E-47 to K-232; A-48 to K-232; I-49 to K-232; W-50 to K-232; R-51 to K-232; S-52 to K-232; L-53 to K-232; W-54 to K-232; P-55 to K-232; S-56 to K-232; E-57 to K-232; E-58 to K-232; L-59 to K-232; L-60 to K-232; A-61 to K-232; T-62 to K-232; F-63 to K-232; F-64 to K-232; R-65 to K-232; G-66 to K-232; S-67 to K-232; L-68 to K-232; E-69 to K-232; T-70 to K-232; L-71 to K-232; Y-72 to K-232; H-73 to K-232; S-74 to K-232; R-75 to K-232; F-76 to K-232; L-77 to K-232; G-78 to K-232; R-79 to K-232; A-80 to K-232; Q-81 to K-232; L-82 to K-232; H-83 to K-232; S-84 to K-232; N-85 to K-232; L-86 to K-232; S-87 to K-232; L-88 to K-232; E-89 to K-232; L-90 to K-232; G-91 to K-232; P-92 to K-232; L-93 to K-232; E-94 to K-232; S-95 to K-232; G-96 to K-232; D-97 to K-232; S-98 to K-232; G-99 to K-232; N-100 to K-232; F-101 to K-232; S-102 to K-232; V-103 to K-232; L-104 to K-232; M-105 to K-232; V-106 to K-232; D-107 to K-232; T-108 to K-232; R-109 to K-232; G-110 to K-232; Q-111 to K-232; P-112 to K-232; W-113 to K-232; T-114 to K-232; Q-115 to K-232; T-116 to K-232; L-117 to K-232; Q-118 to K-232; L-119 to K-232; K-120 to K-232; V-121 to K-232; Y-122 to K-232; D-123 to K-232; A-124 to K-232; V-125 to K-232; P-126 to K-232; R-127 to K-232; P-128 to K-232; V-129 to K-232; V-130 to K-232; Q-131 to K-232; V-132 to K-232; F-133 to K-232; I-134 to K-232; A-135 to K-232; V-136 to K-232; E-137 to K-232; R-138 to K-232; D-139 to K-232; A-140 to K-232; Q-141 to K-232; P-142 to K-232; S-143 to K-232; K-144 to K-232; T-145 to K-232; C-146 to K-232; Q-147 to K-232; V-148 to K-232; F-149 to K-232; L-150 to K-232; S-151 to K-232; C-152 to K-232; W-153 to K-232; A-154 to K-232; P-155 to K-232; N-156 to K-232; I-157 to K-232; S-158 to K-232; E-159 to K-232; I-160 to K-232; T-161 to K-232; Y-162 to K-232; S-163 to K-232; W-164 to K-232; R-165 to K-232; R-166 to K-232; E-167 to K-232; T-168 to K-232; T-169 to K-232; M-170 to K-232; D-171 to K-232; F-172 to K-232; G-173 to K-232; M-174 to K-232; E-175 to K-232; P-176 to K-232; H-177 to K-232; S-178 to K-232; L-179 to K-232; F-180 to K-232; T-181 to K-232; D-182 to K-232; G-183 to K-232; Q-184 to K-232; V-185 to K-232; L-186 to K-232; S-187 to K-232; I-188 to K-232; S-189 to K-232; L-190 to K-232; G-191 to K-232; P-192 to K-232; G-193 to K-232; D-194 to K-232; R-195 to K-232; D-196 to K-232; V-197 to K-232; A-198 to K-232; Y-199 to K-232; S-200 to K-232; C-201 to K-232; I-202 to K-232; V-203 to K-232; S-204 to K-232; N-205 to K-232; P-206 to K-232; V-207 to K-232; S-208 to K-232; W-209 to K-232; D-210 to K-232; L-211 to K-232; A-212 to K-232; T-213 to K-232; V-214 to K-232; T-215 to K-232; P-216 to K-232; W-217 to K-232; D-218 to K-232; S-219 to K-232; C-220 to K-232; H-221 to K-232; H-222 to K-232; E-223 to K-232; A-224 to K-232; A-225 to K-232; P-226 to K-232; G-227 to K-232; of SEQ If NO:2. Polynucleotides encoding these polypeptides are also encompassed by the invention.

Additionally, preferred N- and C-terminal deletion mutants comprise, or in the alternative consist of, fragments lacking the predicted signal sequence of D-SLAM. Preferred fragments of D-SLAM include polypeptides comprising the amino acid sequence of residues: A-23 to L-284; A-23 to D-283; A-23 to Q-282; A-23 to V-281; A-23 to L-280; A-23 to P-279; A-23 to N-278; A-23 to E-277; A-23 to T-276; A-23 to E-275; A-23 to P-274; A-23 to G-273; A-23 to V-272; A-23 to R-271; A-23 to D-270; A-23 to A-269; A-23 to H-268; A-23 to V-267; A-23 to D-266; A-23 to K-265; A-23 to K-264; A-23 to K-263; A-23 to K-262; A-23 to G-261; A-23 to S-260; A-23 to C-259; A-23 to P-258; A-23 to C-257; A-23 to W-256; A-23 to H-255; A-23 to W-254; A-23 to A-253; A-23 to S-252; A-23 to F-251; A-23 to L-250; A-23 to T-249; A-23 to V-248; A-23 to L-247; A-23 to M-246; A-23 to L-245; A-23 to L-244; A-23 to L-243; A-23 to S-242; A-23 to V-241; A-23 to P-240; A-23 to V-239; A-23 to V-238; A-23 to V-237; A-23 to L-236; A-23 to L-235; A-23 to V-234; A-23 to D-233; A-23 to K-232;

A-23 to Y-231; A-23 to S-230; A-23 to A-229; A-23 to K-228; A-23 to G-227; A-23 to P-226; A-23 to A-225; A-23 to A-224; A-23 to E-223; A-23 to H-222; A-23 to H-221; A-23 to C-220; A-23 to S-219; A-23 to D-218; A-23 to W-217; A-23 to P-216; A-23 to T-215; A-23 to V-214; A-23 to T-213; A-23 to A-212; A-23 to L-211; A-23 to D-210; A-23 to W-209; A-23 to S-208; A-23 to V-207; A-23 to P-206; A-23 to N-205; A-23 to S-204; A-23 to V-203; A-23 to I-202; A-23 to C-201; A-23 to S-200; A-23 to Y-199; A-23 to A-198; A-23 to V-197; A-23 to D-196; A-23 to R-195; A-23 to D-194; A-23 to G-193; A-23 to P-192; A-23 to G-191; A-23 to L-190; A-23 to S-189; A-23 to I-188; A-23 to S-187; A-23 to L-186; A-23 to V-185; A-23 to Q-184; A-23 to G-183; A-23 to D-182; A-23 to T-181; A-23 to F-180; A-23 to L-179; A-23 to S-178; A-23 to H-177; A-23 to P-176; A-23 to E-175; A-23 to M-174; A-23 to G-173; A-23 to F-172; A-23 to D-171; A-23 to M-170; A-23 to T-169; A-23 to T-168; A-23 to E-167; A-23 to R-166; A-23 to R-165; A-23 to W-164; A-23 to S-163; A-23 to Y-162; A-23 to T-161; A-23 to I-160; A-23 to E-159; A-23 to S-158; A-23 to I-157; A-23 to N-156; A-23 to P-155; A-23 to A-154; A-23 to W-153; A-23 to C-152; A-23 to S-151; A-23 to L-150; A-23 to F-149; A-23 to V-148; A-23 to Q-147; A-23 to C-146; A-23 to T-145; A-23 to K-144; A-23 to S-143; A-23 to P-142; A-23 to Q-141; A-23 to A-140; A-23 to D-139; A-23 to R-138; A-23 to E-137; A-23 to V-136; A-23 to A-135; A-23 to I-134; A-23 to F-133; A-23 to V-132; A-23 to Q-131; A-23 to V-130; A-23 to V-129; A-23 to P-128; A-23 to R-127; A-23 to P-126; A-23 to V-125; A-23 to A-124; A-23 to D-123; A-23 to Y-122; A-23 to V-121; A-23 to K-120; A-23 to L-119; A-23 to Q-118; A-23 to L-117; A-23 to T-116; A-23 to Q-115; A-23 to T-114; A-23 to W-113; A-23 to P-112; A-23 to Q-111; A-23 to G-110; A-23 to R-109; A-23 to T-108; A-23 to D-107; A-23 to V-106; A-23 to M-105; A-23 to L-104; A-23 to V-103; A-23 to S-102; A-23 to F-101; A-23 to N-100; A-23 to G-99; A-23 to S-98; A-23 to D-97; A-23 to G-96; A-23 to S-95; A-23 to E-94; A-23 to L-93; A-23 to P-92; A-23 to G-91; A-23 to L-90; A-23 to E-89; A-23 to L-88; A-23 to S-87; A-23 to L-86; A-23 to N-85; A-23 to S-84; A-23 to H-83; A-23 to L-82; A-23 to Q-81; A-23 to A-80; A-23 to R-79; A-23 to G-78; A-23 to L-77; A-23 to F-76; A-23 to R-75; A-23 to S-74; A-23 to H-73; A-23 to Y-72; A-23 to L-71; A-23 to T-70; A-23 to E-69; A-23 to L-68; A-23 to S-67; A-23 to G-66; A-23 to R-65; A-23 to F-64; A-23 to F-63; A-23 to T-62; A-23 to A-61; A-23 to L-60; A-23 to L-59; A-23 to E-58; A-23 to E-57; A-23 to S-56; A-23 to P-55; A-23 to W-54; A-23 to L-53; A-23 to S-52; A-23 to R-51; A-23 to W-50; A-23 to I-49; A-23 to A-48; A-23 to E-47; A-23 to R-46; A-23 to V-45; A-23 to Q-44; A-23 to F-43; A-23 to G-42; A-23 to P-41; A-23 to P-40; A-23 to R-39; A-23 to A-38; A-23 to A-37; A-23 to V-36; A-23 to L-35; A-23 to L-34; A-23 to V-33; A-23 to S-32; A-23 to G-31; A-23 to G-30; A-23 to V-29; of SEQ ID NO:2.

The present application is also directed to proteins containing polypeptides at least 90%, 95%, 96%, 97%, 98% or 99% identical to the D-SLAM polypeptide sequence set forth herein m–n. In preferred embodiments, the application is directed to proteins containing polypeptides at least 90%, 95%, 96%, 97%, 98% or 99% identical to polypeptides having the amino acid sequence of the specific D-SLAM N- and C-terminal deletions recited herein. Polynucleotides encoding these polypeptides are also encompassed by the invention.

Among the especially preferred fragments of the invention are fragments characterized by structural or functional attributes of D-SLAM. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) D-SLAM (SEQ ID NO:2). Certain preferred regions are those set out in FIG. 3 and include, but are not limited to, regions of the aforementioned types identified by analysis of the amino acid sequence depicted in FIG. 1 (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of D-SLAM. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of D-SLAM.

The data representing the structural or functional attributes of D-SLAM set forth in FIG. 1 and/or Table I, as described above, was generated using the various modules and algorithms of the DNA*STAR set on default parameters. In a preferred embodiment, the data presented in columns VIII, IX, XIII, and XIV of Table I can be used to determine regions of D-SLAM which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region.

The above-mentioned preferred regions set out in FIG. 3 and in Table I include, but are not limited to, regions of the aforementioned types identified by analysis of the amino acid sequence set out in FIG. 1. As set out in FIG. 3 and in Table I, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

Among highly preferred fragments in this regard are those that comprise regions of D-SLAM that combine several structural features, such as several of the features set out in Table 1.

Other preferred fragments are biologically active D-SLAM fragments. Biologically active fragments are those exhibiting activity similar, but not necessarily identical, to an activity of the D-SLAM polypeptide. The biological activity of the fragments may include an improved desired activity, or a decreased undesirable activity.

However, many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. For example, the following ESTs are preferably excluded from the present invention: AA917335; AI094818, AI298413; N62522; AA627522; R11635; AA320408; AA379112; R09841; Z20320; N79421; D45800; T98959; AA217290; N30197; AA286132; and AA633983 (hereby incorporated by reference in their entirety.) However, to list every related sequence would be cumbersome. Accordingly, preferably excluded from the present invention are one or more polynucleotides comprising a nucleotide sequence described by the general formula of a–b, where a is any integer between 1 to 3206 of SEQ ID NO:1, b is an integer of 15 to 3220, where both a and b correspond to the positions of nucleotide residues shown in SEQ ID NO:1, and where the b is greater than or equal to a+14.

Epitope-Bearing Portions

In another aspect, the invention provides peptides and polypeptides comprising epitope-bearing portions of the polypeptides of the present invention. These epitopes are immunogenic or antigenic epitopes of the polypeptides of the present invention. An "immunogenic epitope" is defined as a part of a protein that elicits an antibody response in vivo when the whole polypeptide of the present invention, or fragment thereof, is the immunogen. On the other hand, a region of a polypeptide to which an antibody can bind is defined as an "antigenic determinant" or "antigenic epitope." The number of in vivo immunogenic epitopes of a protein generally is less than the number of antigenic epitopes. See, e.g., Geysen, et al. (1983) Proc. Natl. Acad. Sci. USA 81:3998–4002. However, antibodies can be made to any antigenic epitope, regardless of whether it is an immunogenic epitope, by using methods such as phage display. See e.g., Petersen G. et al. (1995) Mol. Gen. Genet. 249:425–431. Therefore, included in the present invention are both immunogenic epitopes and antigenic epitopes.

A list of exemplified amino acid sequences comprising immunogenic epitopes are shown in Table 1 below. It is pointed out that Table 1 only lists amino acid residues comprising epitopes predicted to have the highest degree of antigenicity using the algorithm of Jameson and Wolf, (1988) Comp. Appl. Biosci. 4:181–186 (said references incorporated by reference in their entireties). The Jameson-Wolf antigenic analysis was performed using the computer program PROTEAN, using default parameters (Version 3.11 for the Power MacIntosh, DNASTAR, Inc., 1228 South Park Street Madison, Wis.). Table 1 and portions of polypeptides not listed in Table 1 are not considered non-immunogenic. The immunogenic epitopes of Table 1 is an exemplified list, not an exhaustive list, because other immunogenic epitopes are merely not recognized as such by the particular algorithm used. Amino acid residues comprising other immunogenic epitopes may be routinely determined using algorithms similar to the Jameson-Wolf analysis or by in vivo testing for an antigenic response using methods known in the art. See, e.g., Geysen et al., supra; U.S. Pat. Nos. 4,708,781; 5,194,392; 4,433,092; and 5,480,971 (said references incorporated by reference in their entireties).

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to D-SLAM-specific antibodies include: a polypeptide comprising amino acid residues in SEQ ID NO:2 from about 29–32, 39–45, 48–50, 52–59, 64–72, 76–78, 91–101, 106–114, 121–128, 136–146, 162–178, 190–198, 216–233, and 257–285. These polypeptide fragments have been determined to bear antigenic epitopes of the D-SLAM protein by the analysis of the Jameson-Wolf antigenic index, as shown in FIG. 3, above.

It is particularly pointed out that the amino acid sequences of Table 1 comprise immunogenic epitopes. Table 1 lists only the critical residues of immunogenic epitopes determined by the Jameson-Wolf analysis. Thus, additional flanking residues on either the N-terminal, C-terminal, or both N- and C-terminal ends may be added to the sequences of Table 1 to generate an epitope-bearing polypeptide of the present invention. Therefore, the immunogenic epitopes of Table 1 may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences. Polypeptides of the present invention comprising immunogenic or antigenic epitopes are at least 7 amino acids residues in length. "At least" means that a polypeptide of the present invention comprising an immunogenic or antigenic epitope may be 7 amino acid residues in length or any integer between 7 amino acids and the number of amino acid residues of the full length polypeptides of the invention. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. However, it is pointed out that each and every integer between 7 and the number of amino acid residues of the full length polypeptide are included in the present invention.

The immuno and antigenic epitope-bearing fragments may be specified by either the number of contiguous amino acid residues, as described above, or further specified by N-terminal and C-terminal positions of these fragments on the amino acid sequence of SEQ ID NO:2. Every combination of a N-terminal and C-terminal position that a fragment of, for example, at least 7 or at least 15 contiguous amino acid residues in length could occupy on the amino acid sequence of SEQ ID NO:2 is included in the invention. Again, "at least 7 contiguous amino acid residues in length" means 7 amino acid residues in length or any integer between 7 amino acids and the number of amino acid residues of the full length polypeptide of the present invention. Specifically, each and every integer between 7 and the number of amino acid residues of the full length polypeptide are included in the present invention.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immunoassays, specifically for the polypeptides of the present invention using methods known in the art. See, e.g., Harlow et al., Antibodies: A Laboratory Manual, (Cold Spring Harbor Laboratory Press; 2nd Ed. 1988).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10–20 mgs of 248 individual and distinct 13 residue peptides representing single amino acid variants of a segment of the HA1 polypeptide, all of which were prepared and characterized (by ELISA-type binding studies) in less than four weeks (Houghten, R. A. Proc. Natl. Acad. Sci. USA 82:5131–5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al. (1985) Proc. Natl. Acad. Sci. 82:5131–5135 at 5134.

Epitope-bearing polypeptides of the present invention are used to induce antibodies according to methods well known in the art including, but not limited to, in vivo immunization, in vitro immunization, and phage display methods. See, e.g., Sutcliffe, et al., supra; Wilson, et al., supra, and Bittle, et al. (1985) J. Gen. Virol. 66:2347–2354. If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of imnmunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al. (1988) Nature 331:84–86. Fusion proteins that have a disulfide-linked dimeric structure due to the IgG portion can also be more efficient in binding and neutralizing other molecules than monomeric polypeptides or fragments thereof alone. See, e.g., Fountoulakis et al. (1995) J. Biochem. 270:3958–3964. Nucleic acids encoding the above epitopes can also be recombined with a gene of interest as an epitope tag to aid in detection and purification of the expressed polypeptide.

Antibodies

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes monoclonal, polyclonal, chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A, et al. (1991) J. Immunol. 147:60–69; U.S. Pat. Nos. 5,573,920, 4,474,893, 5,601,819, 4,714,681, 4,925,648; Kostelny, S. A. et al. (1992) J. Immunol. 148:1547–1553.

Antibodies of the present invention may be described of specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded.

Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art and taught in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties). Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) J. Immunol. Methods 182:41–50; Ames, R. S. et al. (1995) J. Immunol. Methods 184:177–186; Kettleborough, C. A. et al. (1994) Eur. J. Immunol. 24:952–958; Persic, L. et al. (1997) Gene 1879–18; Burton, D. R. et al. (1994) Advances in Immunology 57:191–280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al. (1992) BioTechniques 12(6):864–869; and Sawai, H. et al. (1995) AJRI 34:26–34; and Better, M. et al. (1988) Science 240:1041–1043 (said references incorporated by reference in their entireties).

Examples of techniques which can be used to produce single-chain Fvs and antibodies include those described in U.S. Pat. Nos. 4,946,778 and 5,258,498; Huston et al. (1991) Methods in Enzymology 203:46–88; Shu, L. et al. (1993) PNAS 90:7995–7999; and Skerra, A. et al. (1988) Science 240:1038–1040. For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies, S. D. et al. (1989) J. Immunol. Methods 125:191–202; and U.S. Pat. No. 5,807, 715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., (1991) Molecular Immunology 28(4/5):489–498; Studnicka G. M. et al. (1994) Protein Engineering 7(6):805–814; Roguska M. A. et al. (1994) PNAS 91:969–973), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645, WO 98/50433, WO 98/24893, WO 98/16654, WO 96/34096, WO 96/33735, and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994) Immunol. Lett. 39:91–99; U.S. Pat. No. 5,474, 981; Gillies, S. O. et al. (1992) PNAS 89:1428–1432; Fell, H. P. et al. (1991) J. Immunol. 146:2446–2452 (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) PNAS 88:10535–10539; Zheng, X. X. et al. (1995) J. Immunol. 154:5590–5600; and Vil, H. et al. (1992) PNAS 89:11337–11341 (said references incorporated by reference in their entireties).

The invention further relates to antibodies that act as agonists or antagonists of the polypeptides of the present invention. Antibodies which act as agonists or antagonists of the polypeptides of the present invention include, for example, antibodies which disrupt receptor/ligand interactions with the polypeptides of the invention either partially or fully. For example, the present invention includes antibodies that disrupt the ability of the proteins of the invention to multimerize. In another example, the present invention includes antibodies which allow the proteins of the invention to multimerize, but disrupts the ability of the proteins of the invention to bind one or more D-SLAM receptor(s)/ligand(s). In yet another example, the present invention includes antibodies which allow the proteins of the invention to multimerize, and bind D-SLAM receptor(s)/ligand(s), but blocks biological activity associated with the D-SLAM/receptor/ligand complex.

Antibodies which act as agonists or antagonists of the polypeptides of the present invention also include, both receptor-specific antibodies and ligand-specific antibodies. Included are receptor-specific antibodies that do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al., Blood 92(6):1981–1988 (1998); Chen, Z. et al., Cancer Res. 58(16):3668–3678 (1998); Harrop, J. A. et al., J. Immunol. 161(4):1786–1794 (1998); Zhu, Z. et al., Cancer Res. 58(15):3209–3214 (1998); Yoon, D. Y. et al., J. Immunol. 160(7):3170–3179 (1998); Prat, M. et al., J. Cell. Sci. 111(Pt2):237–247 (1998); Pitard, V. et al., J. Immunol. Methods 205(2):177–190 (1997); Liautard, J. et al., Cytokinde 9(4):233–241 (1997); Carlson, N. G. et al., J. Biol. Chem. 272(17):11295–11301 (1997); Taryman, R. E. et al., Neuron 14(4):755–762 (1995); Muller, Y. A. et al., Structure 6(9):1153–1167 (1998); Bartunek, P. et al., Cytokine 8(1) :14–20 (1996)(said references incorporated by reference in their entireties).

As discussed above, antibodies to the D-SLAM proteins of the invention can, in turn, be utilized to generate anti-idiotype antibodies that "mimic" D-SLAM using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to D-SLAM and competitively inhibit D-SLAM multimerization and/or binding to ligand can be used to generate anti-idiotypes that "mimic" the D-SLAM mutimerization and/or binding domain and, as a consequence, bind to and neutralize D-SLAM and/or its ligand. Such neutralizing anti-idiotypes or Fab fragments of such anti-idiotypes can be used in therapeutic regimens to neutralize D-SLAM ligand. For example, such anti-idiotypic antibodies can be used to bind D-SLAM, or to bind D-SLAM ligands/receptors, and thereby block D-SLAM biological activity.

Fusion Proteins

Any D-SLAM polypeptide can be used to generate fusion proteins. For example, the D-SLAM polypeptide, when fused to a second protein, can be used as an antigenic tag. Antibodies raised against the D-SLAM polypeptide can be used to indirectly detect the second protein by binding to the D-SLAM. Moreover, because secreted proteins target cellular locations based on trafficking signals, the D-SLAM polypeptides can be used as a targeting molecule once fused to other proteins.

Examples of domains that can be fused to D-SLAM polypeptides include not only heterologous signal sequences, but also other heterologous functional regions. The fusion does not necessarily need to be direct, but may occur through linker sequences.

In certain preferred embodiments, D-SLAM proteins of the invention comprise fusion proteins wherein the D-SLAM polypeptides are those described above as m–n. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

Moreover, fusion proteins may also be engineered to improve characteristics of the D-SLAM polypeptide. For instance, a region of additional amino acids, particularly charged amino acids, may be added to the N-terminus of the D-SLAM polypeptide to improve stability and persistence during purification from the host cell or subsequent handling and storage. Also, peptide moieties may be added to the D-SLAM polypeptide to facilitate purification. Such regions may be removed prior to final preparation of the D-SLAM polypeptide. The addition of peptide moieties to facilitate handling of polypeptides are familiar and routine techniques in the art.

Moreover, D-SLAM polypeptides, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the D-SLAM polypeptides can be fused to marker sequences, such as a peptide which facilitates purification of D-SLAM. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the D-SLAM polynucleotides or the polypeptides.

Vectors, Host Cells, and Protein Production

The present invention also relates to vectors containing the D-SLAM polynucleotide, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

D-SLAM polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The D-SLAM polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that D-SLAM polypeptides may in fact be expressed by a host cell lacking a recombinant vector.

D-SLAM polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

D-SLAM polypeptides, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the D-SLAM polypeptides may be glycosylated or may be non-glycosylated. In addition, D-SLAM polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., D-SLAM coding sequence), and/or to include genetic material (e.g., heterologous polynucleotide sequences) that is operably associated with D-SLAM polynucleotides of the invention, and which activates, alters, and/or amplifies endogenous D-SLAM polynucleotides. For example, techniques known in the art may be used to operably associate heterologous control regions (e.g., promoter and/or enhancer) and endogenous D-SLAM polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller, M., et al., 1984, Nature 310:105–111). For example, a peptide corresponding to a fragment of the D-SLAM polypeptides of the invention can be synthesized by use of a peptide synthesizer. Furthermore, if desired, nonclassical amino acids or chemical amino acid analogs can be introduced as a substitution or addition into the D-SLAM polynucleotide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses D-SLAM polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of D-SLAM which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The D-SLAM polypeptides of the invention may be in monomers or multimers (i.e., dimers, trimers, tetramers and higher multimers). Accordingly, the present invention relates to monomers and multimers of the D-SLAM polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only D-SLAM polypeptides of the invention (including D-SLAM fragments, variants, splice variants, and fusion proteins, as described herein). These homomers may contain D-SLAM polypeptides having identical or different amino acid sequences. In a specific embodiment, a homomer of the invention is a multimer containing only D-SLAM polypeptides having an identical amino acid sequence. In another specific embodiment, a homomer of the invention is a multimer containing D-SLAM polypeptides having different amino acid sequences. In specific embodiments, the multimer of the invention is a homodimer (e.g., containing D-SLAM polypeptides having identical or different amino acid sequences) or a homotrimer (e.g., containing D-SLAM polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the D-SLAM polypeptides of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the D-SLAM polypeptides of the invention. Such covalent associations may involve one or more amino acid residues contained in the polypeptide sequence (e.g., that recited in SEQ ID NO:2, or contained in the polypeptide encoded by the clone HDPJO39). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a D-SLAM fusion protein. In one example, covalent associations are between the heterologous sequence contained in a fusion protein of the invention (see, e.g., U.S. Pat. No. 5,478,925). In a specific example, the covalent associations are between the heterologous sequence contained in a D-SLAM-Fc fusion protein of the invention (as described herein). In another specific example, covalent associations of fusion proteins of the invention are between heterologous polypeptide sequence from another Secreted Lymphocyte Activation Molecule (SLAM) family member that is capable of forming covalently associated multimers, such as for example, oseteoprotegerin (see, e.g., International Publication No. WO 98/49305, the contents of which are herein incorporated by reference in its entirety).

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Uses of the D-SLAM Polynucleotides

The D-SLAM polynucleotides identified herein can be used in numerous ways as reagents. The following description should be considered exemplary and utilizes known techniques.

There exists an ongoing need to identify new chromosome markers, since few chromosome marking reagents, based on actual sequence data (repeat polymorphisms), are presently available.

Briefly, sequences can be mapped to chromosomes by preparing PCR primers (preferably 15–25 bp) from the sequences shown in SEQ ID NO:1. Primers can be selected using computer analysis so that primers do not span more than one predicted exon in the genomic DNA. These primers are then used for PCR screening of somatic cell hybrids containing individual human chromosomes. Only those hybrids containing the human D-SLAM gene corresponding to the SEQ ID NO:1 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the D-SLAM polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the D-SLAM polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the D-SLAM polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library) .) Assuming 1 megabase mapping resolution and one gene per 20 kb, a cDNA precisely localized to a chromosomal region associated with the disease could be one of 50–500 potential causative genes.

Thus, once coinheritance is established, differences in the D-SLAM polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the D-SLAM polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using D-SLAM polynucleotides. Any of these alterations (altered expression, chromosomal rearrangement, or mutation) can be used as a diagnostic or prognostic marker.

In addition to the foregoing, a D-SLAM polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

D-SLAM polynucleotides are also useful in gene therapy. One goal of gene therapy is to insert a normal gene into an organism having a defective gene, in an effort to correct the genetic defect. D-SLAM offers a means of targeting such genetic defects in a highly accurate manner. Another goal is to insert a new gene that was not present in the host genome, thereby producing a new trait in the host cell.

The D-SLAM polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The D-SLAM polynucleotides can be used as additional DNA markers for RFLP.

The D-SLAM polynucleotides can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, D-SLAM polynucleotides can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from D-SLAM sequences. Panels of such reagents can identify tissue by species and/or by organ type. In a similar fashion, these reagents can be used to screen tissue cultures for contamination.

Because D-SLAM is found expressed in dendritic cells, T cell lymphoma, lymph node, spleen, thymus, small intestine, and uterus, D-SLAM polynucleotides are useful as hybridization probes for differential identification of the tissue(s) or cell type(s) present in a biological sample. Similarly, polypeptides and antibodies directed to D-SLAM polypeptides are useful to provide immunological probes for differential identification of the tissue(s) or cell type(s). In addition, for a number of disorders of the above tissues or cells, particularly of the immune system, significantly higher or lower levels of D-SLAM gene expression may be detected in certain tissues (e.g., cancerous and wounded tissues) or bodily fluids (e.g., serum, plasma, urine, synovial fluid or spinal fluid) taken from an individual having such a disorder, relative to a "standard" D-SLAM gene expression level, i.e., the D-SLAM expression level in healthy tissue from an individual not having the immune system disorder.

Thus, the invention provides a diagnostic method of a disorder, which involves: (a) assaying D-SLAM gene expression level in cells or body fluid of an individual; (b) comparing the D-SLAM gene expression level with a standard D-SLAM gene expression level, whereby an increase or decrease in the assayed D-SLAM gene expression level compared to the standard expression level is indicative of disorder in the immune system.

In the very least, the D-SLAM polynucleotides can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of D-SLAM Polypeptides

D-SLAM polypeptides can be used in numerous ways. The following description should be considered exemplary and utilizes known techniques.

D-SLAM polypeptides can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of D-SLAM polypeptide in cells or body fluid of an individual; (b) comparing the level of gene expression with a standard gene expression level, whereby an increase or decrease in the assayed D-SLAM polypeptide gene expression level compared to the standard expression level is indicative of a disorder.

Moreover, D-SLAM polypeptides can be used to treat disease. For example, patients can be administered D-SLAM polypeptides in an effort to replace absent or decreased levels of the D-SLAM polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to D-SLAM polypeptides can also be used to treat disease. For example, administration of an antibody directed to a D-SLAM polypeptide can bind and reduce overproduction of the polypeptide. Similarly, administration of an antibody can activate the polypeptide, such as by binding to a polypeptide bound to a membrane (receptor).

At the very least, the D-SLAM polypeptides can be used as molecular weight markers on SDS-PAGE gels or on molecular sieve gel filtration columns using methods well known to those of skill in the art. D-SLAM polypeptides can also be used to raise antibodies, which in turn are used to measure protein expression from a recombinant cell, as a way of assessing transformation of the host cell. Moreover, D-SLAM polypeptides can be used to test the following biological activities.

Gene Therapy Methods

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of the D-SLAM polypeptide of the present invention. This method requires a polynucleotide which codes for a D-SLAM polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a D-SLAM polynucleotide ex vivo, with the engineered cells then being provided to a patient to be treated with the polypeptide. Such methods are well-known in the art. For example, see Belldegrun, A., et al., J. Natl. Cancer Inst. 85:207–216 (1993); Ferrantini, M. et al., Cancer Research 53:1107–1112 (1993); Ferrantini, M. et al., J. Immunology 153:4604–4615 (1994); Kaido, T., et al., Int. J. Cancer 60:221–229 (1995); Ogura, H., et al., Cancer Research 50:5102–5106 (1990); Santodonato, L., et al., Human Gene Therapy 7:1–10 (1996); Santodonato, L., et al., Gene Therapy 4:1246–1255 (1997); and Zhang, J. -F. et al., Cancer Gene Therapy 3:31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the D-SLAM polynucleotide constructs can be delivered by any method that delivers injectable materials to the cells of an animal, such as, injection into the interstitial space of tissues (heart, muscle, skin, lung, liver, and the like). The D-SLAM polynucleotide constructs may be delivered in a pharmaceutically acceptable liquid or aqueous carrier.

In one embodiment, the D-SLAM polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the D-SLAM polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The D-SLAM polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of D-SLAM DNA. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for D-SLAM.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The D-SLAM polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked D-SLAM DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

As is evidenced in the Examples, naked D-SLAM nucleic acid sequences can be administered in vivo results in the successful expression of D-SLAM polypeptide in the femoral arteries of rabbits.

The constructs may also be delivered with delivery vehicles such as viral sequences, viral particles, liposome formulations, lipofectin, precipitating agents, etc. Such methods of delivery are known in the art.

In certain embodiments, the D-SLAM polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413–7416, which is herein incorporated by reference); mRNA (Malone et al., Proc. Natl. Acad. Sci. USA (1989) 86:6077–6081, which is herein incorporated by reference); and purified transcription factors (Debs et al., J. Biol. Chem. (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., Proc. Natl. Acad. Sci. USA 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15 EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta (1975) 394:483; Wilson et al., Cell (1979) 17:77); ether injection (Deamer, D. and Bangham, A., Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255:10431; Szoka, F. and Papahadjopoulos, D., Proc. Natl. Acad. Sci. USA (1978) 75:145; Schaefer-Ridder et al., Science (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are be engineered, ex vivo or in vivo, using a retroviral particle containing RNA which comprises a sequence encoding D-SLAM. Retroviruses from which the retroviral plasmid vectors may be derived include, but are not limited to, Moloney Murine Leukemia Virus, spleen necrosis virus, *Rous sarcoma* Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding D-SLAM. Such retroviral vector particles then may be employed, to transduce eukaryotic cells, either in vitro or in vivo. The transduced eukaryotic cells will express D-SLAM.

In certain other embodiments, cells are engineered, ex vivo or in vivo, with D-SLAM polynucleotide contained in an adenovirus vector. Adenovirus can be manipulated such that it encodes and expresses D-SLAM, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis.109:233–238). Finally, adenovirus mediated gene transfer has been demonstrated in a number of instances including transfer of alpha-1-antitrypsin and CFTR to the lungs of cotton rats (Rosenfeld, M. A. et al. (1991) Science 252:431–434; Rosenfeld et al., (1992) Cell 68:143–155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, for example, the HARP promoter of the present invention, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The D-SLAM polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the D-SLAM polynucleotide construct. These viral particles are then used to transduce eukaryotic cells, either ex vivo or in vivo. The transduced cells will contain the D-SLAM polynucleotide construct integrated into its genome, and will express D-SLAM.

Another method of gene therapy involves operably associating heterologous control regions and endogenous polynucleotide sequences (e.g. encoding D-SLAM) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the D-SLAM desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous D-SLAM sequence is placed under the control of the promoter. The promoter then drives the expression of the endogenous D-SLAM sequence.

The polynucleotides encoding D-SLAM may be administered along with other polynucleotides encoding other angiongenic proteins. Angiogenic proteins include, but are not limited to, acidic and basic fibroblast growth factors, VEGF-1, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/ macrophage colony stimulating factor, and nitric oxide synthase.

Preferably, the polynucleotide encoding D-SLAM contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities of D-SLAM

D-SLAM polynucleotides or polypeptides, or agonists or antagonists of D-SLAM, can be used in assays to test for one or more biological activities. If D-SLAM polynucleotides or polypeptides, or agonists or antagonists of D-SLAM, do exhibit activity in a particular assay, it is likely that D-SLAM may be involved in the diseases associated with the biological activity. Therefore, D-SLAM could be used to treat the associated disease.

D-SLAM is a cell surface receptor homologous to members of the Secreted Lymphocyte Activation Molecule (SLAM) family, and thus should have activity similar to other SLAM family members. Current studies in the literature demonstrate that SLAM can associate with itself, and that this homotypic interaction can activate B- and T-cells. Therefore, D-SLAM may interact specifically with SLAM, with D-SLAM (a homotypic interaction), or other B- and T-cell receptor molecules on the surface of B- and T-cells to affect the activation, proliferation, survival, and/or differentiation of immune cells. Similarly, soluble D-SLAM may be an important costimulatory molecule for therapeutic uses or immune modulation. Ligands, such as antibodies, may mimic the action of soluble D-SLAM by binding to D-SLAM, SLAM, or other dendritic cell receptors.

Binding of D-SLAM induces the production of interferon-gamma from other cell types, particularly T- and B-cells (data not shown.) The binding may occur through homotypic association with membrane bound D-SLAM, association with SLAM, or association with other T- or B-cell receptors. Ligands, such as antibodies, may mimic the induction of interferon-gamma by soluble D-SLAM by binding to D-SLAM, SLAM, or other dendritic cell receptors.

Moreover, because of the tissue distribution of D-SLAM, this protein may also play a role in stimulating dendritic or antigen presenting cells. For example, a secreted form of D-SLAM, containing the extracellular domain or the full-length form, may bind to and stimulate D-SLAM molecules located on the surface of dendritic or antigen-presenting cells in homotypic manner. Binding may also occur to SLAM, or other dendritic cell surface receptors. This binding may regulate the survival, proliferation, differentiation, activation or maturation of dendritic cells or antigen presenting cells, effecting antigen recognition and immune response. Moreover, ligands, such as antibodies, may mimic the action of soluble D-SLAM by binding to D-SLAM, SLAM, or other dendritic cell receptors.

Thus, D-SLAM may be useful as a therapeutic molecule. It could be used to control the proliferation, activation, maturation, survival, and/or differentiation of hematopoietic cells, in particular B- and T-cells. Particularly, D-SLAM may be a useful therapeutic to mediate immune modulation, and may influence the Th0-TH1-TH2 profile of a patient's immune system. For example, D-SLAM may drive immune response to the Th0–TH1 pathway. This control of immune cells would be particularly important in the treatment of immune disorders, such as autoimmune diseases or immunosuppression (see below). Preferably, treatment of immune disorders could be carried out using a secreted form of D-SLAM, gene therapy, or ex vivo applications. Moreover, inhibitors of D-SLAM, either blocking antibodies or mutant forms, could modulate the expression of D-SLAM. These inhibitors may be useful to treat diseases associated with the misregulation of D-SLAM, such as T cell lymphoma.

Immune Activity

D-SLAM polynucleotides or polypeptides, or agonists or antagonists of D-SLAM, may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, D-SLAM polynucleotides or polypeptides, or agonists or antagonists of D-SLAM, can be used as a marker or detector of a particular immune system disease or disorder.

D-SLAM polynucleotides or polypeptides, or agonists or antagonists of D-SLAM, may be useful in treating or detecting deficiencies or disorders of hematopoietic cells. D-SLAM polynucleotides or polypeptides, or agonists or antagonists of D-SLAM, could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinermia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, D-SLAM polynucleotides or polypeptides, or agonists or antagonists of D-SLAM, can also be used to modulate hemostatic (the stopping of bleeding) or thrombolytic activity (clot formation). For example, by increasing hemostatic or thrombolytic activity, D-SLAM polynucleotides or polypeptides, or agonists or antagonists of D-SLAM, could be used to treat blood coagulation disorders (e.g., afibrinogenemia, factor deficiencies), blood platelet disorders (e.g. thrombocytopenia), or wounds resulting from trauma, surgery, or other causes. Alternatively, D-SLAM polynucleotides or polypeptides, or agonists or antagonists of D-SLAM, that can decrease hemostatic or thrombolytic activity could be used to inhibit or dissolve clotting, important in the treatment of heart attacks (infarction), strokes, or scarring.

D-SLAM polynucleotides or polypeptides, or agonists or antagonists of D-SLAM, may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of D-SLAM polynucleotides or polypeptides, or agonists or antagonists of D-SLAM, that can inhibit an immune response, particularly the proliferation, differentiation, or chemotaxis of T-cells, may be an effective therapy in preventing autoimmune disorders.

Examples of autoimmune disorders that can be treated or detected include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by D-SLAM polynucleotides or polypeptides, or agonists or antagonists of D-SLAM. Moreover, these molecules can be used to treat anaphylaxis, hypersensitivity to an antigenic molecule, or blood group incompatibility.

D-SLAM polynucleotides or polypeptides, or agonists or antagonists of D-SLAM, may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of D-SLAM polynucleotides or polypeptides, or agonists or antagonists of D-SLAM, that inhibits an immune response, particularly the proliferation, differentiation, or chemotaxis of T-cells, may be an effective therapy in preventing organ rejection or GVHD.

Similarly, D-SLAM polynucleotides or polypeptides, or agonists or antagonists of D-SLAM, may also be used to modulate inflammation. For example, D-SLAM polynucleotides or polypeptides, or agonists or antagonists of D-SLAM, may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

D-SLAM polynucleotides or polypeptides, or agonists or antagonists of D-SLAM, can be used to treat or detect hyperproliferative disorders, including neoplasms. D-SLAM polynucleotides or polypeptides, or agonists or antagonists of D-SLAM, may inhibit the proliferation of the disorder through direct or indirect interactions. Alternatively, D-SLAM polynucleotides or polypeptides, or agonists or antagonists of D-SLAM, may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by D-SLAM polynucleotides or polypeptides, or agonists or antagonists of D-SLAM, include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by D-SLAM polynucleotides or polypeptides, or agonists or antagonists of D-SLAM. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Cardiovascular Disorders

D-SLAM polynucleotides or polypeptides, or agonists or antagonists of D-SLAM, encoding D-SLAM may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

D-SLAM polynucleotides or polypeptides, or agonists or antagonists of D-SLAM, are especially effective for the treatment of critical limb ischemia and coronary disease. As shown in the Examples, administration of D-SLAM polynucleotides and polypeptides to an experimentally induced ischemia rabbit hindlimb may restore blood pressure ratio, blood flow, angiographic score, and capillary density.

D-SLAM polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. D-SLAM polypeptides may be administered as part of a pharmaceutical composition, described in more detail below. Methods of delivering D-SLAM polynucleotides are described in more detail herein.

Anti-Angiogenesis Activity

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630–634 (1991); Folkman et al., *N. Engl. J. Med.,* 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases or disorders associated with neovascularization by administration of the D-SLAM polynucleotides and/or polypeptides of the invention, as well as agonists or antagonists of D-SLAM. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)):

Ocular disorders associated with neovascularization which can be treated with the D-SLAM polynucleotides and polypeptides of the present invention (including D-SLAM agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978). Additionally, disorders which can be treated with the D-SLAM polynucleotides and polypeptides of the present invention (including D-SLAM agonist and/or antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated with be treated with the D-SLAM polynucleotides and polypeptides of the present invention (including D-SLAM agonist and/or antagonists) include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uveitis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (Helicobacter pylori), Bartonellosis and bacillary angiomatosis.

Diseases at the Cellular Level

Diseases associated with increased cell survival or the inhibition of apoptosis that could be treated or detected by D-SLAM polynucleotides or polypeptides, as well as antagonists or agonists of D-SLAM, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, D-SLAM polynucleotides, polypeptides, and/or antagonists of the invention are used to inhibit growth, progression, and/or metasis of cancers, in particular those listed above.

Additional diseases or conditions associated with increased cell survival that could be treated or detected by D-SLAM polynucleotides or polypeptides, or agonists or antagonists of D-SLAM, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by D-SLAM polynucleotides or polypeptides, as well as agonists or antagonists of D-SLAM, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing D-SLAM polynucleotides or polypeptides, as well as agonists or antagonists of D-SLAM, for therapeutic purposes, for example, to stimulate epithelial cell proliferation and basal keratinocytes for the purpose of wound healing, and to stimulate hair follicle production and healing of dermal wounds. D-SLAM polynucleotides or polypeptides, as well as agonists or antagonists of D-SLAM, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. D-SLAM polynucleotides or polypeptides, as well as agonists or antagonists of D-SLAM, could be used to promote dermal reestablishment subsequent to dermal loss D-SLAM polynucleotides or polypeptides, as well as agonists or antagonists of D-SLAM, could be used to increase the adherence of skin grafts to a wound bed and to stimulate re-epithelialization from the wound bed. The following are types of grafts that D-SLAM polynucleotides or polypeptides, agonists or antagonists of D-SLAM, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. D-SLAM polynucleotides or polypeptides, as well as agonists or antagonists of D-SLAM, can be used to promote skin strength and to improve the appearance of aged skin.

It is believed that D-SLAM polynucleotides or polypeptides, as well as agonists or antagonists of D-SLAM, will also produce changes in hepatocyte proliferation, and epithelial cell proliferation in the lung, breast, pancreas, stomach, small intesting, and large intestine. D-SLAM polynucleotides or polypeptides, as well as agonists or antagonists of D-SLAM, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. D-SLAM polynucleotides or polypeptides, agonists or antagonists of D-SLAM, may promote proliferation of endothelial cells, keratinocytes, and basal keratinocytes.

D-SLAM polynucleotides or polypeptides, as well as agonists or antagonists of D-SLAM, could also be used to reduce the side effects of gut toxicity that result from radiation, chemotherapy treatments or viral infections. D-SLAM polynucleotides or polypeptides, as well as agonists or antagonists of D-SLAM, may have a cytoprotective effect on the small intestine mucosa. D-SLAM polynucleotides or polypeptides, as well as agonists or antagonists of D-SLAM, may also stimulate healing of mucositis (mouth ulcers) that result from chemotherapy and viral infections.

D-SLAM polynucleotides or polypeptides, as well as agonists or antagonists of D-SLAM, could further be used in full regeneration of skin in full and partial thickness skin defects, including burns, (i.e., repopulation of hair follicles, sweat glands, and sebaceous glands), treatment of other skin defects such as psoriasis. D-SLAM polynucleotides or polypeptides, as well as agonists or antagonists of D-SLAM, could be used to treat epidermolysis bullosa, a defect in adherence of the epidermis to the underlying dermis which results in frequent, open and painful blisters by accelerating reepithelialization of these lesions. D-SLAM polynucleotides or polypeptides, as well as agonists or antagonists of D-SLAM, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, D-SLAM polynucleotides or polypeptides, as well as agonists or antagonists of D-SLAM, could be used to promote the resurfacing of the mucosal surface to aid more rapid healing and to prevent progression of inflammatory bowel disease. Treatment with D-SLAM polynucleotides or polypeptides, agonists or antagonists of D-SLAM, is expected to have a significant effect on the production of mucus throughout the gastrointestinal tract and could be used to protect the intestinal mucosa from injurious substances that are ingested or following surgery. D-SLAM polynucleotides or polypeptides, as well as agonists or antagonists of D-SLAM, could be used to treat diseases associate with the under expression of D-SLAM.

Moreover, D-SLAM polynucleotides or polypeptides, as well as agonists or antagonists of D-SLAM, could be used to prevent and heal damage to the lungs due to various pathological states. A growth factor such as D-SLAM polynucleotides or polypeptides, as well as agonists or antagonists of D-SLAM, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and bums, that cause necrosis of the bronchiolar epithelium and alveoli could be effectively treated using D-SLAM polynucleotides or polypeptides, agonists or antagonists of D-SLAM. Also, D-SLAM polynucleotides or polypeptides, as well as agonists or antagonists of D-SLAM, could be used to stimulate the proliferation of and differentiation of type II pneumocytes, which may help treat or prevent disease such as hyaline membrane diseases, such as infant respiratory distress syndrome and bronchopulmonary displasia, in premature infants.

D-SLAM polynucleotides or polypeptides, as well as agonists or antagonists of D-SLAM, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, D-SLAM polynucleotides or polypeptides, as well as agonists or antagonists of D-SLAM, could be used to treat or prevent the onset of diabetes mellitus. In patients with newly diagnosed Types I and II diabetes, where some islet cell function remains, D-SLAM polynucleotides or polypeptides, as well as agonists or antagonists of D-SLAM, could be used to maintain the islet function so as to alleviate, delay or prevent permanent manifestation of the disease. Also, D-SLAM polynucleotides or polypeptides, as well as agonists or antagonists of D-SLAM, could be used as an auxiliary in islet cell transplantation to improve or promote islet cell function.

Infectious Disease

D-SLAM polynucleotides or polypeptides, or agonists or antagonists of D-SLAM, can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, D-SLAM polynucleotides or polypeptides, or agonists or antagonists of D-SLAM, may also directly inhibit the infectious agent, without necessarily eliciting an immune response.

Viruses are one example of an infectious agent that can cause disease or symptoms that can be treated or detected by D-SLAM polynucleotides or polypeptides, or agonists or antagonists of D-SLAM. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. D-SLAM polynucleotides or polypeptides, or agonists or antagonists of D-SLAM, can be used to treat or detect any of these symptoms or diseases.

Similarly, bacterial or fungal agents that can cause disease or symptoms and that can be treated or detected by D-SLAM polynucleotides or polypeptides, or agonists or antagonists of D-SLAM, include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. D-SLAM polynucleotides or polypeptides, or agonists or antagonists of D-SLAM, can be used to treat or detect any of these symptoms or diseases.

Moreover, parasitic agents causing disease or symptoms that can be treated or detected by D-SLAM polynucleotides or polypeptides, or agonists or antagonists of D-SLAM, include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. D-SLAM polynucleotides or polypeptides, or agonists or antagonists of D-SLAM, can be used to treat or detect any of these symptoms or diseases.

Preferably, treatment using D-SLAM polynucleotides or polypeptides, or agonists or antagonists of D-SLAM, could either be by administering an effective amount of D-SLAM polypeptide to the patient, or by removing cells from the patient, supplying the cells with D-SLAM polynucleotide, and returning the engineered cells to the patient (ex vivo therapy). Moreover, the D-SLAM polypeptide or polynucleotide can be used as an antigen in a vaccine to raise an immune response against infectious disease.

Regeneration

D-SLAM polynucleotides or polypeptides, or agonists or antagonists of D-SLAM, can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, D-SLAM polynucleotides or polypeptides, or agonists or antagonists of D-SLAM, may increase regeneration of tissues difficult to heal. For example, increased tendon/ligament regeneration would quicken recovery time after damage. D-SLAM polynucleotides or polypeptides, or agonists or antagonists of D-SLAM, of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using D-SLAM polynucleotides or polypeptides, or agonists or antagonists of D-SLAM, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the D-SLAM polynucleotides or polypeptides, or agonists or antagonists of D-SLAM.

Chemotaxis

D-SLAM polynucleotides or polypeptides, or agonists or antagonists of D-SLAM, may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

D-SLAM polynucleotides or polypeptides, or agonists or antagonists of D-SLAM, may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. As a chemotactic molecule, D-SLAM could also attract fibroblasts, which can be used to treat wounds.

It is also contemplated that D-SLAM polynucleotides or polypeptides, or agonists or antagonists of D-SLAM, may inhibit chemotactic activity. These molecules could also be used to treat disorders. Thus, D-SLAM polynucleotides or polypeptides, or agonists or antagonists of D-SLAM, could be used as an inhibitor of chemotaxis.

Binding Activity

D-SLAM polypeptides may be used to screen for molecules that bind to D-SLAM or for molecules to which D-SLAM binds. The binding of D-SLAM and the molecule may activate (agonist), increase, inhibit (antagonist), or decrease activity of the D-SLAM or the molecule bound. Examples of such molecules include antibodies, oligonucleotides, proteins (e.g., receptors), or small molecules.

Preferably, the molecule is closely related to the natural ligand of D-SLAM, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which D-SLAM binds, or at least, a fragment of the receptor capable of being bound by D-SLAM (e.g., active site). In either case, the molecule can be rationally designed using known techniques.

Preferably, the screening for these molecules involves producing appropriate cells which express D-SLAM, either as a secreted protein or on the cell membrane. Preferred cells include cells from mammals, yeast, Drosophila, or E. coli. Cells expressing D-SLAM (or cell membrane containing the expressed polypeptide) are then preferably contacted with a test compound potentially containing the molecule to observe binding, stimulation, or inhibition of activity of either D-SLAM or the molecule.

The assay may simply test binding of a candidate compound to D-SLAM, wherein binding is detected by a label, or in an assay involving competition with a labeled competitor. Further, the assay may test whether the candidate compound results in a signal generated by binding to D-SLAM.

Alternatively, the assay can be carried out using cell-free preparations, polypeptide/molecule affixed to a solid support, chemical libraries, or natural product mixtures. The assay may also simply comprise the steps of mixing a candidate compound with a solution containing D-SLAM, measuring D-SLAM/molecule activity or binding, and comparing the D-SLAM/molecule activity or binding to a standard.

Preferably, an ELISA assay can measure D-SLAM level or activity in a sample (e.g., biological sample) using a monoclonal or polyclonal antibody. The antibody can measure D-SLAM level or activity by either binding, directly or indirectly, to D-SLAM or by competing with D-SLAM for a substrate.

Additionally, the receptor to which D-SLAM binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of D-SLAM thereby effectively generating agonists and antagonists of D-SLAM. See generally, U.S. Pat. Nos. 5,605,793, 5,811,238, 5,830, 721, 5,834,252, and 5,837,458, and Patten, P. A., et al., *Curr. Opinion Biotechnol.* 8:724–33 (1997); Harayama, S. *Trends Biotechnol.* 16(2):76–82 (1998); Hansson, L. O., et al., *J. Mol. Biol.* 287:265–76 (1999); and Lorenzo, M. M. and Blasco, R. *Biotechniques* 24(2):308–13 (1998) (each of these patents and publications are hereby incorporated by reference). In one embodiment, alteration of D-SLAM polynucleotides and corresponding polypeptides may be achieved by DNA shuffling. DNA shuffling involves the assembly of two or more DNA segments into a desired D-SLAM molecule by homologous, or site-specific, recombination. In another embodiment, D-SLAM polynucleotides and corresponding polypeptides may be alterred by being subjected to random mutagenesis by error-prone PCR, random nucleotide insertion or other methods prior to recombination. In another embodiment, one or more components, motifs, sections, parts, domains, fragments, etc., of D-SLAM may be recombined with one or more components, motifs, sections, parts, domains, fragments, etc. of one or more heterologous molecules. In preferred embodiments, the heterologous molecules are Secreted Lymphocyte Activation Molecule (SLAM) family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic (dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active D-SLAM fragments. Biologically active fragments are those exhibiting activity similar, but not necessarily identical, to an activity of the D-SLAM polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and $^3[H]$ thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3[H]$ thymidine in each case. The amount of fibroblast cell proliferation is measured by liquid scintillation chromatography which measures the incorporation of $^3[H]$ thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the D-SLAM receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the D-SLAM/molecule. Moreover, the assays can discover agents which may inhibit or enhance the production of D-SLAM from suitably manipulated cells or tissues.

Therefore, the invention includes a method of identifying compounds which bind to D-SLAM comprising the steps of: (a) incubating a candidate binding compound with D-SLAM; and (b) determining if binding has occurred. Moreover, the invention includes a method of identifying agonists/antagonists comprising the steps of: (a) incubating a candidate compound with D-SLAM, (b) assaying a biological activity, and (b) determining if a biological activity of D-SLAM has been altered.

Also, one could identify molecules bind D-SLAM experimentally by using the beta-pleated sheet regions disclosed in FIG. 3 and Table 1. Accordingly, specific embodiments of the invention are directed to polynucleotides encoding polypeptides which comprise, or alternatively consist of, the amino acid sequence of each beta pleated sheet regions disclosed in FIG. 3/Table 1. Additional embodiments of the invention are directed to polynucleotides encoding D-SLAM polypeptides which comprise, or alternatively consist of, any combination or all of the beta pleated sheet regions disclosed in FIG. 3/Table 1. Additional preferred embodiments of the invention are directed to polypeptides which comprise, or alternatively consist of, the D-SLAM amino acid sequence of each of the beta pleated sheet regions disclosed in FIG. 3/Table 1. Additional embodiments of the invention are directed to D-SLAM polypeptides which comprise, or alternatively consist of, any combination or all of the beta pleated sheet regions disclosed in FIG. 3/Table 1.

Antisense And Ribozyme (Antagonists)

In specific embodiments, antagonists according to the present invention are nucleic acids corresponding to the sequences contained in SEQ ID NO:1, or the complementary strand thereof, and/or to nucleotide sequences contained in the deposited clone 209623. In one embodiment, antisense sequence is generated internally by the organism, in another embodiment, the antisense sequence is separately administered (see, for example, O'Connor, J., Neurochem. 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the D-SLAM antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the D-SLAM antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding D-SLAM, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a D-SLAM gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded D-SLAM antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a D-SLAM RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of D-SLAM shown in FIGS. 1A–B could be used in an antisense approach to inhibit translation of endogenous D-SLAM mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of D-SLAM mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the D-SLAM coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy D-SLAM mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of D-SLAM (FIGS. 1A–B). Preferably, the ribozyme is engineered so that the cleavage recognition site is located near the 5' end of the D-SLAM mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express D-SLAM in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous D-SLAM messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat and prevent neuronal damage which occurs in certain neuronal disorders or neuro-degenerative conditions such as Alzheimer's disease, Parkinson's disease, and AIDS-related complex. D-SLAM may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The D-SLAM polypeptide may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The D-SLAM polypeptide may also be employed to maintain organs before transplantation or for supporting cell culture of primary tissues.

The polypeptide of the present invention may also be employed for inducing tissue of mesodermal origin to differentiate in early embryos.

D-SLAM polynucleotides or polypeptides, or agonists or antagonists of D-SLAM, may also increase or decrease the differentiation or proliferation of embryonic stem cells, besides, as discussed above, hematopoietic lineage.

D-SLAM polynucleotides or polypeptides, or agonists or antagonists of D-SLAM, may also be used to modulate mammalian characteristics, such as body height, weight, hair color, eye color, skin, percentage of adipose tissue, pigmentation, size, and shape (e.g., cosmetic surgery). Similarly, D-SLAM polynucleotides or polypeptides, or agonists or antagonists of D-SLAM, may be used to modulate mammalian metabolism affecting catabolism, anabolism, processing, utilization, and storage of energy.

D-SLAM polynucleotides or polypeptides, or agonists or antagonists of D-SLAM, may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

D-SLAM polynucleotides or polypeptides, or agonists or antagonists of D-SLAM, may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Having generally described the invention, the same will be more readily understood by reference to the following examples, which are provided by way of illustration and are not intended as limiting.

Having generally described the invention, the same will be more readily understood by reference to the following examples, which are provided by way of illustration and are not intended as limiting.

EXAMPLES

Example 1

Isolation of the D-SLAM cDNA Clone From the Deposited Sample

The cDNA for D-SLAM is inserted into the SalI/NotI multiple cloning site of pCMVSport 3.0. (Life Technologies, Inc., P. O. Box 6009, Gaithersburg, Md. 20897.) pCMVSport 3.0 contains an ampicillin resistance gene and may be transformed into *E. coli* strain DH10B, also available from Life Technologies. (See, for instance, Gruber, C. E., et al., *Focus* 15:59-(1993).)

Two approaches can be used to isolate D-SLAM from the deposited sample. First, a specific polynucleotide of SEQ ID NO:1 with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host (such as XL-1 Blue (Stratagene)) using techniques known to those of skill in the art, such as those provided by the vector supplier or in related publications or patents. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:1 (i.e., within the region of SEQ ID NO:1 bounded by the 5' NT and the 3' NT of the clone) are synthesized and used to amplify the D-SLAM cDNA using the deposited cDNA plasmid as a template. The polymerase chain reaction is carried out under routine conditions, for instance, in 25 μl of reaction mixture with 0.5 ug of the above cDNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of the D-SLAM gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the D-SLAM gene of interest is used to PCR amplify the 5' portion of the D-SLAM full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the D-SLAM gene.

Example 2

Isolation of D-SLAM Genomic Clones

A human genomic P1 library (Genomic Systems, Inc.) is screened by PCR using primers selected for the cDNA sequence corresponding to SEQ ID NO:1., according to the method described in Example 1. (See also, Sambrook.)

Example 3

Tissue Distribution of D-SLAM Polypeptides

Tissue distribution of mRNA expression of D-SLAM is determined using protocols for Northern blot analysis, described by, among others, Sambrook et al. For example, a D-SLAM probe produced by the method described in Example 1 is labeled with $p^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human inmmune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70 degree C. overnight, and the films developed according to standard procedures.

Example 4

Chromosomal Mapping of D-SLAM

An oligonucleotide primer set is designed according to the sequence at the 5' end of SEQ ID NO:1. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of D-SLAM

D-SLAM polynucleotide encoding a D-SLAM polypeptide invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Alternatively, a construct containing DNA encoding amino acid Q24–D233 of SEQ ID NO:2 can be inserted into pQE70. This construct places a HIS tag (6 histidines) at the C-terminus of the predicted extracellular domain of D-SLAM. Primers that can be used include a 5' primer containing a Sph restriction site, shown in bold: G C A G C A G C AT G C A A G T G C T G A G - CAAAGTCGGGGGCTCGGTGCTG (SEQ ID NO: 14) and a 3' primer, containing a BglII restriction site, shown in bold: G C A G C A A G AT C TAT C T T T G TA G G A G G C - CTTCCCTGGTGCTGCCTC (SEQ ID NO: 15). This construct uses an ATG as a start codon contained within the SphI site, then reading into Q24 of SEQ ID NO:2, and continues until D233 of SEQ ID NO:2. The amino acid sequence encoded by this construct is as follows:

(SEQ ID NO:16)
MQVLSKVGGSVLLVAARPPGFQVREAIWRSLWPSEELLATFFRGSLETLY

HSRFLGRAQLHSNLSLELGPLESGDSGNFSVLMVDTRGQPWTQTLQLKVY

DAVPRPVVQVFIAVERDAQPSKTCQVFLSCWAPNISEITYSWRRETTMDF

GMEPHSLFTDGQVLSISLGPGDRDVAYSCIVSNPVSWDLATVTPWDSCHH

-continued

EAAPGKASYKDQVLSKVGGSVLLVAARPPGFQVREAIWRSLWPSEELLAT

FFRGSLETLYHSRFLGRAQLHSNLSLELGPLESGDSGNFSVLMVDTRGQP

WTQTLQLKVYDAVPRPVVQVFIAVERDAQPSKTCQVFLSCWAPNISEITY

SWRRETTMDFGMEPHSLFTDGQVLSISLGPGDRDVAYSCIVSNPVSWDLA

TVTPWDSCHHEAAPGKASYKDHHHHHH.

Alternatively, a His tag can be placed on the N-terminus of the predicted mature form containing only the extracellular domain of D-SLAM (e.g., corresponding to A23–D233 of SEQ ID NO:2). In this example, the 5' primer, containing a BamHI restriction site, indicated in bold, can be used:
GCAGCAGGATCCGCCCAAGTGCTGAG-CAAAGTCGGGGGCTCGGTG (SEQ ID NO: 17) and a 3' primer can be used:
GCAGCAAAGCTTTTAATCTTTGTAGGAG-GCCTTCCCTGGTGCTGCCTC (SEQ ID NO: 18). These primer can be used to amplify DNA encoding A23–D233, and then the generated product can be inserted into pQE9. This construct puts a His tag on the N-terminus of the predicted mature extracellular domain of D-SLAM. The His tag will be followed by the Gly-Ser of the BamHI site, and this will then be followed by A23 of SEQ ID NO:2. This construct will continue through D233 of SEQ ID NO:2, and will be followed by a TAA stop codon. The amino acid sequence encoded by this construct is as follows:

(SEQ ID NO:19)
MRGSHHHHHHGSAQVLSKVGGSVLLVAARPPGFQVREAIWRSLWPSEELLA

TFFRGSLETLYHSRFLGRAQLHSNLSLELGPLESGDSGNFSVLMVDTRGQP

WTQTLQLKVYDAVPRPVVQVFIAVERDAQPSKTCQVFLSCWAPNISEITYS

WRRETTMDFGMEPHSLFTDGQVLSISLGPGDRDVAYSCIVSNPVSWDLATV

TPWDSCHHEAAPGKASYKD.

Additionally, a mature form containing only the extracellular domain of D-SLAM (amino acids A23 to D233 of SEQ ID NO:2) can also be inserted into an *E. coli* expression vector, such as pHE4 (see below). In this example, the 5' primer, containing a Nde restriction site, indicated in bold, can be used:
GCAGCACATATGGCCCAAGTGCTGAGCAAAGTCG (SEQ ID NO: 20) and a 3' primer containing an Asp718 restriction site, shown in bold, can be used:
GCAGCAGGTACCTTACTAATCTTTGTAG-GAGGCCTTCCCTGGTGCTGCCTC (SEQ ID NO: 21).

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000 Xg). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilotri-acetic acid ("Ni—NTA") affinity resin column (available from QIAGEN, Inc., supra). Proteins with a 6 × His tag bind to the Ni—NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified D-SLAM protein is then renatured by dialyzing it against phosphate-buffered saline (PBS) or 50 mM Na-acetate, pH 6 buffer plus 200 mM NaCl. Alternatively, the D-SLAM protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified D-SLAM protein is stored at 4 degree C. or frozen at −80 degree C.

In addition to the above expression vector, the present invention further includes an expression vector comprising phage operator and promoter elements operatively linked to a D-SLAM polynucleotide, called pHE4a. (ATCC Accession Number 209645, deposited Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of D-SLAM Polypeptide from an Inclusion Body

The following alternative method can be used to purify D-SLAM polypeptide expressed in *E coli* when it is present in the form of inclusion bodies. Unless otherwise specified, all of the following steps are conducted at 4–10 degree C.

Upon completion of the production phase of the *E. coli* fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.)

twice at 4000–6000 psi. The homogenate is then mixed with NaCl solution to a final concentration of 0.5 M NaCl, followed by centrifugation at 7000 xg for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000 xg centrifugation for 15 min., the pellet is discarded and the polypeptide containing supernatant is incubated at 4 degree C. overnight to allow further GuHCl extraction.

Following high speed centrifugation (30,000 xg) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the D-SLAM polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant D-SLAM polypeptide should exhibit greater than 95% purity after the above refolding and purification steps. No major contaminant bands should be observed from Commassie blue stained 16% SDS-PAGE gel when 5 ug of purified protein is loaded. The purified D-SLAM protein can also be tested for endotoxin/LPS contamination, and typically the LPS content is less than 0.1 ng/ml according to LAL assays.

Example 7

Cloning and Expression of D-SLAM in a Baculovirus Expression System

In this example, the plasmid shuttle vector pA2 is used to insert D-SLAM polynucleotide into a baculovirus to express D-SLAM. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned D-SLAM polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the D-SLAM cDNA sequence contained in the deposited clone, including the AUG initiation codon and any naturally associated leader sequence, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

Fragments of D-SLAM can be expressed from the baculovirus system. For example, the predicted extracellular domain (M1–K232 of SEQ ID NO:2) can be inserted into pA2 using the primers described throughout the Example section.

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced D-SLAM protein.

Example 8

Expression of D-SLAM in Mammalian Cells

D-SLAM polypeptide can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2DHFR (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, D-SLAM polypeptide can be expressed in stable cell lines containing the D-SLAM polynucleotide integrated into a chromosome. The co-transfection with a selectable marker such as DHFR, gpt, neomycin, hygromycin allows the identification and isolation of the transfected cells.

The transfected D-SLAM gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-DHFR (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of D-SLAM. The vectors also contain the 3' intron, the polyadenylation and termination signal of the rat preproinsulin gene, and the mouse DHFR gene under control of the SV40 early promoter. Specifically, the plasmid pC6 or pC4 is digested appropriate restriction enzymes and then dephosphorylated using calf intestinal phosphates by procedures known in the art. The vector is then isolated from a 1% agarose gel.

D-SLAM polynucleotide is amplified according to the protocol outlined in Example 1. If a naturally occurring signal sequence is used to produce a secreted protein, the vector does not need a second signal peptide. Alternatively, if a naturally occurring signal sequence is not used, the vector can be modified to include a heterologous signal sequence in an effort to secrete the protein from the cell. (See, e.g., WO 96/34891.)

Specifically, the full length D-SLAM protein can be expressed from a mammalian vector, such as pC4, using the following primers: The 5' primer, containing a BamHI in bold, is as follows:
G C A G C A G G AT C C G C C AT C AT G G T C AT-
GAGGCCCCTGTGGAGTCTGCTTCT C (SEQ ID NO:22) while the 3' primer contains a Xba site shown in bold:
G C A G C AT C TA G AT TAT G G C A G AT C C T G-
CACAAGGGGGTTCTCTGTC (SEQ ID NO: 23). This construct should produce a transmembrane protein that will be expressed on the external cell surface.

Alternatively, a construct containing only the soluble portion of D-SLAM can be made by inserting the predicted extracellular domain of D-SLAM in pC4. For example, DNA encoding M1–K232 of SEQ ID NO:2 can be in inserted into pC4, using a 5' primer, containing a BaniHI restriction site shown in bold:
G C A G C A G G AT C C G C C AT C AT G G T C AT-
GAGGCCCCTGTGGAGTCTGCTTCT C (SEQ ID NO: 22) and a 3' primer, containing a Xba restriction site shown in bold:
G C A G C AT C TA G AT TAT T T G TA G G A G G C-
CTTCCCTGGTGCTGCCTC (SEQ ID NO: 24).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel. The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 or pC4 using, for instance, restriction enzyme analysis.

Chinese hamster ovary cells lacking an active DHFR gene is used for transfection. Five µg of the expression plasmid pC6 or pC4 is cotransfected with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of D-SLAM is analyzed, for instance, by SDS-PAGE and Western blot or by reversed phase HPLC analysis.

Example 9

Construction of N-Terminal and/or C-Terminal Deletion Mutants

The following general approach may be used to clone a N-terminal or C-terminal deletion D-SLAM deletion mutant. Generally, two oligonucleotide primers of about 15–25 nucleotides are derived from the desired 5' and 3' positions of a polynucleotide of SEQ ID NO:1. The 5' and 3' positions of the primers are determined based on the desired D-SLAM polynucleotide fragment. An initiation and stop codon are added to the 5' and 3' primers respectively, if necessary, to express the D-SLAM polypeptide fragment encoded by the polynucleotide fragment. Preferred D-SLAM polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the D-SLAM polynucleotide fragment in a desired vector may also be added to the 5' and 3' primer sequences. The D-SLAM polynucleotide fragment is amplified from genomic DNA or from the deposited cDNA clone using the appropriate PCR oligonucleotide primers and conditions discussed herein or known in the art. The D-SLAM polypeptide fragments encoded by the D-SLAM polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the D-SLAM polypeptide fragment Leu-35 to Thr-276 is amplified and cloned as follows: A 5' primer is generated comprising a restriction enzyme site followed by an initiation codon in frame with the polynucleotide sequence encoding the N-terminal portion of the polypeptide fragment beginning with Leu-35. A complementary 3' primer is generated comprising a restriction enzyme site followed by a stop codon in frame with the polynucleotide sequence encoding C-terminal portion of the D-SLAM polypeptide fragment ending with Thr-276.

The amplified polynucleotide fragment and the expression vector are digested with restriction enzymes which recognize the sites in the primers. The digested polynucleotides are then ligated together. The D-SLAM polynucleotide fragment is inserted into the restricted expression vector, preferably in a manner which places the D-SLAM polypeptide fragment coding region downstream from the promoter. The ligation mixture is transformed into competent E. coli cells using standard procedures and as described in the Examples herein. Plasmid DNA is isolated from resistant colonies and the identity of the cloned DNA confirmed by restriction analysis, PCR and DNA sequencing.

Example 10

Protein Fusions of D-SLAM

D-SLAM polypeptides are preferably fused to other proteins. These fusion proteins can be used for a variety of applications. For example, fusion of D-SLAM polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to D-SLAM polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and D-SLAM polynucleotide, isolated by the PCR protocol described in Example 1, is ligated into this BamHI site. Note that the polynucleotide is cloned without a stop codon, otherwise a fusion protein will not be produced.

Examples of primers that can be used to amplify D-SLAM polypeptides, such as the predicted extracellular domain of D-SLAM include: a 5' primer containing a BamHI restriction site shown in bold:

GCAGCAGGATCCGCCATCATGGTCAT-
GAGGCCCCTGTGGAGTCTGCTTCT C (SEQ ID NO: 22) and a 3' primer, containing a Xba restriction site shown in bold:
GCAGCATCTAGAATCTTTGTAGGAGC-
CTTCCCTGGTGCTGCCTC (SEQ ID NO: 25). Using these primers, the construct will express the predicted extracellular domain of D-SLAM fused to Fc in pC4.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:                    (SEQ ID NO:4)
GGGATCCGGAGCCCAAATCTTCTGACAAAACTCACACATGCCCACCGTGCC

CAGCACCTGAATTCGAGGGTGCACCGTCAGTCTTCCTCTTCCCCCCAAAAC

CCAAGGACACCCTCATGATCTCCCGGACTCCTGAGGTCACATGCGTGGTGG

TGGACGTAAGCCACGAAGACCCTGAGGTCAAGTTCAACTGGTACGTGGACG

GCGTGGAGGTGCATAATGCCAAGACAAAGCCGCGGGAGGAGCAGTACAACA

GCACGTACCGTGTGGTCAGCGTCCTCACCGTCCTGCACCAGGACTGGCTGA

ATGGCAAGGAGTACAAGTGCAAGGTCTCCAACAAAGCCCTCCCAACCCCCA

TCGAGAAAACCATCTCCAAAGCCAAAGGGCAGCCCCGAGAACCACAGGTGT

ACACCCTGCCCCCATCCCGGGATGAGCTGACCAAGAACCAGGTCAGCCTGA

CCTGCCTGGTCAAAGGCTTCTATCCAAGCGACATCGCCGTGGAGTGGGAGA

GCAATGGGCAGCCGGAGAACAACTACAAGACCACGCCTCCCGTGCTGGACT

CCGACGGCTCCTTCTTCCTCTACAGCAAGCTCACCGTGGACAAGAGCAGGT

GGCAGCAGGGGAACGTCTTCTCATGCTCCGTGATGCATGAGGCTCTGCACA

ACCACTACACGCAGAAGAGCCTCTCCCTGTCTCCGGGTAAATGAGTGCGAC

GGCCGCGACTCTAGAGGAT

Alternatively, this same region can be inserted in pA2, creating a fusion of Fc with the predicted extracellular domain of D-SLAM. Examples of primer that can be used to amplify the predicted extracellular domain of D-SLAM include: a 5' primer containing a BamHI restriction site shown in bold:
GCAGCAGGATCCGCCATCATGGTCAT-
GAGGCCCCTGTGGAGTCTGCTTCT C (SEQ ID NO: 22) and a 3' primer, containing a Xba restriction site shown in bold:
GCAGCATCTAGAATCTTTGTAGGAGC-
CTTCCCTGGTGCTGCCTC (SEQ ID NO: 25). This construct will express the predicted extracellular domain of D-SLAM fused to Fc in pA2.

These two above constructs were expressed in their appropriate host cells (e.g., pC4 in a mammalian system, while pA2 in a baculovirus system), both systems produced a truncated protein, lacking the predicted signal sequence and beginning with A23 of SEQ ID NO:2. Thus, as was predicted, both baculovirus and mammalian systems process D-SLAM to amino acid A23 of SEQ ID NO:2. However, due to differences in glycosylation, the baculovirus system produces a protein, under reducing conditions, migrating at around 60 kD, while the mammalian system generates a protein migrating at around 55 kD.

Additionally, fusion proteins of D-SLAM polypeptides, including the predicted extracellular domain or the mature form of D-SLAM, can be fused to FLAG for mammalian cell expression. For example, the extracellular domain can be amplifed using the following primers: a 5' primer containing a BamHI restriction site shown in bold:
GCAGCAGGATCCGCCATCATGGTCAT-
GAGGCCCCTGTGGAGTCTGCTTCT C (SEQ ID NO: 22) and a 3' primer, containing a Xba restriction site shown in bold:
GCAGCATCTAGATTACTTGT-
CATCGTCGTCCTTGTAGTCATCTTTGTAGGAG
GCCTTCCCTGGTGCTG (SEQ ID NO: 26).

Example 11

Production of an Antibody a) Hybridoma Technology

The antibodies of the present invention can be prepared by a variety of methods. (See, Current Protocols, Chapter 2.) As one example of such methods, cells expressing D-SLAM is administered to an animal to induce the production of sera containing polyclonal antibodies. In a preferred method, a preparation of D-SLAM protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with D-SLAM polypeptide or, more preferably, with a secreted D-SLAM polypeptide-expressing cell. Such cells may be cultured in any suitable tissue culture medium; however, it is preferable to culture cells in Earle's modified Eagle's medium supplemented with 10% fetal bovine serum (inactivated at about 56 degree C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are-then assayed to identify clones which secrete antibodies capable of binding the D-SLAM polypeptide.

Alternatively, additional antibodies capable of binding to D-SLAM polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the D-SLAM protein-specific antibody can be blocked by D-SLAM. Such antibodies comprise anti-idiotypic antibodies to the D-SLAM protein-specific antibody and can be used to immunize an animal to induce formation of further D-SLAM protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted D-SLAM protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of antibody fragments directed against D-SLAM from a library of scFvs.

Naturally occuring V-genes isolated from human PBLs are constructed into a large library of antibody fragments which contain reactivities against D-SLAM to which the donor may or may not have been exposed (see e.g., U.S. Pat. No. 5,885,793 incorporated herein in its entirety by reference).

Rescue of the Library

A library of scFvs is constructed from the RNA of human PBLs as described in WO92/01047. To rescue phage displaying antibody fragments, approximately $10^9$ E. coli harbouring the phagemid are used to inoculate 50 mil of 2×TY containing 1% glucose and 100 ug/mil of ampicillin (2×TY-AMP-GLU) and grown to an O.D. of 0.8 with shaking. Five ml of this culture is used to innoculate 50 ml of 2×TY-AMP-GLU, $2×10^8$ TU of delta gene 3 helper (M13 delta gene III, see WO92/01047) are added and the culture incubated at 37 degree C. for 45 minutes without shaking and then at 37 degree C. for 45 minutes with shaking. The culture is centrifuged at 4000 r.p.m. for 10 min. and the pellet resuspended in 2 liters of of 2×TY containing 100 ug/mi ampicillin and 50 ug/ml kanamycin and grown overnight. Phage are prepared as described in WO92/01047.

M13 delta gene III is prepared as follows: M13 delta gene III helper phage does not encode gene III protein, hence the phage (mid) displaying antibody fragments have a greater avidity of binding to antigen. Infectious M13 delta gene III particles are made by growing the helper phage in cells harbouring a pUC19 derivative supplying the wild type gene III protein during phage morphogenesis. The culture is incubated for 1 hour at 37 degree C. without shaking and then for a further hour at 37 degree C. with shaking. Cells are spun down (IEC-Centra 8, 4000 revs/min for 10 min), resuspended in 300 ml 2×TY broth containing 100 ug ampicillin/ml and 25 ug kanamycin/mil (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the Library

Immunotubes (Nunc) are coated overnight in PBS with 4 ml of either 100 ug/ml or 10 ug/ml of a polypeptide of the present invention. Tubes are blocked with 2% Marvel-PBS for 2 hours at 37 degree C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylarnine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37 degree C. The E. coli are then plated on TYE plates containing 1% glucose and 100 ug/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 12

Production Of D-SLAM Protein For High-Throughput Screening Assays

The following protocol produces a supernatant containing D-SLAM polypeptide to be tested. This supernatant can then be used in the Screening Assays described in Examples 14–21.

First, dilute Poly-D-Lysine (644 587 Boehringer-Mannheim) stock solution (1 mg/ml in PBS) 1:20 in PBS (w/o calcium or magnesium 17–516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2×10^5$ cells/well in 0.5 ml DMEM(Dulbecco's Modified Eagle Medium)(with 4.5 G/L glucose and L-glutamine (12–604F Biowhittaker))/10% heat inactivated FBS(14–503F Biowhittaker)/1×Penstrep(17–602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8–10, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37 degree C. for 6 hours.

While cells are incubating, prepare appropriate media, either 1% BSA in DMEM with 1× penstrep, or HGS CHO-5 media (116.6 mg/L of CaCl2 (anhyd); 0.00130 mg/L $CuSO_4$–$5H_2O$; 0.050 mg/L of $Fe(NO_3)_3$–$9H_2O$; 0.417 mg/L of $FeSO_4$–$7H_2O$; 311.80 mg/L of Kcl; 28.64 mg/L of $MgCl_2$;48.84 mg/L of $MgSO_4$;6995.50 mg/L of NaCl; 2400.0 mg/L of $NaHCO_3$; 62.50 mg/L of $NaH_2PO_4$-$H_2O$; 71.02 mg/L of $Na_2HPO4$; 0.4320 mg/L of $ZnSO_4$–$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/mil of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm) with 2 mm glutamine and 1× penstrep. (BSA (81-068-3 Bayer) 100 gm dissolved in 1L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degree C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 14–21.

It is specifically understood that when activity is obtained in any of the assays described below using a supernatant, the activity originates from either the D-SLAM polypeptide directly (e.g., as a secreted protein) or by D-SLAM inducing expression of other proteins, which are then secreted into the supernatant. Thus, the invention further provides a method of identifying the protein in the supernatant characterized by an activity in a particular assay.

Example 13

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proxial region encoding Trp-Ser-Xxx-Trp-Ser (SEQ ID NO:5)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

|  | | JAKs | | | | |
| --- | --- | --- | --- | --- | --- | --- |
| Ligand | tyk2 | Jak1 | Jak2 | Jak3 | STATS | GAS (elements) or ISRE |
| IFN family | | | | | | |
| IFN-a/B | + | + | − | − | 1, 2, 3 | ISRE |
| IFN-g | | + | + | − | 1 | GAS (IRF1 > Lys6 > IFP) |
| Il-10 | + | ? | ? | − | 1, 3 | |
| gp130 family | | | | | | |
| IL-6 (Pleiotrohic) | + | + | + | ? | 1, 3 | GAS (IRF1 > Lys6 > IFP) |
| Il-11 (Pleiotrohic) | ? | + | ? | ? | 1, 3 | |
| OnM (Pleiotrohic) | ? | + | + | ? | 1, 3 | |
| LIF (Pleiotrohic) | ? | + | + | ? | 1, 3 | |
| CNTF (Pleiotrohic) | −/+ | + | + | ? | 1, 3 | |
| G-CSF (Pleiotrohic) | ? | + | ? | ? | 1, 3 | |
| IL-12 (Pleiotrohic) | + | − | + | + | 1, 3 | |
| g-C family | | | | | | |
| IL-2 (lymphocytes) | − | + | − | + | 1, 3, 5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1, 3, 5 | |
| EPO | ? | − | + | − | 5 | GAS (B-CAS > IRF1 = IFP >> Ly6) |
| Receptor Tyrosine Kinases | | | | | | |
| EGF | ? | + | + | − | 1, 3 | GAS (IRF1) |
| PDGF | ? | + | + | − | 1, 3 | |
| CSF-1 | ? | + | + | − | 1, 3 | GAS (not IRF1) |

To construct a synthetic GAS containing promoter element, which is used in the Biological Assays described in Examples 14–15, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:

(SEQ ID NO:6)
5':GCGCCTCGAGATTTCCCCGAAATCTAGATTTCCCCGAAATGATTTCCC
CGAAATGATTTCCCCGAAATATCTGCCATCTCAATTAG:3'

The downstream primer is complementary to the SV40 promoter and is flanked with a Hind III site: 5':GCG-GCAAGCTTTTTGCAAAGCCTAGGC:3' (SEQ ID NO:7)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

(SEQ ID NO:8)
5':CTCGAGATTTCCCCGAAATCTAGATTTCCCCGAAATGATTTCCCCG

AAATGATTTCCCCGAAATATCTGCCATCTCAATTAGTCAGCAACCATAGTC

CCGCCCCTAACTCCGCCCATCCCGCCCCTAACTCCGCCCAGTTCCGCCCAT

TCTCCGCCCCATGGCTGACTAATTTTTTTTATTTATGCAGAGGCCGAGGCC

GCCTCGGCCTCTGAGCTATTCCAGAAGTAGTGAGGAGGCTTTTTTGGAGGC

CTAGGCTTTTGCAAAAAGCTT:3'

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 14–15.

Other constructs can be made using the above description and replacing GAS with a different promoter sequence. For example, construction of reporter molecules containing NFK-B and EGR promoter sequences are described in Examples 16 and 17. However, many other promoters can be substituted using the protocols described in these Examples. For instance, SRE, IL-2, NFAT, or Osteocalcin promoters can be substituted, alone or in combination (e.g., GAS/NF—KB/EGR, GAS/NF—KB, Il-2/NFAT, or NF—KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 14

High-Throughput Screening Assay for T-cell Activity

The following protocol is used to assess T-cell activity of D-SLAM by determining whether D-SLAM supernatant proliferates and/or differentiates T-cells. T-cell activity is assessed using the GAS/SEAP/Neo construct produced in Example 13. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI +10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37 degree C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing D-SLAM polypeptides or D-SLAM induced polypeptides as produced by the protocol described in Example 12.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100, 000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H 11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20 degree C. until SEAP assays are performed according to Example 18. The plates containing the remaining treated cells are placed at 4 degree C. and serve as a source of material for repeating the assay on a specific well if desired.

As a positive control, 100 Unit/ml interferon gamma can be used which is known to activate Jurkat T cells. Over 30 fold induction is typically observed in the positive control wells.

Example 15

High-Throughput Screening Assay Identifying Myeloid Activity

The following protocol is used to assess myeloid activity of D-SLAM by determining whether D-SLAM proliferates and/or differentiates myeloid cells. Myeloid cell activity is assessed using the GAS/SEAP/Neo construct produced in Example 13. Thus, factors that increase SEAP activity indicate the ability to activate the Jaks-STATS signal transduction pathway. The myeloid cell used in this assay is U937, a pre-momocyte cell line, although TF-1, HL60, or KG1 can be used.

To transiently transfect U937 cells with the GAS/SEAP/Neo construct produced in Example 13, a DEAE-Dextran method (Kharbanda et. al., 1994, Cell Growth & Differentiation, 5:259–265) is used. First, harvest 2×10e7 U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4 \cdot 7H_2O$, 1 mM $MgCl_2$, and 675 uM $CaCl_2$. Incubate at 37 degree C. for 45 min.

Wash the cells with RPMI 1640 medium containing 10% FBS and then resuspend in 10 ml complete medium and incubate at 37 degree C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 ul cells per well in the 96-well plate (or $1 \times 10^5$ cells/well).

Add 50 ul of the supernatant prepared by the protocol described in Example 12. Incubate at 37 degee C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 18.

Example 16

High-Throughput Screening Assay Identifying Neuronal Activity.

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by D-SLAM.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by D-SLAM can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

```
                                              (SEQ ID NO:9)
5' GCGCTCGAGGGATGACAGCGATAGAACCCCGG-3'

(SEQ ID NO:10)
5' GCGAAGCTTCGCGACTCCCCGGATCCGCCTC-3'
```

Using the GAS:SEAP/Neo vector produced in Example 13, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08–115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 12. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as 5×105 cells/ml.

Add 200 ul of the cell suspension to each well of 96-well plate (equivalent to 1×105 cells/well). Add 50 ul supernatant produced by Example 12, 37 degree C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 18.

Example 17

High-Throughput Screening Assay for T-cell Activity

NF—KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF—KB regulates the expression of genes involved in immune cell activation, control of apoptosis (NF—KB appears to shield cells from apoptosis), B and T-cell development, anti-viral and antimicrobial responses, and multiple stress responses.

In non-stimulated conditions, NF—KB is retained in the cytoplasm with I—KB (Inhibitor KB). However, upon stimulation, I—KB is phosphorylated and degraded, causing NF—KB to shuttle to the nucleus, thereby activating transcription of target genes. Target genes activated by NF—KB include IL-2, IL-6, GM-CSF, ICAM-1 and class 1 MHC.

Due to its central role and ability to respond to a range of stimuli, reporter constructs utilizing the NF—KB promoter element are used to screen the supernatants produced in Example 12. Activators or inhibitors of NF—KB would be useful in treating diseases. For example, inhibitors of NF—KB could be used to treat those diseases related to the acute or chronic activation of NF—KB, such as rheumatoid arthritis.

To construct a vector containing the NF—KB promoter element, a PCR based strategy is employed. The upstream primer contains four tandem copies of the NF—KB binding site (GGGGACTTTCCC) (SEQ ID NO:11), 18 bp of sequence complementary to the 5' end of the SV40 early promoter sequence, and is flanked with an XhoI site:

(SEQ ID NO:12)
5':GCGGCCTCGAGGGGACTTTCCCGGGGACTTTCCGGGGACTTTCCGGG

ACTTTCCATCCTGCCATCTCAATTAG:3'

The downstream primer is complementary to the 3' end of the SV40 promoter and is flanked with a Hind III site:
5' :GCGGCAAGCTTTTTGCAAAGCCTAGGC:3' (SEQ ID NO:7)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

(SEQ ID NO:13)
5':CTCGAGGGGACTTTCCCGGGGACTTTCCGGGGACTTTCCGGGACTTT

CCATCTGCCATCTCAATTAGTCAGCAACCATAGTCCCGCCCCTAACTCCG

CCCATCCCGCCCCTAACTCCGCCCAGTTCCGCCCATTCTCCGCCCCATGG

CTGACTAATTTTTTTTATTTATGCAGAGGCCGAGGCCGCCTCGGCCTCTG

AGCTATTCCAGAAGTAGTGAGGAGGCTTTTTTGGAGGCCTAGGCTTTTGC

AAAAAGCTT:3'.

Next, replace the SV40 minimal promoter element present in the pSEAP2-promoter plasmid (Clontech) with this NF—KB/SV40 fragment using XhoI and HindIII. However, this vector does not contain a neomycin resistance gene, and therefore, is not preferred for mammalian expression systems.

In order to generate stable mammalian cell lines, the NF—KB/SV40/SEAP cassette is removed from the above NF—KB/SEAP vector using restriction enzymes SalI and NotI, and inserted into a vector containing neomycin resistance. Particularly, the NF—KB/SV40/SEAP cassette was inserted into pGFP-1 (Clontech), replacing the GFP gene, after restricting pGFP-1 with SalI and NotI.

Once NF—KB/SV40/SEAP/Neo vector is created, stable Jurkat T-cells are created and maintained according to the protocol described in Example 14. Similarly, the method for assaying supernatants with these stable Jurkat T-cells is also described in Example 14. As a positive control, exogenous TNF alpha (0.1, 1, 10 ng) is added to wells H9, H10, and H11, with a 5–10 fold activation typically observed.

Example 18

Assay for SEAP Activity

As a reporter molecule for the assays described in Examples 14–17, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 ul of 2.5× dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 μl Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| | Reaction Buffer Formulation: | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 19

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-3, used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-3 is made in 10% pluronic acid DMSO. To load the cells with fluo-3, 50 ul of 12 ug/ml fluo-3 is added to each well. The plate is incubated at 37 degree C. in a $CO_2$ incubator for 60 min. The plate is washed four times in the Biotek washer with HBSS leaving 100 ul of buffer.

For non-adherent cells, the cells are spun down from culture media. Cells are re-suspended to $2-5 \times 10^6$ cells/ml with HBSS in a 50-ml conical tube. 4 ul of 1 mg/ml fluo-3 solution in 10% pluronic acid DMSO is added to each ml of cell suspension. The tube is then placed in a 37 degree C. water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-3. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event caused by the a molecule, either D-SLAM or a molecule induced by D-SLAM, which has resulted in an increase in the intracellular $Ca^{++}$ concentration.

Example 20

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether D-SLAM or a molecule induced by D-SLAM is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 12, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (# 1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degree C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2–p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$(5 mM ATP/50 mM $MgCl_2$), then 10 ul of 5× Assay Buffer (40 mM imidazole hydrochloride, pH7.3, 40 mM beta-glycerophosphate, 1 mM EGTA, 100 mM $MgCl_2$, 5 mM $MnCl_2$, 0.5 mg/ml BSA), then 5 ul of Sodium Vanadate(1 mM), and then 5 ul of water. Mix the components gently and preincubate the reaction mix at 30 degree C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degree C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase(anti-P-Tyr-POD(0.5 u/ml)) to each well and incubate at 37 degree C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 21

High-Throughput Screening Assay Identifying Phosphorylation Activity

As a potential alternative and/or compliment to the assay of protein tyrosine kinase activity described in Example 20, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degree C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 12 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation by D-SLAM or a molecule induced by D-SLAM.

Example 22

Method of Determining Alterations in the D-SLAM Gene

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degree C. for 30 seconds; 60–120 seconds at 52–58 degree C.; and 60–120 seconds at 70 degree C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of D-SLAM is also determined and genomic PCR products analyzed to confirm the results. PCR products harboring suspected mutations in D-SLAM is then cloned and sequenced to validate the results of the direct sequencing.

PCR products of D-SLAM are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in D-SLAM not present in unaffected individuals.

Genomic rearrangements are also observed as a method of determining alterations in the D-SLAM gene. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the D-SLAM genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of D-SLAM (hybridized by the probe) are identified as insertions, deletions, and translocations. These D-SLAM alterations are used as a diagnostic marker for an associated disease.

Example 23

Method of Detecting Abnormal Levels of D-SLAM in a Biological Sample

D-SLAM polypeptides can be detected in a biological sample, and if an increased or decreased level of D-SLAM is detected, this polypeptide is a marker for a particular phenotype. Methods of detection are numerous, and thus, it is understood that one skilled in the art can modify the following assay to fit their particular needs.

For example, antibody-sandwich ELISAs are used to detect D-SLAM in a sample, preferably a biological sample. Wells of a microtiter plate are coated with specific antibodies to D-SLAM, at a final concentration of 0.2 to 10 ug/ml. The antibodies are either monoclonal or polyclonal and are produced by the method described in Example 11. The wells are blocked so that non-specific binding of D-SLAM to the well is reduced.

The coated wells are then incubated for >2 hours at RT with a sample containing D-SLAM. Preferably, serial dilutions of the sample should be used to validate results. The plates are then washed three times with deionized or distilled water to remove unbounded D-SLAM.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot D-SLAM polypeptide concentration on the X-axis (log scale) and fluorescence or absorbance of the Y-axis (linear scale). Interpolate the concentration of the D-SLAM in the sample using the standard curve.

Example 24

Formulating a Polypeptide

The D-SLAM composition will be formulated and dosed in a fashion consistent with good medical practice, taking into account the clinical condition of the individual patient (especially the side effects of treatment with the D-SLAM polypeptide alone), the site of delivery, the method of administration, the scheduling of administration, and other factors known to practitioners. The "effective amount" for purposes herein is thus determined by such considerations.

As a general proposition, the total pharmaceutically effective amount of D-SLAM administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, D-SLAM is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing D-SLAM are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

D-SLAM is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(−)-3-hydroxybutyric acid (EP 133,988). Sustained-release compositions also include liposomally entrapped D-SLAM polypeptides. Liposomes containing the D-SLAM are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, D-SLAM is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting D-SLAM uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamnic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

D-SLAM is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

D-SLAM used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

D-SLAM polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous D-SLAM polypeptide solution, and the resulting mixture is lyophilized. The infusion solution is prepared by reconstituting the lyophilized D-SLAM polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, D-SLAM may be employed in conjunction with other therapeutic compounds.

The compositions of the invention may be administered alone or in combination with other therapeutic agents. Therapeutic agents that may be administered in combination with the compositions of the invention, include but not limited to, other members of the TNF family, chemotherapeutic agents, antibiotics, steroidal and non-sterodial anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

Example 25

Method of Treating Decreased Levels of D-SLAM

The present invention relates to a method for treating an individual in need of a decreased level of D-SLAM activity in the body comprising, administering to such an individual a composition comprising a therapeutically effective amount of D-SLAM antagonist. Preferred antagonists for use in the present invention are D-SLAM-specific antibodies.

Moreover, it will be appreciated that conditions caused by a decrease in the standard or normal expression level of D-SLAM in an individual can be treated by administering D-SLAM, preferably in the secreted form. Thus, the invention also provides a method of treatment of an individual in need of an increased level of D-SLAM polypeptide comprising administering to such an individual a pharmaceutical composition comprising an amount of D-SLAM to increase the activity level of D-SLAM in such an individual.

For example, a patient with decreased levels of D-SLAM polypeptide receives a daily dose 0.1–100 ug/kg of the polypeptide for six consecutive days. Preferably, the polypeptide is in the secreted form. The exact details of the dosing scheme, based on administration and formulation, are provided in Example 24.

Example 26

Method of Treating Increased Levels of D-SLAM

The present invention also relates to a method for treating an individual in need of an increased level of D-SLAM activity in the body comprising administering to such an individual a composition comprising a therapeutically effective amount of D-SLAM or an agonist thereof.

Antisense technology is used to inhibit production of D-SLAM. This technology is one example of a method of decreasing levels of D-SLAM polypeptide, preferably a secreted form, due to a variety of etiologies, such as cancer.

For example, a patient diagnosed with abnormally increased levels of D-SLAM is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 24.

Example 27

Method of Treatment Using Gene Therapy-Ex Vivo

One method of gene therapy transplants fibroblasts, which are capable of expressing D-SLAM polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding D-SLAM can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted D-SLAM.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the D-SLAM gene is then added to the media and the packaging cells transduced with the vector. The packaging cells now produce infectious viral particles containing the D-SLAM gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether D-SLAM protein is produced.

The engineered fibroblasts are then transplanted onto the host, either alone or after having been grown to confluence on cytodex 3 microcarrier beads.

Example 28

Gene Therapy Using Endogenous D-SLAM Gene

Another method of gene therapy according to the present invention involves operably associating the endogenous D-SLAM sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous D-SLAM, flanking the promoter. The targeting sequence will be sufficiently near the 5' end of D-SLAM so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous D-SLAM sequence. This results in the expression of D-SLAM in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the D-SLAM locus, plasmid pUC18 (MBI Fermentas, Amherst, N.Y.) is digested with HindIII. The CMV promoter is amplified by PCR with an XbaI site on the 5'end and a BamHI site on the 3' end. Two D-SLAM non-coding sequences are amplified via PCR: one D-SLAM non-coding sequence (D-SLAM fragment 1) is amplified with a HindIII site at the 5' end and an Xba site at the 3'end; the other D-SLAM non-coding sequence (D-SLAM fragment 2) is amplified with a BamHI site at the 5'end and a HindIII site at the 3'end. The CMV promoter and D-SLAM fragments are digested with the appropriate enzymes (CMV promoter—XbaI and BamHI; D-SLAM fragment 1—XbaI; D-SLAM fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5. \times 10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 29

Method of Treatment Using Gene Therapy-In Vivo

Another aspect of the present invention is using in vivo gene therapy methods to treat disorders, diseases and conditions. The gene therapy method relates to the introduction of naked nucleic acid (DNA, RNA, and antisense DNA or RNA) D-SLAM sequences into an animal to increase or decrease the expression of the D-SLAM polypeptide. The D-SLAM polynucleotide may be operatively linked to a promoter or any other genetic elements necessary for the expression of the D-SLAM polypeptide by the target tissue.

Such gene therapy and delivery techniques and methods are known in the art, see, for example, WO 90/11092, WO 98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The D-SLAM polynucleotide constructs may be delivered by any method that delivers injectable materials to the cells of an animal, such as, injection into the interstitial space of tissues (heart, muscle, skin, lung, liver, intestine and the like). The D-SLAM polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the D-SLAM polynucleotides may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The D-SLAM polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The D-SLAM polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked D-SLAM polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked D-SLAM polynucleotide constructs can be delivered to arteries during angioplasty by the catheter used in the procedure.

The dose response effects of injected D-SLAM polynucleotide in muscle in vivo is determined as follows. Suitable D-SLAM template DNA for production of mRNA coding for D-SLAM polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The D-SLAM template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for D-SLAM protein expression. A time course for D-SLAM protein expression may be done in a similar fashion except that quadriceps from different mice are harvested at different times. Persistence of D-SLAM DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using D-SLAM naked DNA.

Example 30

D-SLAM Transgenic Animals.

The D-SLAM polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol.

40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Any of the D-SLAM polypeptides disclose throughout this application can be used to generate transgenic animals. For example, DNA encoding amino acids M1–K232 of SEQ ID NO:2 can be inserted into a vector containing a promoter, such as the actin promoter, which will ubiquitously express the inserted fragment. Primers that can be used to generate such fragments include a 5' primer containing a BamHI restriction site shown in bold:
G C A G C A G G A T C C G C C A T C A T G G T C AT-GAGGCCCCTGTGGAGTCTGCTTCT C (SEQ ID NO: 22) and a 3' primer, containing a Xba restriction site shown in bold:
G C A G C A T C T A G A T T A T T T G T A G G A G G C-CTTCCCTGGTGCTGCCTC (SEQ ID NO: 24). This construct will express the predicted extracellular domain of D-SLAM under the control of the actin promoter for ubiquitous expression. The region of D-SLAM included in this construct extends from M1–K232 of SEQ ID NO:2.

Similarly, the DNA encoding the full length D-SLAM protein can also be inserted into a vector using the following primers: A 5' primer containing a BamHI restriction site shown in bold:
G C A G C A G G A T C C G C C A T C A T G G T C AT-GAGGCCCCTGTGGAGTCTGCTTCT C (SEQ ID NO: 22) and a 3' primer, containing a Xba restriction site shown in bold:
G C A G C A T C T A G A T T A T G G C A G A T C C T G-CACAAGGGGGTTCTCTGTC (SEQ ID NO: 23). Besides these two examples, other fragments of D-SLAM can also be inserted into a vector to create transgenics having ubiquitous expression.

Alternatively, polynucleotides of the invention can be inserted in a vector which controls tissue specific expression through a tissue specific promoter. For example, a construct having a transferrin promoter would express the D-SLAM polypeptide in the liver of transgenic animals. Therefore, DNA encoding amino acids M1–K232 of SEQ ID NO:2 can be amplified using a 5' primer, having a BamHI restriction site shown in bold:
G C A G C A G G A T C C G C C A T C A T G G T C AT-GAGGCCCCTGTGGAGTCTGCTTCT C (SEQ ID NO: 22), and a 3' primer, containing a Xba restriction site shown in bold:
G C A G C A T C T A G A T T A T T T G T A G G A G G C-CTTCCCTGGTGCTGCCTC (SEQ ID NO: 24).

Similarly, the DNA encoding the full length D-SLAM protein can also be inserted into a vector for tissue specific expression using the following primers: A 5' primer containing a BaniHI restriction site shown in bold:
G C A G C A G G A T C C G C C A T C A T G G T C AT-GAGGCCCCTGTGGAGTCTGCTTCT C (SEQ ID NO: 22) and a 3' primer, containing a Xba restriction site shown in bold:
G C A G C A T C T A G A T T A T G G C A G A T C C T G-CACAAGGGGGTTCTCTGTC (SEQ ID NO: 23).

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of D-SLAM polypeptides, studying conditions and/or disorders associated with aberrant D-SLAM expression, and in screening for compounds effective in ameliorating such conditions and/or disorders.

Example 31

D-SLAM Knock-Out Animals.

Endogenous D-SLAM gene expression can also be reduced by inactivating or "knocking out" the D-SLAM gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the D-SLAM polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of D-SLAM polypeptides, studying conditions and/or disorders associated with aberrant D-SLAM expression, and in screening for compounds effective in ameliorating such conditions and/or disorders.

Example 32

Assays Detecting Stimulation or Inhibition of B cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay

Purified D-SLAM protein, or truncated forms thereof, is assessed for its ability to induce activation, proliferation, differentiation or inhibition and/or death in B-cell populations and their precursors. The activity of D-SLAM protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5 \times 10^{-5}$ M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay

BALB/c mice are injected (i.p.) twice per day with buffer only, or 2 mg/Kg of D-SLAM protein, or truncated forms thereof. Mice receive this treatment for 4 consecutive days, at which time they are sacrificed and various tissues and serum collected for analyses. Comparison of H&E sections from normal and D-SLAM protein-treated spleens identify the results of the activity of D-SLAM protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from D-SLAM protein-treated mice is used to indicate whether D-SLAM protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and D-SLAM protein-treated mice.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 33

T Cell Proliferation Assay

A CD3-induced proliferation assay is performed on PBMCs and is measured by the uptake of $^3$H-thymidine. The assay is performed as follows. Ninety-six well plates are coated with 100 µl/well of mAb to CD3 (HIT3a, Pharmingen) or isotype-matched control mAb (B33.1) overnight at 4 degree C. (1 µg/ml in 0.05M bicarbonate buffer, pH 9.5), then washed three times with PBS. PBMC are isolated by F/H gradient centrifugation from human peripheral blood and added to quadruplicate wells ($5 \times 10^4$/well) of mAb coated plates in RPMI containing 10% FCS and P/S in the presence of varying concentrations of D-SLAM protein (total volume 200 µl). Relevant protein buffer and medium alone are controls. After 48 hr. culture at 37 degree C., plates are spun for 2 min. at 1000 rpm and 100 µl of supernatant is removed and stored −20 degree C. for measurement of IL-2 (or other cytokines) if effect on proliferation is observed. Wells are supplemented with 100 µl of medium containing 0.5 µCi of $^3$H-thymidine and cultured at 37 degree C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of D-SLAM proteins.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 34

Effect of D-SLAM on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD 1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of D-SLAM or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of D-SLAM for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the Expression of MHC Class II, Costimulatory and Adhesion Molecules

Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of D-SLAM or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte Activation and/or Increased Survival

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. D-SLAM, agonists, or antagonists of D-SLAM can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay

Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2 \times 10^6$/ml in PBS containing PI at a final concentration of 5 $\mu$g/ml, and then incubaed at room temperature for 5 minutes before FACScan analysis. PI uptake has been demonstrated to correlate with DNA fragmentation in this experimental paradigm.

Effect on Cytokine Release

An important function of monocytes/macrophages is their regulatory activity on other cellular populations of the immune system through the release of cytokines after stimulation. An ELISA to measure cytokine release is performed as follows. Human monocytes are incubated at a density of $5 \times 10^5$ cells/ml with increasing concentrations of D-SLAM and under the same conditions, but in the absence of D-SLAM. For IL-12 production, the cells are primed overnight with IFN (100 U/ml) in presence of D-SLAM. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

Oxidative Burst

Purified monocytes are plated in 96-w plate at $2-1 \times 10^5$ cell/well. Increasing concentrations of D-SLAM are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 $\mu$l 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Results

As shown below, D-SLAM appears to specifically bind monocyte-derived dendritic cells, while in this experiment, D-SLAM did not bind to monocytes, T cells, or a variety of cell lines.

|  | Mean fluorescence | |
|---|---|---|
|  | Control | D-SLAM |
| Dendritic cells | 3.94 | 10.95 |
| Monocytes | 3.18 | 3.18 |
| T cells | 10.84 | 10.85 |
| @CD3 activ. T cells | 5.94 | 5.93 |
| IM-9 | 4.1 | 4.51 |
| K562 | 2.65 | 2.89 |
| SupT13 | 2.63 | 3.76 |
| Jurkat | 3.37 | 3.62 |
| THP-1 | 3.92 | 4.71 |

Moreover, following incubation of dendritic cells with D-SLAM, an upregulation of a number of cell surface markers that are indicative of dendritic cell maturation or activation are observed (see below). Thus, D-SLAM may be involved in dendritic cell activation and maturation.

|  | Mean fluorescence | | | |
|---|---|---|---|---|
|  | Controls | HLA-DR | CD54 | CD86 | CD83 |
| Untreated | 6/5 | 1597 | 325 | 23 | 4 |
| D-SLAM 10 | 6/4 | 2432 | 488 | 43 | 5 |
| D-SLAM 100 | 5/3 | 3545 | 309 | 154 | 10 |
| D-SLAM 1000 | 8/3 | 2952 | 657 | 258 | 18 |

Additional data suggests that D-SLAM may induce TNF-alpha production by monocytes, and that D-SLAM may bind to itself in a homotypic association. Therefore, D-SLAM would likely activate any cell, including non-hematopoietic cells, such as stromal cells, having D-SLAM expressed on the cell surface.

Thus, activating/maturing dendritic cells by increasing the amount of D-SLAM in a patient could be useful in the treatment of cancer and modulating the immune response. For example, if increasing the amount of D-SLAM elevates cell surface expression of dendritic cell markers, such as CD83, immune responses against tumors may be activated. In such an instance, treatment of patients having tumors with a soluble version of D-SLAM could lead to upregulation of CD83 on dendritic cells and result in enhanced recognition of tumors leading to an enhanced rejection/killing of the tumor.

Example 35

D-SLAM Biological Effects

Astrocyte and Neuronal Assays●

Recombinant D-SLAM, expressed and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate D-SLAM's activity on these cells.

Moreover, previous reports describing the biological effects of FGF-2 (basic FGF) on cortical or hippocampal neurons in vitro have demonstrated increases in both neuron survival and neurite outgrowth (Walicke, P. et al., "Fibroblast growth factor promotes survival of dissociated hippocampal neurons and enhances neurite extension." *Proc. Natl. Acad. Sci. USA* 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of D-SLAM to induce neurite outgrowth can be compared to the response achieved with FGF-2 using, for example, a thymidine incorporation assay.

Fibroblast and Endothelial Cell Assays●

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or D-SLAM with or without I-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or D-SLAM with or without IL-1α for 24 hours. The supernatants are collected and assayed for IL-6 by ELISA kit (Endogen, Cambridge, Mass.).

Human lung fibroblasts are cultured with FGF-2 or D-SLAM for 3 days in basal medium before the addition of Alamar Blue to assess effects on growth of the fibroblasts. FGF-2 should show a stimulation at 10–2500 ng/ml which can be used to compare stimulation with D-SLAM.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, D-SLAM can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of D-SLAM is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if D-SLAM acts to prolong the survival of dopaminergic neurons, it would suggest that D-SLAM may be involved in Parkinson's Disease.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 36

The Effect of D-SLAM on the Growth of Vascular Endothelial Cells

On day 1, human umbilical vein endothelial cells (HUVEC) are seeded at 2–b×10$^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. D-SLAM protein of SEQ ID NO. 2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that D-SLAM may proliferate vascular endothelial cells.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 37

Stimulatory Effect of D-SLAM on the Proliferation of Vascular Endothelial Cells For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, VEGF$_{165}$ or D-SLAM in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512–518 (1994).

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 38

Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2–3LP. Then, the cells are pulsed with 10% calf serum and 6 mg/ml BrdUrd. After 24 h, immunocytochemuistry is performed by using BrdUrd Staining Kit (Zymed Laboratories). In brief, the cells are incubated with the biotinylated mouse anti-BrdUrd antibody at 4° C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6:271(36) :21985–21992 (1996).

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 39

Stimulation of Endothelial Migration

This example will be used to explore the possibility that D-SLAM may stimulate lymphatic endothelial cell migration.

Endothelial cell migration assays are performed using a 48 well microchemotaxis chamber (Neuroprobe Inc., Cabin John, MD; Falk, W., et al., J. Immunological Methods 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, 2.5×10$^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 40

Stimulation of Nitric Oxide Production by Endothelial Cells

Nitric oxide released by the vascular endothelium is believed to be a mediator of vascular endothelium relaxation. Thus, D-SLAM activity can be assayed by determining nitric oxide production by endothelial cells in response to D-SLAM.

Nitric oxide is measured in 96-well plates of confluent microvascular endothelial cells after 24 hours starvation and a subsequent 4 hr exposure to various levels of a positive control (such as VEGF-1) and D-SLAM. Nitric oxide in the medium is determined by use of the Griess reagent to measure total nitrite after reduction of nitric oxide-derived nitrate by nitrate reductase. The effect of D-SLAM on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

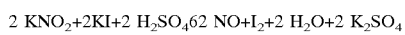

$$2\ KNO_2 + 2KI + 2\ H_2SO_4 \rightleftarrows 2\ NO + I_2 + 2\ H_2O + 2\ K_2SO_4$$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso—NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1 \times 10^6$ endothelial cells. All values reported are means of four to six measurements in each group (number of cell culture wells). See, Leak et al. *Biochem. and Biophys. Res. Comm.* 217:96–105 (1995).

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 41

Effect of D-SLAM on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or D-SLAM (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 42

Angiogenic Effect on Chick Chorioallantoic Membrane

Chick chorioallantoic membrane (CAM) is a well-established system to examine angiogenesis. Blood vessel formation on CAM is easily visible and quantifiable. The ability of D-SLAM to stimulate angiogenesis in CAM can be examined.

Fertilized eggs of the White Leghorn chick (*Gallus gallus*) and the Japanese qual (*Coturnix coturnix*) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 43

Angiogenesis Assay Using a Matrigel Implant in Mouse

In vivo angiogenesis assay of D-SLAM measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with D-SLAM at 150 ng/ml at 4 degree C. and drawn into cold 3 ml syringes. Female C57B1/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 44

Rescue of Ischemia in Rabbit Lower Limb Model

To study the in vivo effects of D-SLAM on ischemia, a rabbit hindlimb ischemia model is created by surgical removal of one femoral arteries as described previously (Takeshita, S. et al., *Am J. Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al. *Am J. Pathol* 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked D-SLAM expression plasmid by arterial gene transfer technology using a hydrogel-coated balloon catheter as described (Riessen, R. et al. *Hum Gene Ther.* 4:749–758 (1993); Leclerc, G. et al. *J. Clin. Invest.* 90:936–944 (1992)). When D-SLAM is used in the treatment, a single bolus of 500 mg D-SLAM protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 45

Effect of D-SLAM on Vasodilation

Since dilation of vascular endothelium is important in reducing blood pressure, the ability of D-SLAM to affect the blood pressure in spontaneously hypertensive rats (SHR) is examined. Increasing doses (0, 10, 30, 100, 300, and 900 mg/kg) of the D-SLAM are administered to 13–14 week old spontaneously hypertensive rats (SHR). Data are expressed as the mean +/− SEM. Statistical analysis are performed with a paired t-test and statistical significance is defined as $p<0.05$ vs. the response to buffer alone.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 46

Rat Ischemic Skin Flap Model

The evaluation parameters include skin blood flow, skin temperature, and factor VIII immunohistochemistry or endothelial alkaline phosphatase reaction. D-SLAM expression, during the skin ischemia, is studied using in situ hybridization.

The study in this model is divided into three parts as follows:
a) Ischemic skin
b) Ischemic skin wounds
c) Normal wounds The experimental protocol includes:
a) Raising a 3×4 cm, single pedicle full-thickness random skin flap (myocutaneous flap over the lower back of the animal).
b) An excisional wounding (4–6 mm in diameter) in the ischemic skin (skin-flap).
c) Topical treatment with D-SLAM of the excisional wounds (day 0, 1, 2, 3, 4 post-wounding) at the following various dosage ranges: 1 mg to 100 mg.
d) Harvesting the wound tissues at day 3, 5, 7, 10, 14 and 21 post-wounding for histological, immunohistochemical, and in situ studies.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 47

Peripheral Arterial Disease Model

Angiogenic therapy using D-SLAM is a novel therapeutic strategy to obtain restoration of blood flow around the ischemia in case of peripheral arterial diseases. The experimental protocol includes:
a) One side of the femoral artery is ligated to create ischemic muscle of the hindlimb, the other side of hindlimb serves as a control.
b) D-SLAM protein, in a dosage range of 20 mg–500 mg, is delivered intravenously and/or intramuscularly 3 times (perhaps more) per week for 2–3 weeks.
c) The ischemic muscle tissue is collected after ligation of the femoral artery at 1, 2, and 3 weeks for the analysis of D-SLAM expression and histology. Biopsy is also performed on the other side of normal muscle of the contralateral hindlimb.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 48

Ischemic Myocardial Disease Model

D-SLAM is evaluated as a potent mitogen capable of stimulating the development of collateral vessels, and restructuring new vessels after coronary artery occlusion. Alteration of D-SLAM expression is investigated in situ. The experimental protocol includes:

a) The heart is exposed through a left-side thoracotomy in the rat. Immediately, the left coronary artery is occluded with a thin suture (6-0) and the thorax is closed.

b) D-SLAM protein, in a dosage range of 20 mg–500 mg, is delivered intravenously and/or intramuscularly 3 times (perhaps more) per week for 2–4 weeks.

c) Thirty days after the surgery, the heart is removed and cross-sectioned for morphometric and in situ analyzes.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 49

Rat Corneal Wound Healing Model

This animal model shows the effect of D-SLAM on neovascularization. The experimental protocol includes:

a) Making a 1–1.5 mm long incision from the center of cornea into the stromal layer.

b) Inserting a spatula below the lip of the incision facing the outer corner of the eye.

c) Making a pocket (its base is 1–1.5 mm form the edge of the eye).

d) Positioning a pellet, containing 50 ng–5 ug of D-SLAM, within the pocket.

e) D-SLAM treatment can also be applied topically to the corneal wounds in a dosage range of 20 mg–500 mg (daily treatment for five days).

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 50

Diabetic Mouse and Glucocorticoid-Impaired Wound Healing Models

A. Diabetic db+/db+ Mouse Model.

To demonstrate that D-SLAM accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et al., *Lab Invest.* 40(4):460–473 (1979); Coleman, D. L., *Diabetes* 31 (Suppl): 1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

D-SLAM is administered using at a range different doses of D-SLAM, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) D-SLAM.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm$^2$, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with D-SLAM. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer served as a positive tissue control and human brain tissue is used as a negative tissue control. Each specimen included a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280–302 (1989); Wahl, S. M. et al., *J. Immunol.* 115:476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5:295–304 (1991); Haynes, B. F. et al., *J. Clin. Invest.* 61:703–797 (1978)) and producing a transient reduction of circulating monocytes (Haynes, B. F., et al., *J. Clin. Invest.* 61:703–797 (1978); Wahl, S. M., "Glucocorticoids and wound healing", In.: Antiinflammatory Steroid Action: Basic and Clinical Aspects, Academic Press, New York, pp. 280–302 (1989)). The systemic administration of steroids to impaired wound healing is a well establish phenomenon in rats (Beck, L. S. et al., *Growth Factors.* 5:295–304 (1991); Haynes, B. F., et al., *J. Clin. Invest.* 61:703–797 (1978); Wahl, S. M., "Glucocorticoids and wound healing", In: Antiinflammatory Steroid Action: Basic and Clinical Aspects, Academic Press, New York, pp. 280–302 (1989); Pierce, G. F. et al., *Proc. Natl. Acad. Sci. USA* 86:2229–2233 (1989)).

To demonstrate that D-SLAM can accelerate the healing process, the effects of multiple topical applications of D-SLAM on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemiic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

D-SLAM is administered using at a range different doses of D-SLAM, from 4 mg to 500 mg per wound per day for 8 days in vehicle. Vehicle control groups received 50 mL, of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) D-SLAM treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 mm$^2$, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with D-SLAM. A calibrated lens micrometer is used by a blinded observer to determine the distance of the wound gap.

Experimental data are analyzed using an unpaired t test. A p value of <0.05 is considered significant.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 51

Lymphadema Animal Model

The purpose of this experimental approach is to create an appropriate and consistent lymphedema model for testing the therapeutic effects of D-SLAM in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements

Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements

On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements

Blood is drawn, spun, and serum separated prior to surgery and then at conclusion for total protein and Ca2+ comparison.

Limb Weight Comparison

After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations

The transverse muscle located behind the knee (popliteal) area is dissected and arranged in a metal mold, filled with freezeGel, dipped into cold methylbutane, placed into labeled sample bags at −80 EC until sectioning. Upon sectioning, the muscle is observed under fluorescent microscopy for lymphatics.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 52

Suppression of TNF alpha-induced adhesion molecule expression by D-SLAM

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of D-SLAM to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% $CO_2$. HUVECs are seeded in 96-well plates at concentrations of $1\times10^4$ cells/well in EGM medium at 37 degree C. for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 µl of 0.1% paraformaldehyde-PBS(with Ca++ and Mg++) is added to each well. Plates are held at 4° C. for 30 min.

Fixative is then removed from the wells and wells are washed 1X with PBS(+Ca,Mg)+0.5% BSA and drained. Do not allow the wells to dry. Add 10 µl of diluted primary antibody to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed X3 with PBS (+Ca,Mg)+0.5% BSA.

Then add 20 µl of diluted ExtrAvidin-Alkaline Phosphotase (1:5,000 dilution) to each well and incubated at 37° C. for 30 min. Wells are washed X3 with PBS(+Ca,Mg)+0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 1:5,000 ($10^0$)>$10^{-05}$>$10^{-1}$>$10^{-15}$ 0.5 µl of each dilution is added to triplicate wells and the resulting AP content in each well is 5.50 ng, 1.74 ng, 0.55 ng, 0.18 ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Moreover, the sequence listing is herein incorporated by reference.

TABLE 1

| Res | Pos | Garni ... Alpha | Chou- ... Alpha | Garni ... Beta | Chou- ... Beta | Garni ... Turn | Chou- ... Turn | Garni ... Coil | Kyte- ... Hydro ... | Eisen ... Alpha | Eisen ... Beta | Karpl ... Flexi ... | James ... Antig ... | Emini Surfa ... |
|---|---|---|---|---|---|---|---|---|---|---|---|---|---|---|
| Met | 1 | . | . | B | . | . | . | . | -0.21 | * | . | . | -0.10 | 0.53 |
| Val | 2 | . | . | B | . | . | . | . | -0.63 | * | . | . | -0.10 | 0.65 |
| Met | 3 | . | . | B | . | . | . | . | -0.53 | * | . | . | -0.40 | 0.42 |
| Arg | 4 | . | . | B | . | . | T | . | -0.44 | * | * | . | -0.20 | 0.44 |
| Pro | 5 | . | . | B | . | . | T | . | -0.87 | * | . | . | -0.20 | 0.80 |
| Leu | 6 | . | . | . | . | T | T | . | -1.08 | * | * | . | 0.20 | 0.67 |
| Trp | 7 | . | . | B | . | . | T | . | -1.03 | * | . | . | -0.20 | 0.28 |
| Ser | 8 | . | A | B | . | . | . | . | -0.72 | * | * | . | -0.60 | 0.15 |
| Leu | 9 | . | A | B | . | . | . | . | -0.83 | * | * | . | -0.60 | 0.19 |
| Leu | 10 | . | A | B | . | . | . | . | -1.21 | . | . | . | -0.60 | 0.31 |
| Leu | 11 | . | A | B | . | . | . | . | -1.21 | . | . | . | -0.60 | 0.24 |
| Trp | 12 | . | A | B | . | . | . | . | -1.73 | . | . | . | -0.60 | 0.24 |
| Glu | 13 | . | A | B | . | . | . | . | -1.64 | . | . | . | -0.60 | 0.24 |
| Ala | 14 | . | A | B | . | . | . | . | -1.72 | . | . | . | -0.60 | 0.44 |
| Leu | 15 | . | A | B | . | . | . | . | -1.22 | . | * | . | -0.60 | 0.30 |
| Leu | 16 | . | A | B | . | . | . | . | -1.27 | . | * | . | -0.60 | 0.25 |
| Pro | 17 | . | A | B | . | . | . | . | -1.29 | . | * | . | -0.60 | 0.18 |

TABLE 1-continued

| Res | Pos | Garni ... Alpha | Chou- ... Alpha | Garni ... Beta | Chou- ... Beta | Garni ... Turn | Chou- ... Turn | Garni ... Coil | Kyte- ... Hydro ... | Eisen ... Alpha | Eisen ... Beta | Karpl ... Flexi | James ... Antig | Emini Surfa ... |
|---|---|---|---|---|---|---|---|---|---|---|---|---|---|---|
| Ile | 18 | . | . | B | B | . | . | . | −1.63 | . | * | . | −0.60 | 0.32 |
| Thr | 19 | . | . | B | B | . | . | . | −1.63 | . | . | . | −0.60 | 0.38 |
| Val | 20 | . | . | B | B | . | . | . | −0.82 | . | . | . | −0.60 | 0.25 |
| Thr | 21 | . | . | B | B | . | . | . | −0.87 | . | * | F | −0.45 | 0.61 |
| Gly | 22 | . | . | B | B | . | . | . | −1.47 | . | . | F | −0.45 | 0.32 |
| Ala | 23 | . | . | B | B | . | . | . | −0.88 | * | * | . | −0.60 | 0.35 |
| Gln | 24 | . | . | B | B | . | . | . | −0.52 | * | * | . | −0.60 | 0.33 |
| Val | 25 | . | . | B | B | . | . | . | −0.52 | * | . | . | −0.30 | 0.66 |
| Leu | 26 | . | . | B | B | . | . | . | −0.56 | * | * | . | −0.30 | 0.48 |
| Ser | 27 | . | . | B | B | . | . | . | −0.56 | * | * | F | −0.10 | 0.28 |
| Lys | 28 | . | . | B | B | . | . | . | −0.27 | * | * | F | −0.05 | 0.37 |
| Val | 29 | . | . | B | . | . | T | . | −1.12 | * | * | F | 1.00 | 0.60 |
| Gly | 30 | . | . | . | . | T | T | . | −1.08 | * | * | F | 1.45 | 0.33 |
| Gly | 31 | . | . | B | . | . | T | . | −1.08 | * | * | F | 0.50 | 0.14 |
| Ser | 32 | . | . | B | . | . | T | . | −1.63 | * | * | F | 0.15 | 0.15 |
| Val | 33 | . | A | B | . | . | . | . | −2.27 | . | * | . | −0.45 | 0.11 |
| Leu | 34 | . | A | B | . | . | . | . | −2.00 | * | * | . | −0.50 | 0.12 |
| Leu | 35 | . | A | B | . | . | . | . | −1.54 | * | * | . | −0.55 | 0.09 |
| Val | 36 | . | A | B | . | . | . | . | −1.41 | * | * | . | −0.60 | 0.23 |
| Ala | 37 | . | A | B | . | . | . | . | −1.32 | * | * | . | −0.60 | 0.43 |
| Ala | 38 | . | A | B | . | . | . | . | −0.81 | . | . | . | −0.30 | 0.81 |
| Arg | 39 | . | A | . | . | . | . | C | −0.70 | . | * | . | 0.65 | 1.08 |
| Pro | 40 | . | . | . | . | . | T | C | 0.11 | . | . | F | 0.45 | 0.93 |
| Pro | 41 | . | . | . | . | T | T | . | 0.11 | * | * | F | 1.40 | 1.59 |
| Gly | 42 | . | . | . | . | T | T | . | 0.81 | * | * | F | 0.65 | 0.60 |
| Phe | 43 | . | . | B | . | . | T | . | 1.40 | * | * | . | 0.10 | 0.76 |
| Gln | 44 | . | A | B | B | . | . | . | 0.70 | * | * | . | 0.30 | 0.86 |
| Val | 45 | . | A | B | B | . | . | . | 0.02 | . | * | . | 0.30 | 0.87 |
| Arg | 46 | . | A | B | B | . | . | . | −0.06 | * | * | . | −0.30 | 0.71 |
| Glu | 47 | . | A | B | . | . | . | . | 0.40 | * | * | . | −0.30 | 0.43 |
| Ala | 48 | . | A | B | . | . | . | . | 0.80 | * | * | . | 0.45 | 1.13 |
| Ile | 49 | . | A | . | . | T | . | . | −0.01 | * | * | . | 1.00 | 0.78 |
| Trp | 50 | . | A | . | . | T | . | . | 0.56 | * | . | . | 0.10 | 0.37 |
| Arg | 51 | . | A | . | . | . | . | C | 0.23 | * | . | . | −0.16 | 0.38 |
| Ser | 52 | . | . | . | . | . | . | C | −0.07 | * | . | . | 0.28 | 0.85 |
| Leu | 53 | . | . | . | . | . | . | C | 0.52 | * | . | F | 0.82 | 1.08 |
| Trp | 54 | . | . | . | . | . | T | C | 1.41 | * | . | F | 2.01 | 0.96 |
| Pro | 55 | . | . | . | . | . | T | C | 0.89 | * | . | F | 2.40 | 1.24 |
| Ser | 56 | . | . | . | . | . | T | C | −0.03 | * | . | F | 1.56 | 1.24 |
| Glu | 57 | . | . | . | . | . | T | C | −0.32 | . | . | F | 1.17 | 0.97 |
| Glu | 58 | . | A | B | . | . | . | . | 0.18 | . | . | F | 0.93 | 0.63 |
| Leu | 59 | . | A | B | . | . | . | . | −0.23 | . | . | . | 0.54 | 0.68 |
| Leu | 60 | . | A | B | . | . | . | . | −0.72 | * | . | . | −0.30 | 0.34 |
| Ala | 61 | . | A | B | . | . | . | . | −0.31 | * | . | . | −0.60 | 0.17 |
| Thr | 62 | . | A | B | . | . | . | . | −0.66 | * | * | . | −0.60 | 0.40 |
| Phe | 63 | . | A | B | . | . | . | . | −0.96 | * | * | . | −0.60 | 0.49 |
| Phe | 64 | . | . | B | . | . | T | . | −0.96 | * | * | . | 0.27 | 0.64 |
| Arg | 65 | . | . | . | . | . | T | C | −0.14 | * | * | F | 0.49 | 0.37 |
| Gly | 66 | . | . | . | . | . | T | C | 0.13 | * | * | F | 0.96 | 0.74 |
| Ser | 67 | . | . | . | . | . | T | C | −0.37 | * | * | F | 1.88 | 1.23 |
| Leu | 68 | . | . | . | . | . | . | C | 0.09 | * | * | F | 1.70 | 0.52 |
| Glu | 69 | . | . | . | . | . | . | C | 0.76 | * | * | F | 0.63 | 0.82 |
| Thr | 70 | . | . | B | . | . | . | . | 0.34 | * | . | . | 0.11 | 0.83 |
| Leu | 71 | . | . | B | . | . | . | . | 0.80 | . | * | . | 0.09 | 1.35 |
| Tyr | 72 | . | . | B | . | . | . | . | 0.40 | . | * | . | 0.82 | 1.53 |
| His | 73 | . | . | B | . | . | . | . | 0.40 | . | * | . | −0.40 | 0.92 |
| Ser | 74 | . | . | B | . | . | . | . | 0.06 | * | * | . | −0.40 | 0.92 |
| Arg | 75 | . | . | B | . | . | . | . | 0.48 | * | * | . | −0.40 | 0.58 |
| Phe | 76 | . | . | . | . | . | T | . | 0.70 | * | * | . | 0.90 | 0.83 |
| Leu | 77 | . | . | B | . | . | . | . | 0.94 | * | * | . | 0.50 | 0.63 |
| Gly | 78 | . | . | B | . | . | . | . | 0.17 | * | * | . | 0.50 | 0.56 |
| Arg | 79 | . | . | B | . | . | . | . | 0.43 | * | . | . | −0.40 | 0.53 |
| Ala | 80 | . | . | B | . | . | . | . | 0.02 | * | . | . | −0.10 | 0.87 |
| Gln | 81 | . | . | B | . | . | . | . | 0.72 | . | * | . | 0.65 | 1.18 |
| Leu | 82 | . | . | B | . | . | . | . | 0.72 | . | * | . | 0.50 | 0.97 |
| His | 83 | . | . | . | . | . | T | C | 0.77 | . | * | . | 0.00 | 0.79 |
| Ser | 84 | . | . | . | . | . | T | C | −0.16 | . | * | . | 0.00 | 0.61 |
| Asn | 85 | . | . | . | . | . | T | C | 0.43 | . | * | . | 0.00 | 0.61 |
| Leu | 86 | . | . | B | . | . | T | . | −0.38 | . | * | . | 0.10 | 0.78 |
| Ser | 87 | . | A | B | . | . | . | . | 0.09 | . | * | . | −0.30 | 0.48 |
| Leu | 88 | . | A | B | . | . | . | . | −0.09 | . | * | . | −0.30 | 0.30 |
| Glu | 89 | . | A | B | . | . | . | . | −0.60 | . | * | . | −0.30 | 0.55 |
| Leu | 90 | . | A | B | . | . | . | . | −0.60 | . | * | . | −0.30 | 0.34 |
| Gly | 91 | . | A | B | . | . | . | . | −0.09 | . | * | F | 0.45 | 0.72 |

TABLE 1-continued

| Res | Pos | Garni Alpha | Chou- Alpha | Garni Beta | Chou- Beta | Garni Turn | Chou- Turn | Garni Coil | Kyte- Hydro | Eisen Alpha | Eisen Beta | Karpl Flexi | James Antig | Emini Surfa |
|---|---|---|---|---|---|---|---|---|---|---|---|---|---|---|
| Pro | 92 | . | . | B | . | . | . | . | −0.13 | . | . | F | 0.65 | 0.55 |
| Leu | 93 | . | . | B | . | . | . | . | 0.68 | . | . | F | 0.39 | 0.66 |
| Glu | 94 | . | . | B | . | . | . | . | 0.38 | . | . | F | 1.78 | 1.12 |
| Ser | 95 | . | . | B | . | T | . | . | 0.84 | . | . | F | 2.37 | 0.97 |
| Gly | 96 | . | . | . | . | T | . | . | 1.19 | . | . | F | 2.86 | 1.17 |
| Asp | 97 | . | . | . | . | T | T | . | 0.70 | . | . | F | 3.40 | 1.08 |
| Ser | 98 | . | . | . | . | . | T | C | 1.21 | . | * | F | 2.41 | 0.70 |
| Gly | 99 | . | . | . | . | . | T | C | 0.36 | . | . | F | 2.07 | 0.95 |
| Asn | 100 | . | . | . | . | . | T | C | −0.16 | . | . | F | 1.13 | 0.42 |
| Phe | 101 | . | . | B | B | . | . | . | −0.41 | . | . | . | −0.26 | 0.26 |
| Ser | 102 | . | . | B | B | . | . | . | −1.27 | . | . | . | −0.60 | 0.26 |
| Val | 103 | . | . | B | B | . | . | . | −0.97 | . | * | . | −0.60 | 0.12 |
| Leu | 104 | . | . | B | B | . | . | . | −0.93 | . | * | . | −0.60 | 0.23 |
| Met | 105 | . | . | B | B | . | . | . | −0.82 | . | * | . | −0.26 | 0.25 |
| Val | 106 | . | . | B | B | . | . | . | −0.47 | . | * | . | 0.38 | 0.66 |
| Asp | 107 | . | . | B | . | . | T | . | −0.17 | . | * | F | 1.87 | 0.79 |
| Thr | 108 | . | . | . | . | T | T | . | 0.48 | . | * | F | 2.76 | 1.38 |
| Arg | 109 | . | . | . | . | T | T | . | 1.00 | . | * | F | 3.40 | 2.87 |
| Gly | 110 | . | . | . | . | . | T | C | 1.29 | . | * | F | 2.56 | 1.81 |
| Gln | 111 | . | . | . | . | . | T | C | 2.14 | . | * | F | 1.62 | 1.81 |
| Pro | 112 | . | . | . | . | . | T | C | 1.83 | . | * | F | 1.28 | 1.60 |
| Trp | 113 | . | . | . | . | T | T | . | 1.33 | * | * | F | 0.84 | 2.33 |
| Thr | 114 | . | . | B | . | . | T | . | 1.22 | . | * | F | 0.10 | 1.11 |
| Gln | 115 | . | . | B | B | . | . | . | 0.76 | . | * | F | −0.30 | 1.24 |
| Thr | 116 | . | . | B | B | . | . | . | 0.80 | . | * | F | −0.45 | 0.97 |
| Leu | 117 | . | . | B | B | . | . | . | 0.16 | . | * | F | 0.00 | 1.35 |
| Gln | 118 | . | . | B | B | . | . | . | 0.20 | . | * | . | −0.30 | 0.58 |
| Leu | 119 | . | . | B | B | . | . | . | 0.51 | . | * | . | −0.60 | 0.63 |
| Lys | 120 | . | . | B | B | . | . | . | −0.08 | * | * | . | −0.15 | 1.27 |
| Val | 121 | . | . | B | B | . | . | . | −0.62 | * | * | . | 0.30 | 0.74 |
| Tyr | 122 | . | . | B | B | . | . | . | −0.02 | * | * | . | −0.30 | 0.67 |
| Asp | 123 | . | . | B | B | . | . | . | 0.09 | * | * | . | 0.30 | 0.52 |
| Ala | 124 | . | . | B | . | . | . | . | 0.69 | * | . | . | 0.65 | 1.36 |
| Val | 125 | . | . | B | . | . | T | . | −0.21 | * | . | . | 0.85 | 1.34 |
| Pro | 126 | . | . | B | . | . | T | . | −0.21 | * | * | F | 0.85 | 0.60 |
| Arg | 127 | . | . | B | . | . | T | . | 0.03 | * | * | F | 0.25 | 0.44 |
| Pro | 128 | . | . | B | . | . | T | . | −0.82 | * | * | F | 0.40 | 1.02 |
| Val | 129 | . | . | B | B | . | . | . | −0.93 | * | * | . | −0.30 | 0.49 |
| Val | 130 | . | . | B | B | . | . | . | −0.97 | * | * | . | −0.60 | 0.22 |
| Gln | 131 | . | . | B | B | . | . | . | −1.34 | * | * | . | −0.60 | 0.10 |
| Val | 132 | . | . | B | B | . | . | . | −2.31 | * | * | . | −0.60 | 0.13 |
| Phe | 133 | . | . | B | B | . | . | . | −2.10 | * | . | . | −0.60 | 0.13 |
| Ile | 134 | . | . | B | B | . | . | . | −1.13 | * | . | . | −0.60 | 0.13 |
| Ala | 135 | . | . | B | B | . | . | . | −0.28 | * | * | . | −0.30 | 0.35 |
| Val | 136 | . | . | B | B | . | . | . | −0.87 | * | . | . | 0.30 | 0.68 |
| Glu | 137 | . | . | B | B | . | . | . | −0.01 | * | . | . | 0.60 | 0.98 |
| Arg | 138 | . | . | . | . | T | . | . | 0.48 | * | . | F | 1.84 | 1.69 |
| Asp | 139 | . | . | . | . | T | . | . | 1.07 | . | . | F | 2.18 | 3.51 |
| Ala | 140 | . | . | . | . | T | . | . | 1.70 | * | . | F | 2.52 | 2.72 |
| Gln | 141 | . | . | . | . | . | T | C | 2.24 | * | . | F | 2.86 | 2.78 |
| Pro | 142 | . | . | . | . | T | T | . | 1.58 | . | . | F | 3.40 | 2.40 |
| Ser | 143 | . | . | . | . | T | T | . | 1.47 | . | . | F | 2.76 | 1.27 |
| Lys | 144 | . | . | . | . | T | T | . | 0.61 | . | . | F | 2.42 | 1.27 |
| Thr | 145 | . | . | B | B | . | . | . | 0.50 | * | . | F | 1.13 | 0.61 |
| Cys | 146 | . | . | B | B | . | . | . | −0.31 | * | . | . | 0.04 | 0.39 |
| Gln | 147 | . | . | B | B | . | . | . | −0.40 | * | . | . | −0.60 | 0.16 |
| Val | 148 | . | . | B | B | . | . | . | −0.77 | * | . | . | −0.60 | 0.15 |
| Phe | 149 | . | . | B | B | . | . | . | −1.10 | * | . | . | −0.60 | 0.15 |
| Leu | 150 | . | . | B | B | . | . | . | −1.38 | . | . | . | −0.60 | 0.09 |
| Ser | 151 | . | . | B | B | . | . | . | −0.92 | . | . | . | −0.60 | 0.12 |
| Cys | 152 | . | . | . | B | T | . | . | −0.92 | . | . | . | −0.20 | 0.22 |
| Trp | 153 | . | . | . | B | T | . | . | −0.96 | . | . | . | −0.20 | 0.43 |
| Ala | 154 | . | . | . | . | . | T | C | −0.56 | * | . | . | 0.00 | 0.23 |
| Pro | 155 | . | . | . | . | . | T | C | 0.26 | * | . | . | 0.00 | 0.57 |
| Asn | 156 | . | . | . | . | . | T | C | −0.33 | * | . | F | 0.45 | 0.94 |
| Ile | 157 | . | . | B | . | . | T | . | 0.02 | * | . | F | 0.25 | 0.65 |
| Ser | 158 | . | . | B | B | . | . | . | 0.07 | * | . | F | −0.15 | 0.61 |
| Glu | 159 | . | . | B | B | . | . | . | 0.36 | * | . | F | −0.45 | 0.59 |
| Ile | 160 | . | . | B | B | . | . | . | 0.28 | * | * | . | −0.15 | 1.13 |
| Thr | 161 | . | . | B | B | . | . | . | 0.39 | * | * | . | −0.60 | 0.89 |
| Tyr | 162 | . | . | . | B | T | . | . | 1.39 | * | * | . | 0.25 | 1.00 |
| Ser | 163 | . | . | . | B | . | . | C | 1.69 | * | * | . | 0.05 | 2.80 |
| Trp | 164 | . | . | . | B | . | . | C | 1.38 | * | * | . | 0.95 | 3.36 |
| Arg | 165 | . | . | . | B | . | . | C | 1.96 | * | * | F | 1.40 | 3.10 |

TABLE 1-continued

| Res | Pos | Garni Alpha | Chou- Alpha | Garni Beta | Chou- Beta | Garni Turn | Chou- Turn | Garni Coil | Kyte- Hydro | Eisen Alpha | Eisen Beta | Karpl Flexi | James Antig | Emini Surfa |
|---|---|---|---|---|---|---|---|---|---|---|---|---|---|---|
| Arg | 166 | . | . | . | B | T | . | . | 1.67 | . | * | F | 2.20 | 3.34 |
| Glu | 167 | . | . | . | B | T | . | . | 1.91 | . | * | F | 2.20 | 3.14 |
| Thr | 168 | . | . | . | . | T | . | . | 1.51 | . | * | F | 3.00 | 2.68 |
| Thr | 169 | . | . | . | . | . | . | C | 1.46 | . | * | F | 2.50 | 1.18 |
| Met | 170 | . | . | . | . | . | . | C | 0.74 | . | * | . | 1.60 | 0.68 |
| Asp | 171 | . | . | . | . | T | . | . | 0.63 | . | * | . | 0.60 | 0.46 |
| Phe | 172 | . | . | B | . | . | . | C | 0.42 | . | * | . | 1.00 | 0.56 |
| Gly | 173 | . | . | . | . | . | . | C | 0.70 | . | * | . | 0.70 | 0.87 |
| Met | 174 | . | . | . | . | . | . | C | 0.71 | . | * | . | 0.70 | 0.71 |
| Glu | 175 | . | . | . | . | . | T | C | 0.50 | * | * | . | 0.45 | 1.10 |
| Pro | 176 | . | . | . | . | . | T | C | -0.20 | * | * | F | 0.45 | 0.91 |
| His | 177 | . | . | . | . | T | T | . | 0.19 | * | . | . | 0.20 | 0.80 |
| Ser | 178 | . | . | . | . | . | T | C | 0.53 | * | . | . | 0.30 | 0.67 |
| Leu | 179 | . | . | B | . | . | . | . | 0.79 | . | . | . | -0.10 | 0.72 |
| Phe | 180 | . | . | B | . | . | . | . | 0.79 | . | * | . | -0.10 | 0.52 |
| Thr | 181 | . | . | B | . | . | T | . | 0.14 | . | . | F | 0.25 | 0.68 |
| Asp | 182 | . | . | . | . | T | T | . | -0.63 | . | . | F | 0.35 | 0.61 |
| Gly | 183 | . | . | B | . | . | T | . | -0.63 | . | . | F | -0.05 | 0.58 |
| Gln | 184 | . | . | B | . | . | T | . | -0.71 | . | . | F | 0.25 | 0.54 |
| Val | 185 | . | . | B | B | . | . | . | -0.31 | . | . | . | -0.30 | 0.23 |
| Leu | 186 | . | . | B | B | . | . | . | -0.81 | . | . | . | -0.60 | 0.31 |
| Ser | 187 | . | . | B | B | . | . | . | -1.16 | . | . | . | -0.60 | 0.15 |
| Ile | 188 | . | . | B | B | . | . | . | -1.02 | . | . | . | -0.60 | 0.19 |
| Ser | 189 | . | . | B | . | . | . | . | -1.37 | . | . | . | -0.06 | 0.36 |
| Leu | 190 | . | . | B | . | . | . | . | -0.51 | * | * | . | 0.28 | 0.27 |
| Gly | 191 | . | . | . | . | . | T | C | 0.41 | . | * | F | 1.47 | 0.64 |
| Pro | 192 | . | . | . | . | . | T | C | 0.71 | . | . | F | 2.71 | 0.94 |
| Gly | 193 | . | . | . | . | T | T | . | 0.74 | . | . | F | 3.40 | 1.90 |
| Asp | 194 | . | . | . | . | T | T | . | 0.46 | * | . | F | 3.06 | 1.42 |
| Arg | 195 | . | . | B | B | . | . | . | 1.02 | * | . | F | 1.77 | 0.93 |
| Asp | 196 | . | . | B | B | . | . | . | 1.07 | * | . | F | 1.58 | 1.47 |
| Val | 197 | . | . | B | B | . | . | . | 0.61 | . | . | . | 1.09 | 1.18 |
| Ala | 198 | . | . | B | B | . | . | . | 0.07 | . | . | . | 0.30 | 0.32 |
| Tyr | 199 | . | . | B | B | . | . | . | -0.79 | . | . | . | -0.60 | 0.14 |
| Ser | 200 | . | . | B | B | . | . | . | -1.20 | . | . | . | -0.60 | 0.14 |
| Cys | 201 | . | . | B | B | . | . | . | -1.20 | . | . | . | -0.60 | 0.18 |
| Ile | 202 | . | . | B | B | . | . | . | -0.56 | . | . | . | -0.60 | 0.18 |
| Val | 203 | . | . | B | B | . | . | . | -0.82 | . | . | . | -0.60 | 0.21 |
| Ser | 204 | . | . | B | B | . | . | . | -0.88 | . | . | F | -0.45 | 0.29 |
| Asn | 205 | . | . | B | . | . | T | . | -0.87 | . | . | F | -0.05 | 0.56 |
| Pro | 206 | . | . | B | . | . | T | . | -0.20 | . | * | F | -0.05 | 0.80 |
| Val | 207 | . | . | . | . | T | T | . | -0.12 | . | * | F | 0.65 | 1.00 |
| Ser | 208 | . | . | . | . | T | T | . | 0.14 | . | * | . | 0.20 | 0.51 |
| Trp | 209 | . | . | B | . | . | . | . | 0.13 | . | . | . | -0.40 | 0.33 |
| Asp | 210 | . | . | B | . | . | . | . | -0.72 | . | . | . | -0.40 | 0.65 |
| Leu | 211 | . | . | B | B | . | . | . | -0.82 | . | * | . | -0.60 | 0.36 |
| Ala | 212 | . | . | B | B | . | . | . | -0.18 | . | * | . | -0.60 | 0.49 |
| Thr | 213 | . | . | B | B | . | . | . | -0.17 | . | . | . | -0.30 | 0.46 |
| Val | 214 | . | . | B | B | . | . | . | 0.12 | . | . | . | -0.60 | 0.58 |
| Thr | 215 | . | . | . | B | . | . | C | -0.18 | . | . | F | -0.25 | 0.96 |
| Pro | 216 | . | . | . | B | T | . | . | -0.03 | . | . | F | 0.25 | 0.89 |
| Trp | 217 | . | . | . | . | T | T | . | 0.52 | . | . | F | 0.35 | 0.65 |
| Asp | 218 | . | . | . | . | T | T | . | 0.80 | . | . | F | 0.65 | 0.61 |
| Ser | 219 | . | . | . | . | T | T | . | 1.66 | * | . | . | 0.50 | 0.54 |
| Cys | 220 | . | . | B | . | . | T | . | 1.38 | . | . | . | 0.70 | 0.88 |
| His | 221 | . | A | B | . | . | . | . | 1.00 | . | . | . | 0.60 | 0.53 |
| His | 222 | . | A | . | . | . | . | C | 1.08 | . | . | . | 0.81 | 0.40 |
| Glu | 223 | . | A | . | . | . | . | C | 0.73 | . | . | . | 0.67 | 1.16 |
| Ala | 224 | . | A | . | . | . | . | C | 1.08 | . | . | . | 1.43 | 0.84 |
| Ala | 225 | . | . | . | . | . | T | C | 1.16 | . | . | F | 2.74 | 1.24 |
| Pro | 226 | . | . | . | . | T | T | . | 0.89 | . | . | F | 3.10 | 0.72 |
| Gly | 227 | . | . | . | . | T | T | . | 0.68 | . | * | F | 2.49 | 0.96 |
| Lys | 228 | . | . | . | . | T | T | . | 0.72 | . | * | F | 1.90 | 1.49 |
| Ala | 229 | . | . | . | . | . | T | C | 1.31 | * | * | F | 2.16 | 1.92 |
| Ser | 230 | . | . | B | . | . | T | . | 1.04 | . | * | F | 2.12 | 3.25 |
| Tyr | 231 | . | . | B | . | . | T | . | 0.44 | . | * | F | 1.98 | 1.21 |
| Lys | 232 | . | . | B | . | . | T | . | -0.02 | * | * | F | 1.70 | 0.98 |
| Asp | 233 | . | . | B | B | . | . | . | -0.92 | * | * | . | 0.38 | 0.61 |
| Val | 234 | . | . | B | B | . | . | . | -1.19 | . | . | . | -0.09 | 0.29 |
| Leu | 235 | . | . | B | B | . | . | . | -1.74 | . | . | . | 0.04 | 0.11 |
| Leu | 236 | . | . | B | B | . | . | . | -1.71 | * | . | . | -0.43 | 0.05 |
| Val | 237 | . | . | B | B | . | . | . | -2.61 | * | . | . | -0.60 | 0.10 |
| Val | 238 | . | . | B | B | . | . | . | -2.91 | . | * | . | -0.60 | 0.09 |
| Val | 239 | . | . | B | B | . | . | . | -2.87 | . | . | . | -0.60 | 0.14 |

TABLE 1-continued

| Res | Pos | Garni Alpha | Chou- Alpha | Garni Beta | Chou- Beta | Garni Turn | Chou- Turn | Garni Coil | Kyte- Hydro | Eisen Alpha | Eisen Beta | Karpl Flexi | James Antig | Emini Surfa |
|---|---|---|---|---|---|---|---|---|---|---|---|---|---|---|
| Pro | 240 | . | . | B | B | . | . | . | -2.87 | . | * | . | -0.60 | 0.16 |
| Val | 241 | . | . | B | B | . | . | . | -2.87 | . | . | . | -0.60 | 0.18 |
| Ser | 242 | . | . | B | B | . | . | . | -2.61 | . | * | . | -0.60 | 0.20 |
| Leu | 243 | . | . | B | B | . | . | . | -2.57 | . | . | . | -0.60 | 0.13 |
| Leu | 244 | . | . | B | B | . | . | . | -2.57 | . | * | . | -0.60 | 0.14 |
| Leu | 245 | . | . | B | B | . | . | . | -2.67 | . | . | . | -0.60 | 0.08 |
| Met | 246 | . | . | B | B | . | . | . | -2.62 | * | . | . | -0.60 | 0.14 |
| Leu | 247 | . | . | B | B | . | . | . | -3.02 | * | . | . | -0.60 | 0.14 |
| Val | 248 | . | . | B | B | . | . | . | -2.51 | . | . | . | -0.60 | 0.14 |
| Thr | 249 | . | . | B | B | . | . | . | -2.29 | . | . | . | -0.60 | 0.19 |
| Leu | 250 | . | . | B | B | . | . | . | -1.77 | . | . | . | -0.60 | 0.24 |
| Phe | 251 | . | . | B | B | . | . | . | -1.20 | . | . | . | -0.60 | 0.34 |
| Ser | 252 | . | . | . | B | T | . | . | -0.68 | . | . | . | -0.20 | 0.32 |
| Ala | 253 | . | . | . | B | T | . | . | -0.49 | . | . | . | -0.20 | 0.40 |
| Trp | 254 | . | . | . | B | T | . | . | -0.39 | . | . | . | -0.20 | 0.25 |
| His | 255 | . | . | . | B | T | . | . | -0.24 | . | . | . | -0.20 | 0.29 |
| Trp | 256 | . | . | . | B | T | . | . | 0.16 | . | . | . | -0.20 | 0.15 |
| Cys | 257 | . | . | B | . | . | T | . | 0.11 | * | . | . | 0.14 | 0.20 |
| Pro | 258 | . | . | . | . | T | T | . | 0.74 | * | . | . | 0.88 | 0.14 |
| Cys | 259 | . | . | . | . | T | T | . | 1.08 | . | . | . | 1.52 | 0.27 |
| Ser | 260 | . | . | . | . | T | T | . | 1.16 | . | . | F | 3.06 | 1.01 |
| Gly | 261 | . | . | . | . | T | T | . | 1.49 | . | . | F | 3.40 | 1.30 |
| Lys | 262 | . | . | . | . | T | T | . | 2.16 | . | . | F | 3.06 | 4.86 |
| Lys | 263 | . | . | . | . | T | T | . | 1.51 | . | * | F | 2.72 | 6.06 |
| Lys | 264 | . | . | . | . | T | T | . | 2.14 | . | * | F | 2.38 | 4.54 |
| Lys | 265 | . | A | B | . | . | . | . | 1.86 | . | * | F | 1.24 | 3.09 |
| Asp | 266 | . | A | B | . | . | . | . | 2.20 | . | . | F | 0.90 | 1.56 |
| Val | 267 | . | A | B | . | . | . | . | 2.27 | . | . | . | 0.75 | 1.30 |
| His | 268 | . | A | B | . | . | . | . | 1.37 | * | . | . | 0.75 | 1.28 |
| Ala | 269 | . | A | B | . | . | . | . | 0.98 | * | . | . | 0.90 | 0.57 |
| Asp | 270 | . | A | B | . | . | . | . | 0.72 | . | . | . | 0.90 | 0.76 |
| Arg | 271 | . | A | B | . | . | . | . | 0.72 | * | . | F | 1.35 | 0.86 |
| Val | 272 | . | A | . | . | . | . | C | 1.27 | * | * | F | 2.30 | 1.47 |
| Gly | 273 | . | . | . | . | . | T | C | 1.30 | * | . | F | 3.00 | 1.27 |
| Pro | 274 | . | . | . | . | . | T | C | 1.89 | * | . | F | 2.70 | 1.13 |
| Glu | 275 | . | . | . | . | . | T | C | 1.68 | * | * | F | 2.40 | 2.44 |
| Thr | 276 | . | . | . | . | . | T | C | 0.76 | * | * | F | 2.10 | 3.82 |
| Glu | 277 | . | . | . | . | . | . | C | 0.76 | * | . | F | 1.60 | 2.03 |
| Asn | 278 | . | . | B | . | . | T | . | 1.10 | * | . | F | 0.85 | 0.87 |
| Pro | 279 | . | . | B | . | . | T | . | 1.31 | * | . | F | 0.40 | 1.05 |
| Leu | 280 | . | . | B | . | . | T | . | 0.50 | * | . | F | 1.00 | 1.01 |
| Val | 281 | . | . | B | . | . | T | . | 0.60 | * | . | F | 0.38 | 0.52 |
| Gln | 282 | . | . | B | . | . | . | . | 0.21 | * | . | F | 0.31 | 0.52 |
| Asp | 283 | . | . | B | . | . | . | . | -0.18 | * | . | F | 0.44 | 0.80 |
| Leu | 284 | . | . | B | . | . | . | . | -0.36 | * | . | . | 0.57 | 1.38 |
| Pro | 285 | . | . | B | . | . | . | . | 0.07 | * | . | . | 1.30 | 1.02 |
| Ter | 286 | . | . | B | . | . | . | . | 0.53 | * | . | . | 1.02 | 0.78 |

What is claimed is:

1. An isolated protein comprising an amino acid sequence selected from the group consisting of:
   (a) amino acid residues 1 to 285 of SEQ ID NO:2;
   (b) amino acid residues 2 to 285 of SEQ ID NO:2;
   (c) amino acid residues 23 to 285 of SEQ ID NO:2;
   (d) amino acid residues 23 to 232 of SEQ ID NO:2;
   (e) amino acid residues 233 to 255 of SEQ ID NO:2; and
   (f) amino acid residues 256 to 285 of SEQ ID NO:2.

2. The isolated protein of claim 1 which comprises amino acid sequence (a).

3. The isolated protein of claim 1 which comprises amino acid sequence (b).

4. The isolated protein of claim 1 which comprises amino acid sequence (c).

5. The isolated protein of claim 1 which comprises amino acid sequence (d).

6. The isolated protein of claim 1 which comprises amino acid sequence (e).

7. The isolated protein of claim 1 which comprises amino acid sequence (f).

8. The isolated protein of claim 1 wherein acid sequence further comprises a heterologous polypeptide.

9. The isolated protein of claim 8 wherein the heterologous polypeptide is the Fc domain of immunoglobulin.

10. The protein of claim 1, wherein said isolated protein is glycosylated.

11. A composition comprising the isolated protein of claim 1.

12. The composition of claim 11, wherein the composition further comprises a liposome.

13. A protein produced by a method comprising:
    (a) culturing a host cell under conditions suitable to produce the isolated protein of claim 1; and
    (b) recovering the protein from the host cell culture.

14. An isolated protein comprising an amino acid sequence selected from the group consisting of:
    (a) the amino acid sequence of the full-length polypeptide, which amino acid sequence is encoded by the cDNA clone contained in ATCC Deposit No. 209623;
    (b) the amino acid sequence of the full-length polypeptide, excluding the N-terminal methionine residue, which amino acid sequence is encoded by the cDNA clone contained in ATCC Deposit No. 209623;
    (c) the amino acid sequence of the mature polypeptide, which amino acid sequence is encoded by the cDNA clone contained in ATCC Deposit No. 209623;
    (d) the amino acid sequence of the extracellular domain of the polypeptide, which amino acid sequence is encoded by the cDNA clone contained in ATCC Deposit No. 209623;
    (e) the amino acid sequence of the transmembrane domain of the polypeptide, which amino acid sequence is encoded by the cDNA clone contained in ATCC Deposit No. 209623; and
    (f) the amino acid sequence of the intracellular domain of the polypeptide, which amino acid sequence is encoded by the cDNA clone contained in ATCC Deposit No. 209623.

15. The protein of claim 14 which comprises amino acid sequence (a).

16. The protein of claim 14 which comprises amino acid sequence (b).

17. The protein of claim 14 which comprises amino acid sequence (c).

18. The protein of claim 14 which comprises amino acid sequence (d).

19. The protein of claim 14 which comprises amino acid sequence (e).

20. The protein of claim 14 which comprises amino acid sequence (f).

21. The isolated protein of claim 14 wherein the amino acid sequence further comprises a heterologous polypeptide.

22. The isolated protein of claim 21 wherein the heterologous polypeptide is the Fc domain of immunoglobulin.

23. The isolated protein of claim 21, wherein said protein is glycosylated.

24. A composition comprising the protein of claim 14.

25. The composition of claim 24, wherein the composition further comprises a liposome.

26. A protein produced by a method comprising:
    (a) culturing a host cell under conditions suitable to produce the protein of claim 14; and
    (b) recovering the protein from the host cell culture.

27. An isolated protein comprising an amino acid sequence 90% or more identical to an amino acid sequence selected from the group consisting of:
    (a) amino acid residues 1 to 285 of SEQ ID NO:2;
    (b) amino acid residues 2 to 285 of SEQ ID NO:2;
    (c) amino acid residues 23 to 285 of SEQ ID NO:2; and
    (d) amino acid residues 23 to 232 of SEQ ID NO:2;
wherein said isolated protein is capable of generating or selecting an antibody that specifically binds amino acid residues of SEQ ID NO:2.

28. The isolated protein of claim 27 which further comprises an amino acid sequence 90% or more identical to amino acid residues 1 to 285 of SEQ ID NO:2.

29. The isolated protein of claim 27 which further comprises an amino acid sequence 90% or more identical to amino acid residues 2 to 285 of SEQ ID NO:2.

30. The isolated polypeptide of claim 27 which further comprises an amino acid sequence 90% or more identical to amino acid residues 23 to 285 of SEQ ID NO:2.

31. The isolated protein of claim 27 which further comprises an amino acid sequence 90% or more identical to amino acid residues 23 to 232 of SEQ ID NO:2.

32. The isolated protein of claim 27 which further comprises an amino acid sequence 95% or more identical to amino acid residues 1 to 285 of SEQ ID NO:2.

33. The isolated protein of claim 27 which further comprises an amino acid sequence 95% or more identical to amino acid residues 2 to 285 of SEQ ID NO:2.

34. The isolated protein of claim 27 which further comprises an amino acid sequence 95% or more identical to amino acid residues 23 to 285 of SEQ ID NO:2.

35. The isolated protein of claim 27 which further comprises an amino acid sequence 95% or more identical to amino acid residues 23 to 232 of SEQ ID NO:2.

36. The isolated protein of claim 27 wherein the amino acid sequence further comprises a heterologous polypeptide.

37. The isolated protein of claim 36 wherein the heterologous polypeptide is the Fc domain of immunoglobulin.

38. The isolated protein of claim 36, wherein said isolated protein is glycosylated.

39. A composition comprising the isolated protein of claim 27.

40. The composition of claim 39, wherein the composition further comprises a liposome.

41. A protein produced by a method comprising:
    (a) culturing a host cell under conditions suitable to produce the protein of claim 27; and
    (b) recovering the protein from the host cell culture.

42. An isolated protein comprising an amino acid sequence 90% or more identical to an amino acid sequence selected from the group consisting of:
    (a) the amino acid sequence of the full-length polypeptide, which amino acid sequence is encoded by the cDNA contained in ATCC Deposit No. 209623;
    (b) the amino acid sequence of the full-length polypeptide excluding the amino-terminal methionine, which amino acid sequence is encoded by the cDNA contained in ATCC Deposit No. 209623;
    (c) the amino acid sequence of the mature polypeptide, which amino acid sequence is encoded by the cDNA contained in ATCC Deposit No. 209623; and
    (d) the amino acid sequence of the extracellular domain of the polypeptide, which amino acid sequence is encoded by the cDNA clone contained in ATCC Deposit No. 209623;
wherein said isolated protein is capable of generating or selecting an antibody that specifically binds amino acid residues of SEQ ID NO:2.

43. The isolated protein of claim 42 which further comprises an amino acid sequence 90% or more identical to the amino acid sequence of the full-length polypeptide, which amino acid sequence is encoded by the cDNA contained in ATCC Deposit No. 209623.

44. The isolated protein of claim 42 which further comprises an amino acid sequence 90% or more identical to the amino acid sequence of the full-length polypeptide excluding the amino-terminal methionine, which amino acid sequence is encoded by the cDNA contained in ATCC Deposit No. 209623.

45. The isolated protein of claim 42 which further comprises an amino acid sequence 90% or more identical to the amino acid sequence of the mature polypeptide, which amino acid sequence is encoded by the cDNA contained in ATCC Deposit No. 209623.

46. The isolated protein of claim 42 which further comprises an amino acid sequence 90% or more identical to the amino acid sequence of the extracellular polypeptide, which amino acid sequence is encoded by the cDNA contained in ATCC Deposit No. 209623.

47. The isolated protein of claim 42 which further comprises an amino acid sequence 95% or more identical to the amino acid sequence of the full-length polypeptide, which amino acid sequence is encoded by the cDNA contained in ATCC Deposit No. 209623.

48. The isolated protein of claim 42 which further comprises an amino acid sequence 95% or more identical to the amino acid sequence of the full-length polypeptide excluding the amino-terminal methionine, which amino acid sequence is encoded by the cDNA contained in ATCC Deposit No. 209623.

49. The isolated protein of claim 42 which further comprises an amino acid sequence 95% or more identical to the amino acid sequence of the mature polypeptide, which amino acid sequence is encoded by the cDNA contained in ATCC Deposit No. 209623.

50. The isolated protein of claim 42 which further comprises an amino acid sequence 95% or more identical to the amino acid sequence of the extracellular polypeptide, which amino acid sequence is encoded by the cDNA contained in ATCC Deposit No. 209623.

51. The isolated protein of claim 42 wherein the amino acid sequence further comprises a heterologous polypeptide.

52. The isolated protein of claim 51 wherein the heterologous polypeptide is the Fc domain of immunoglobulin.

53. The isolated protein of claim 51 wherein said isolated protein is glycosylated.

54. A composition comprising the isolated protein of claim 42.

55. The composition of claim 54, wherein the composition further comprises a liposome.

56. A protein produced by a method comprising:
    (a) culturing a host cell under conditions suitable to produce the isolated protein of claim 42; and
    (b) recovering the protein from the host cell culture.

57. An isolated protein comprising an amino acid sequence selected from the group consisting of:
    (a) amino acid residues 1 to 20 of SEQ ID NO:2;
    (b) amino acid residues 21 to 40 of SEQ ID NO:2;
    (c) amino acid residues 41 to 60 of SEQ ID NO:2;
    (d) amino acid residues 61 to 80 of SEQ ID NO:2;
    (e) amino acid residues 81 to 100 of SEQ ID NO:2;
    (f) amino acid residues 102 to 120 of SEQ ID NO:2;
    (g) amino acid residues 121 to 140 of SEQ ID NQ:2;
    (h) amino acid residues 141 to 160 of SEQ ID NQ:2;
    (i) amino acid residues 161 to 180 of SEQ ID NO:2;
    (j) amino acid residues 181 to 200 of SEQ ID NO:2;
    (k) amino acid residues 201 to 220 of SEQ ID NO:2;
    (l) amino acid residues 221 to 240 of SEQ ID NO:2;
    (m) amino acid residues 241 to 260 of SEQ ID NO:2;
    (n) amino acid residues 261 to 280 of SEQ ID NO:2;
    (o) amino acid residues 29 to 32 of SEQ ID NO:2;
    (p) amino acid residues 39 to 45 of SEQ ID NO:2;
    (q) amino acid residues 48 to 50 of SEQ ID NO:2;
    (r) amino acid residues 91 to 101 of SEQ ID NO:2;
    (s) amino acid residues 136 to 146 of SEQ ID NO:2;
    (t) amino acid residues 162 to 178 of SEQ ID NO:2;
    (u) amino acid residues 216 to 233 of SEQ ID NO:2;
    (v) amino acid residues 257 to 285 of SEQ ID NO:2; and
    (w) a fragment of amino residues 1 to 285 of SEQ ID NO:2,
wherein said isolated protein activates dendritic cells.

58. The isolated protein of claim 57 comprises amino acid sequence (a).

59. The isolated protein of claim 57 comprises amino acid sequence (b).

60. The isolated protein of claim 57 comprises amino acid sequence (c).

61. The isolated protein of claim 57 which comprises amino acid sequence (d).

62. The isolated protein of claim 57 which comprises amino acid sequence (e).

63. The isolated protein of claim 57 which comprises amino acid sequence (f).

64. The isolated protein of claim 57 which comprises amino acid sequence (g).

65. The isolated protein of claim 57 which comprises amino acid sequence (h).

66. The isolated protein of claim 57 which comprises amino acid sequence (i).

67. The isolated protein of claim 57 which comprises amino acid sequence (j).

68. The isolated protein of claim 57 which comprises amino acid sequence (k).

69. The isolated protein of claim 57 which comprises amino acid sequence (l).

70. The isolated protein of claim 57 which comprises amino acid sequence (m).

71. The isolated protein of claim 57 which comprises amino acid sequence (n).

72. The isolated protein of claim 57 which comprises amino acid sequence (o).

73. The isolated protein of claim 57 which comprises amino acid sequence (p).

74. The isolated protein of claim 57 which comprises amino acid sequence (q).

75. The isolated protein of claim 57 which comprises amino acid sequence (r).

76. The isolated protein of claim 57 which comprises amino acid sequence (s).

77. The isolated protein of claim 57 which comprises amino acid sequence (t).

78. The isolated protein of claim 57 which comprises amino acid sequence (u).

79. The isolated protein of claim 57 which comprises amino acid sequence (v).

80. The isolated protein of claim 57 which comprises amino acid sequence (w).

81. The isolated protein of claim 57 wherein the amino acid sequence further comprises a heterologous polypeptide.

82. The isolated protein of claim 81 wherein the heterologous polypeptide is the Fc domain of immunoglobulin.

83. The isolated protein of claim 81, wherein said isolated protein is glycosylated.

84. A composition comprising the isolated protein of claim 57.

85. A The composition of claim 84, wherein the composition further comprises a liposome.

86. A protein produced by a method comprising:
   (a) culturing a host cell under conditions suitable to produce the isolated protein of claim 80; and
   (b) recovering the protein from the host cell culture.

87. An isolated protein comprising at least 30 contiguous amino acid residues of SEQ ID NO:2.

88. The isolated protein of claim 87 wherein the isolated protein comprises at least 50 contiguous amino acid residues of SEQ ID NO:2.

89. The isolated protein of claim 87 wherein the amino acid sequence further comprises a heterologous polypeptide.

90. The isolated protein of claim 89 wherein the heterologous polypeptide is the Fc domain of immunoglobulin.

91. The isolated protein of claim 89, wherein said isolated protein is glycosylated.

92. A composition comprising the isolated protein of claim 87.

93. The composition of claim 92, wherein the composition further comprises a liposome.

94. A protein produced by a method comprising:
   (a) culturing a host cell under conditions suitable to produce the isolated protein of claim 87; and
   (b) recovering the protein from the host cell culture.

95. An isolated protein comprising a polypeptide selected from the group consisting of:
   (a) a polypeptide consisting of amino acid residues +1 to +285 of SEQ ID NO:2, in which 1 or more amino acid residues are substituted, deleted or added, in any combination and wherein said polypeptide is capable of generating or selecting an antibody specific for the polypeptide of SEQ ID NO:2;
   (b) a polypeptide consisting of a fragment of SEQ ID NO:2 which fragment has leukocyte proliferation inhibitory activity and in which 1 or more amino acid residues are substituted, deleted or added, in any combination; and
   (c) a polypeptide consisting of a fragment of SEQ ID NO:2 which fragment has leukocyte proliferation inhibitory activity and in which 1 or more amino acid residues are substituted, deleted or added, in any combination and wherein said polypeptide is capable of generating or selecting an antibody specific for the polypeptide of SEQ ID NO:2.

* * * * *

SEQUENCE LISTING

<160> NUMBER OF SEQ ID NOS: 13

<210> SEQ ID NO 1
<211> LENGTH: 3220
<212> TYPE: DNA
<213> ORGANISM: Homo sapiens

<400> SEQUENCE: 1

```
gaaggaccac agctcctccc gtgcatccac tcggcctggg aggttctgga ttttggctgt      60
cgagggagtt tgcctgcctc tccagagaaa gatggtcatg aggcccctgt ggagtctgct     120
tctctgggaa gccctacttc ccattacagt tactggtgcc caagtgctga gcaaagtcgg     180
gggctcggtg ctgctggtgg cagcgcgtcc ccctggcttc caagtccgtg aggctatctg     240
gcgatctctc tggccttcag aagagctcct ggccacgttt ttccgaggct ccctggagac     300
```

-continued

```
tctgtaccat tcccgcttcc tgggccgagc ccagctacac agcaacctca gcctggagct    360
cgggccgctg gagtctggag acagcggcaa cttctccgtg ttgatggtgg acacaagggg    420
ccagccctgg acccagaccc tccagctcaa ggtgtacgat gcagtgccca ggcccgtggt    480
acaagtgttc attgctgtag aaagggatgc tcagccctcc aagacctgcc aggttttctt    540
gtcctgttgg gcccccaaca tcagcgaaat aacctatagc tggcgacggg agacaaccat    600
ggactttggt atggaaccac acagcctctt cacagacgga caggtgctga gcatttccct    660
gggaccagga gacagagatg tggcctattc ctgcattgtc tccaaccctg tcagctggga    720
cttggccaca gtcacgccct gggatagctg tcatcatgag gcagcaccag ggaaggcctc    780
ctacaaagat gtgctgctgg tggtggtgcc tgtctcgctg ctcctgatgc tggttactct    840
cttctctgcc tggcactggt gcccctgctc agggaaaaag aaaaaggatg tccatgctga    900
cagagtgggc ccagagacag agaaccccct tgtgcaggat ctgccataaa ggacaatatg    960
aactgatgcc tggactatca gtaaccccac tgcacaggca cacgatgctc tgggacataa   1020
ctggtgcctg gaaatcacca tggtcctcat atctcccatg ggaatcctgt cctgcctcga   1080
aggagcagcc tgggcagcca tcacaccacg aggacaggaa gcaccagcac gtttcacacc   1140
tcccccttcc ctctcccatc ttctcatatc ctggctcttc tctgggcaag atgagccaag   1200
cagaacattc catccaggac actggaagtt ctccaggatc cagatccatg ggacattaa    1260
tagtccaagg cattccctcc cccaccacta ttcataaagt attaaccaac tggcaccaag   1320
gaattgcctc cagcctgagt cctaggctct aaaagatatt acatatttga actaatagag   1380
gaactctgag tcacccatgc cagcatcagc ttcagcccca gaccctgcag tttgagatct   1440
gatgcttcct gagggccaag gcattgctgt aagaaaaggt ctagaaatag gtgaaagtga   1500
gaggtgggggg acaggggttt ctctttctgg cctaaggact ttcaggtaat cagagttcat   1560
gggccctcaa aggtaaattg cagttgtaga caccgaggat ggttgacaac ccatggttga   1620
gatgggcacc gttttgcagg aaacaccata ttaatagaca tcctcaccat ctccatccgc   1680
tctcacgcct cctgcaggat ctgggagtga gggtggagag tctttcctca cgctccagca   1740
cagtggccag gaaaagaaat actgaatttg ccccagccaa caggacgttc ttgcacaact   1800
tcaagaaaag cagctcagct caggatgagt cttcctgcct gaaactgaga gagtgaagaa   1860
ccataaaacg ctatgcagaa ggaacattat ggagagaaag ggtactgagg cactctagaa   1920
tctgccacat tcattttcaa atgcaaatgc agaagactta ccttagttca aggggagggg   1980
acaaagaccc cacagcccaa cagcaggact gtagaggtca ctctgactcc atcaaacttt   2040
ttattgtggc catcttagga aaatacattc tgccccctgaa tgattctgtc tagaaaagct   2100
ctggagtatt gatcactact ggaaaaacac ttaaggagct aaacttacct tcggggatta   2160
ttagctgata aggttcacag tttctctcac ccaggtgtaa ctggattttt tctggggcct   2220
caatccagtc ttgataacag cgaggaaaga ggtattgaag aaacagggt gggtttgaag    2280
tactattttc cccagggtgg cttcaatctc ccacctagga tgtcagccc tgtccaagga    2340
ccttccctct tctcccccag ttccctgggc aatcacttca ccttggacaa aggatcagca   2400
cagctggcct ccagatccac atcaccactc ttccactcga ttgttcccag atcctccctg   2460
cctggcctgc tcagaggttc cctgttggta acctggcttt atcaaattct catccctttc   2520
ccacacccac ttctctccta tcaccttccc ccaagattac ctgaacaggg tccatggcca   2580
ctcaacctgt cagcttgcac catccccacc tgccacctac agtcaggcca catgcctggt   2640
```

-continued

```
cactgaatca tgcaaaactg gcctcagtcc ctaaaaatga tgtggaaagg aaagcccagg      2700
atctgacaat gagccctggt ggatttgtgg ggaaaaaata cacagcactc cccacctttc      2760
tttcgttcat ctccagggcc ccacctcaga tcaaagcagc tctggatgag atgggacctg      2820
cagctctccc tccacaaggt gactcttagc aacctcattt cgacagtggt ttgtagcgtg      2880
gtgcaccagg gccttgttga acagatccac actgctctaa taaagttccc atccttaatg      2940
actcacttgt caactagtgg actaattaac cctccaccaa aaaacacaa agtgcttctg       3000 tgagaccaat tttgtgctaa tgagcattga gactgatgct ttgtaagtca caccacaaca      3060
aatattgatt gagggcgctg catgtgctgg gtacatttct tggcacttgg gaatcagtag      3120
tcaagcgaaa cccttgcctt tgagagttta tggtctggat aatataaata aacaagtaag      3180
cataaaaaaa aaaaaaaaaa aaaaaaaaaa aaaaaaaaa                             3220
```

<210> SEQ ID NO 2
<211> LENGTH: 285
<212> TYPE: PRT
<213> ORGANISM: Homo sapiens

<400> SEQUENCE: 2

```
Met Val Met Arg Pro Leu Trp Ser Leu Leu Trp Glu Ala Leu Leu
  1               5                  10                  15

Pro Ile Thr Val Thr Gly Ala Gln Val Leu Ser Lys Val Gly Gly Ser
                 20                  25                  30

Val Leu Leu Val Ala Ala Arg Pro Pro Gly Phe Gln Val Arg Glu Ala
             35                  40                  45

Ile Trp Arg Ser Leu Trp Pro Ser Glu Glu Leu Leu Ala Thr Phe Phe
         50                  55                  60

Arg Gly Ser Leu Glu Thr Leu Tyr His Ser Arg Phe Leu Gly Arg Ala
 65                  70                  75                  80

Gln Leu His Ser Asn Leu Ser Leu Glu Leu Gly Pro Leu Glu Ser Gly
                 85                  90                  95

Asp Ser Gly Asn Phe Ser Val Leu Met Val Asp Thr Arg Gly Gln Pro
            100                 105                 110

Trp Thr Gln Thr Leu Gln Leu Lys Val Tyr Asp Ala Val Pro Arg Pro
        115                 120                 125

Val Val Gln Val Phe Ile Ala Val Glu Arg Asp Ala Gln Pro Ser Lys
    130                 135                 140

Thr Cys Gln Val Phe Leu Ser Cys Trp Ala Pro Asn Ile Ser Glu Ile
145                 150                 155                 160

Thr Tyr Ser Trp Arg Arg Glu Thr Thr Met Asp Phe Gly Met Glu Pro
                165                 170                 175

His Ser Leu Phe Thr Asp Gly Gln Val Leu Ser Ile Ser Leu Gly Pro
            180                 185                 190

Gly Asp Arg Asp Val Ala Tyr Ser Cys Ile Val Ser Asn Pro Val Ser
        195                 200                 205

Trp Asp Leu Ala Thr Val Thr Pro Trp Asp Ser Cys His His Glu Ala
    210                 215                 220

Ala Pro Gly Lys Ala Ser Tyr Lys Asp Val Leu Leu Val Val Pro
225                 230                 235                 240

Val Ser Leu Leu Leu Met Leu Val Thr Leu Phe Ser Ala Trp His Trp
                245                 250                 255

Cys Pro Cys Ser Gly Lys Lys Lys Asp Val His Ala Asp Arg Val
            260                 265                 270
```

```
Gly Pro Glu Thr Glu Asn Pro Leu Val Gln Asp Leu Pro
        275                 280                 285

<210> SEQ ID NO 3
<211> LENGTH: 335
<212> TYPE: PRT
<213> ORGANISM: Homo sapiens

<400> SEQUENCE: 3

Met Asp Pro Lys Gly Leu Leu Ser Leu Thr Phe Val Leu Phe Leu Ser
 1               5                  10                  15

Leu Ala Phe Gly Ala Ser Tyr Gly Thr Gly Gly Arg Met Met Asn Cys
                20                  25                  30

Pro Lys Ile Leu Arg Gln Leu Gly Ser Lys Val Leu Pro Leu Thr
            35                  40                  45

Tyr Glu Arg Ile Asn Lys Ser Met Asn Lys Ser Ile His Ile Val Val
 50                  55                  60

Thr Met Ala Lys Ser Leu Glu Asn Ser Val Glu Asn Lys Ile Val Ser
 65                  70                  75                  80

Leu Asp Pro Ser Glu Ala Gly Pro Pro Arg Tyr Leu Gly Asp Arg Tyr
                85                  90                  95

Lys Phe Tyr Leu Glu Asn Leu Thr Leu Gly Ile Arg Glu Ser Arg Lys
            100                 105                 110

Glu Asp Glu Gly Trp Tyr Leu Met Thr Leu Glu Lys Asn Val Ser Val
            115                 120                 125

Gln Arg Phe Cys Leu Gln Leu Arg Leu Tyr Glu Gln Val Ser Thr Pro
130                 135                 140

Glu Ile Lys Val Leu Asn Lys Thr Gln Glu Asn Gly Thr Cys Thr Leu
145                 150                 155                 160

Ile Leu Gly Cys Thr Val Glu Lys Gly Asp His Val Ala Tyr Ser Trp
                165                 170                 175

Ser Glu Lys Ala Gly Thr His Pro Leu Asn Pro Ala Asn Ser Ser His
            180                 185                 190

Leu Leu Ser Leu Thr Leu Gly Pro Gln His Ala Asp Asn Ile Tyr Ile
            195                 200                 205

Cys Thr Val Ser Asn Pro Ile Ser Asn Asn Ser Gln Thr Phe Ser Pro
210                 215                 220

Trp Pro Gly Cys Arg Thr Asp Pro Ser Glu Thr Lys Pro Trp Ala Val
225                 230                 235                 240

Tyr Ala Gly Leu Leu Gly Gly Val Ile Met Ile Leu Ile Met Val Val
                245                 250                 255

Ile Leu Gln Leu Arg Arg Arg Gly Lys Thr Asn His Tyr Gln Thr Thr
            260                 265                 270

Val Glu Lys Lys Ser Leu Thr Ile Tyr Ala Gln Val Gln Lys Pro Gly
            275                 280                 285

Pro Leu Gln Lys Lys Leu Asp Ser Phe Pro Ala Gln Asp Pro Cys Thr
290                 295                 300

Thr Ile Tyr Val Ala Ala Thr Glu Pro Val Pro Glu Ser Val Gln Glu
305                 310                 315                 320

Thr Asn Ser Ile Thr Val Tyr Ala Ser Val Thr Leu Pro Glu Ser
                325                 330                 335

<210> SEQ ID NO 4
<211> LENGTH: 733
<212> TYPE: DNA
<213> ORGANISM: Homo sapiens
```

-continued

<400> SEQUENCE: 4

```
gggatccgga gcccaaatct tctgacaaaa ctcacacatg cccaccgtgc ccagcacctg      60
aattcgaggg tgcaccgtca gtcttcctct tccccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agccctccca ccccccatcg     360
agaaaaccat ctccaaagcc aagggcagc cccgagaacc acaggtgtac accctgcccc      420
catcccggga tgagctgacc aagaaccagg tcagcctgac ctgcctggtc aaaggcttct     480
atccaagcga catcgccgtg gagtgggaga gcaatgggca gccggagaac aactacaaga     540
ccacgcctcc cgtgctggac tccgacggct ccttcttcct ctacagcaag ctcaccgtgg     600
acaagagcag gtggcagcag gggaacgtct tctcatgctc cgtgatgcat gaggctctgc     660
acaaccacta cacgcagaag agcctctccc tgtctccggg taaatgagtg cgacggccgc     720
gactctagag gat                                                        733
```

<210> SEQ ID NO 5
<211> LENGTH: 5
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any amino acid

<400> SEQUENCE: 5

Trp Ser Xaa Trp Ser
 1               5

<210> SEQ ID NO 6
<211> LENGTH: 86
<212> TYPE: DNA
<213> ORGANISM: Homo sapiens

<400> SEQUENCE: 6

```
gcgcctcgag atttccccga aatctagatt tccccgaaat gatttccccg aaatgatttc      60
cccgaaatat ctgccatctc aattag                                           86
```

<210> SEQ ID NO 7
<211> LENGTH: 27
<212> TYPE: DNA
<213> ORGANISM: Homo sapiens

<400> SEQUENCE: 7

```
gcggcaagct ttttgcaaag cctaggc                                          27
```

<210> SEQ ID NO 8
<211> LENGTH: 271
<212> TYPE: DNA
<213> ORGANISM: Homo sapiens

<400> SEQUENCE: 8

```
ctcgagattt ccccgaaatc tagatttccc cgaaatgatt tccccgaaat gatttccccg      60
aaatatctgc catctcaatt agtcagcaac catagtcccg cccctaactc cgcccatccc     120
gcccctaact ccgcccagtt ccgcccattc tccgcccat ggctgactaa ttttttttat      180
```

-continued

```
ttatgcagag gccgaggccg cctcggcctc tgagctattc cagaagtagt gaggaggctt        240
ttttggaggc ctaggctttt gcaaaaagct t                                       271

<210> SEQ ID NO 9
<211> LENGTH: 32
<212> TYPE: DNA
<213> ORGANISM: Homo sapiens

<400> SEQUENCE: 9
gcgctcgagg gatgacagcg atagaacccc gg                                       32

<210> SEQ ID NO 10
<211> LENGTH: 31
<212> TYPE: DNA
<213> ORGANISM: Homo sapiens

<400> SEQUENCE: 10
gcgaagcttc gcgactcccc ggatccgcct c                                        31

<210> SEQ ID NO 11
<211> LENGTH: 12
<212> TYPE: DNA
<213> ORGANISM: Homo sapiens

<400> SEQUENCE: 11
ggggactttc cc                                                             12

<210> SEQ ID NO 12
<211> LENGTH: 73
<212> TYPE: DNA
<213> ORGANISM: Homo sapiens

<400> SEQUENCE: 12
gcggcctcga ggggactttc ccggggactt tccggggact ttccgggact ttccatcctg         60
ccatctcaat tag                                                            73

<210> SEQ ID NO 13
<211> LENGTH: 256
<212> TYPE: DNA
<213> ORGANISM: Homo sapiens

<400> SEQUENCE: 13 ctcgaggga ctttcccggg gactttccgg ggactttccg ggactttcca tctgccatct          60
caattagtca gcaaccatag tcccgcccct aactccgccc atcccgcccc taactccgcc        120
cagttccgcc cattctccgc cccatggctg actaatttt tttatttatg cagaggccga        180
ggccgcctcg gcctctgagc tattccagaa gtagtgagga ggcttttttg gaggcctagg        240
cttttgcaaa aagctt                                                        256
```